US011414671B2

(12) United States Patent
Coppoolse et al.

(10) Patent No.: US 11,414,671 B2
(45) Date of Patent: Aug. 16, 2022

(54) HIGH TEMPERATURE SEED GERMINATION

(71) Applicant: RIJK ZWAAN ZAADTEELT EN ZAADHANDEL B.V., De Lier (NL)

(72) Inventors: Eric Roland Coppoolse, De Lier (NL); Miriam Post, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 50 days.

(21) Appl. No.: 16/600,645

(22) Filed: Oct. 14, 2019

(65) Prior Publication Data

US 2020/0032287 A1 Jan. 30, 2020

Related U.S. Application Data

(60) Division of application No. 15/451,497, filed on Mar. 7, 2017, now Pat. No. 10,968,460, which is a continuation-in-part of application No. PCT/EP2015/071082, filed on Sep. 15, 2015.

(30) Foreign Application Priority Data

Sep. 15, 2014 (EP) .................................... 14184800
Dec. 15, 2014 (EP) .................................... 14198005

(51) Int. Cl.
*C12N 15/82* (2006.01)
*C12N 9/90* (2006.01)
*C12Q 1/6895* (2018.01)

(52) U.S. Cl.
CPC ........... *C12N 15/8267* (2013.01); *C12N 9/90* (2013.01); *C12Q 1/6895* (2013.01); *C12Y 503/99009* (2013.01); *C12Q 2600/156* (2013.01)

(58) Field of Classification Search
None
See application file for complete search history.

(56) References Cited

U.S. PATENT DOCUMENTS 9,351,473 B2 5/2016 Woudenberg
2013/0260012 A1 10/2013 Rommens et al.
2014/0289901 A1 9/2014 Bovet et al.

FOREIGN PATENT DOCUMENTS

WO 2013/064499 5/2013

OTHER PUBLICATIONS

Hill M.A. et al Functional analysis of conserved histidines in ADP-glucose pyrophosphorylase from *Escherichia coli*. Biochem Biophys Res Commun. Mar. 17, 1998;244(2):573-7. (Year: 1998).*

Falcon-Perez JM et al. Functional domain analysis of the yeast ABC transporter Ycf1p by site-directed mutagenesis. J Biol Chem. Aug. 13, 1999;274(33):23584-90. (Year: 1999).*

Lamberg A. et al. Site-directed mutagenesis of the alpha subunit of human prolyl 4-hydroxylase. Identification of three histidine residues critical for catalytic activity. J Biol Chem. Apr. 28, 1995;270(17):9926-31. (Year: 1995).*

Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6. (Year: 1998).*

Argyris, st al., A gene encoding an abscisic acid biosynthetic enzyme (LsNCED4) collocates with the high temperature germination locus Htg6.1 in lettuce (*Lactuca* sp.) Theoretical and Applied Genetics (2011) 122(1):95-108.

Li, et al., Glycinebetaine enhances the tolerance of tomato plants to high temperature during germination of seeds and growth of seedlings, Plant, Cell and Environment (2011) 34(11):1931-1943.

Neuman, et al., The tomato mutation nxd1 reveals a gene necessary for neoxanthin biosynthesis and demonstrates that violaxanthin is a sufficient precursor for abscisic acid biosynthesis. The Plant Journal (2014) 78(1):80-93.

Schwember, et al., A genetic locus and gene expression patterns associated with the priming effect on lettuce seed germination at elevated temperatures, Plant Molecular Biology (2010) 73(1-2):105-118.

Shukla, et al., CAP2 enhances germination of transgenic tobacco seeds at high temperature and promotes heat stress tolerance in yeast, FESS Journal (2009) 276(18):5252-5262.

Tiedemann et al., Dissection of a complex seed phenotype: novel insights of FUSCA3 regulated developmental processes. Dev. Biol. (May 1, 2008) 317(1):1-12. Epub (Feb. 13, 2008).

Maple et al., Mutagenesis in *Arabidopsis*, Methods Mol. Biol. (2007) 362:197-206.

International Search Report dated Dec. 17, 2015, issued in Int'l Application No. PCT/EP2015/071082.

* cited by examiner

*Primary Examiner* — Cynthia E Collins
(74) *Attorney, Agent, or Firm* — Duane Morris LLP; Thomas J. Kowalski; Deborah L. Lu

(57) ABSTRACT

The present invention relates to a seed comprising in its genome a modified NXS gene and/or modified regulatory sequences thereof. The modified NXS gene and/or modified regulatory sequences thereof provides the seed with the capability to germinate at a high temperature as compared to a wild type seed not having the modified NXS gene. The modification to the gene and/or its regulatory sequences may lead to the expression of the NXS gene being substantially reduced or prevented. In addition to or alternatively, the seed can have a reduced level, reduced activity or complete absence of NXS protein. The modified NXS gene may for example comprise a premature stop codon and/or encode an NXS protein that comprises one or more amino acid substitutions.

13 Claims, 47 Drawing Sheets
(3 of 47 Drawing Sheet(s) Filed in Color)

Specification includes a Sequence Listing.

Fig. 1A

SEQ ID No: 1

>*Lactuca sativa* NXS DNA tcgattttga gactgatttt caatgtttaa gaaagtcact atattaccat aaaatttcga
ttttgacatg agttttttt tctcaattat atgattaaat tttcaattct gttgccatgt
caaccaacag agcgattcag gagatgttat tatggtttag aagctcgatt tgtacaacaa
ataaataaag gtcaatataa ttgttcaaac tcacttgtaa gtcagtgaaa agggcatagt
caccatttta ggagatgtta ttgcagttta gaagctcgtt gtttacaaca aataaatgac
aagacaatat tgtgatgtgg aagctatgcc cgatcttatg tggtaggatt gagtttcaaa
tatagggttt gcatcgaacc caatttcaca tatcttttta ggtcgaccta gtgggtcaaa
ctcacttaaa gttcagcaaa aatggtgtaa tcgcccattt aggtgacact ttttattata
atgtttaatg tttaattctt gtcagagtat ttcttcacaa atgacgtctg aaggtcaatc
tagtggttca aactaactta aaagtcggtg aaaagggtgt actcaccctt tcaggagata
ttattgtggt ttagaagctc gatttgtaca acaagtaaat taagacccct acaaggtcga
tcaagaagat gtttagtgag tttgaaccac taaatcgacc ttgtaggatt ctttatttat
ttattgtaca aatcgagctt ctaaaccata ataacatctt ttggaagggt gtctatgcat
tttttgctaa cttgtaagtg agtttgaatc attggaccga cctttattta attgttgtac
aaatcgagct tctaaaccac aacatctttt gaattggtca attggttgat attgcaaaaa
aattgtaaat gtagtgatat aattgaaaag aactcggtgt caaaatcaaa atttgtggt
aatataatga ctttcttgca atttgaaact cagtgtcaag atcaaaattt tggtaaactt
agtgacttta ttgcaattcg ggaaaaatgg ttaccgggag aacatagaga agtggtcatt
tggttgatat tgcaacaaaa ttataaatat attgacataa ttaaaaaaaa aaatttatgt
caaaatcaaa attttatggt aatatagtga gtacttgtca tttgtccttt atgaaatcaa
cccttgaggc tttaaatgag gttaccatat gaaattgagg atgcaacaaa ccttgaggac
taaaatcgta atttacaaaa ctaaatatca ggcttgaagt gaggttacca tatgaaattg
aggatgcaac aaaccttgag gactaaaatc gtaatttaca aaactaagta catgcgataa
caaattttgt ttggaaaatg acatggatat cggatagtgt tggattgcac ctttgaaatt
tgaatcttta tgtttttaag tagttatata tttggtaaca tatacaaata cacataacat
aataaaatta agatgtaatt ttgtttctct tttttaaaat attcatacac aaaatcaatt
ctatatcctc tcttcattaa aataaaagga aaactaaatt aaattgggtg agatgaatat
tcactcaaca gacaaaactt ttcatttctt ttctgaaacg aaaggaaaac aagactaccc
atctcttttg tatctatgat tgtactacca cttctaattt ctttttttata taacgacaac
ttcatgaaga atcctaaccc atttcatctc tcaatctcac ttactttctt acatctataa
tggctatctc ttcttgcctt tgtcaccatc aattagcact caaggtattg ttgctttccc
attctactgt atctacgtgt atctgcatat gttcaaacga attctccttc aacattcatg
gtttatttgc catttttgcg atctgggttc gagttatttc acgttcttgg tgctgaattt

Fig. 1B ggttggtttt gccaatttgt gtatttgcaa atgttgtaat cacttcacct ttgcatattc
atgatttgtt ttccaattta ccaactgggt atgattcatt ttgctttctt cgtatcaatt
tagttatttg tgcccatttc actctgttta tattgtgtgt ttgcagattg aatcatcact
ttgcatatat atgttatgat gttcatatac ttatataact tgtttgtttg tacttttccc
ccaattgaat tggtttactt tcccgttttc atgtttgaac tcgattggca atttagggtt
catagatgtt atctctttgt tgtagattaa cctcttaacg actgcatcca aacactcgaa
atccacattc gctattaaac ccatcaacac cgaattttac ggaatacata tcggaaacaa
gctaagaaat caatggagtt ttatgagagg atcaggagct ataatcatac caaacgaaag
cttcaatctg cgtcaaaaaa actcaaaatt gcaagcatca tgtaatcctt tcgtaccctt
tgtttatcat gagataattt atcgattaaa catctaaaac tttgttaatc ttatcaattt
atagttcgat tggatctttg ttcatgtagg ttttgctagt atgcaattag cgagtgatgc
ttttacatta ggaactgctg ctgttcttcc attctacact cttatgatcg cagctccaaa
atccgaattg gtaaatttta caatgttata aagcaaacaa aaaaaagaaa aaaaaaaagg
tatcgaaata actatttaat gctttttctt tttcttttga ctttataaaa acaagaatta
atcttataaa ctatatatag atatttcttt ttgacataat acataaagaa ctaaacttta
aacttacact catgggactc tgtctagctg atgtgagaca ctgaattgtt ttaacttgca
gactaaaaag tgtatgagaa gtagcatacc atacgtagtg cttggggttt tatactcgta
tcttctatat ctttcgtgga ccccggatac atttcggtta atgttcgcaa gcaaatattg
gctgcccgag gtaagaattt ctgcccgaat gatttgataa atgataatag cgtattttta
aactttacca tggtttattt tcagcttccg ggtgtagcta agatgttttc taatgagatg
acattagcct cggcgtggat ccatttgtta gccgttgacc tctacgcagc aaggtatgag
ggtatttacg tcttttgcac agacaagata tcagtagcca atcattgtcc cacctttatg
ggtgggatga aaatttgtaa attatgtacc attgtgtata agtctggtgc atgtcaaaca
caatctgatg cataccaaac acagtacatg aaacgacagt cgtactgatt gaagttaact
tatggttttg attggtggta acagacaggt gtatcaggat ggattggaga atgagattga
gacgcggcat tcggtttctc tttgtttgtt gttttgtcca attgggatac ttgttcatgc
tatcaccaag gctttaatta gtacatttag agaatcaaaa agtgagattc attgatgttt
ttatttttcc tatcaagtga tggagcattt atttgttcaa gtcttttaat ctaattggtt
atggttttgg tgtaaatctt tacaatttta atcatgaata tgttgtagga tttgtcttag
gggtttatga tagcattgac ataattaact cttcaacatt acacggaatc aaataaatct
ctaattccat aaaacacctt gtaatcctcc cttatcccaa cataatctac aattccactt
gtgccaataa ggacctttta gtcatttcac tattataagc tttttatcca cgacaagatc

Fig. 1C

SEQ ID No: 2

>*Lactuca sativa* NXS protein

MAISSCLCHHQLALKINLLTTASKHSKSTFAIKPINTEFYGIHIGNKLRNQWSFMRGSGAIIIPNESFNLR
QKNSKLQASCFASMQLASDAFTLGTAAVLPFYTLMIAAPKSELTKKCMRSSIPYVVLGVLYSYLLYLSWTP
DTFRLMFASKYWLPELPGVAKMFSNEMTLASAWIHLLAVDLYAARQVYQDGLENEIETRHSVSLCLLFCPI
GILVHAITKALISTFRESKSEIH

Fig. 2A

SEQ ID No: 3

>*Daucus carota* variant 1 NKS DNA ttggaatgggtgcattagtttatcagttcgtattgtagatttatgtttttataagggtgaaatttt
ctggaattcataattaacaggttgaaattctgccacctaaatgtgtgttggactgatcatttcagg
aactgaaaatgtgattgttgaatccttcttattcttgatcgattttctttatagccatcacagtta
agtttgcaaaataatgaacaagtttgttcttgagaatcaaaatgccctcctggtttcaatcctaaa
gttggggcagtacttgccgagttggacatgggaattattaaagtatctatctttatactgtctccc
aaatgcttatgatgaaaatcttgaaactgaatgcttagtaaattttcgtattatatggtgctggta
cttggttgcttctcattaactgttacttccattctcgccttgtagaccgaacattcaagcttgact
aggaagggcttctataatatcagcaagattcagctaaacccagttgctattgaaggcacaaacagt
gacctttatggccaacatgtggtgctttggacaaagatgagaaaagaatggagttttaagagagga
tcaatatctattgctggtccgactatggaaagatttgtgcttcacagaaaaagctctggagtgcag
gcttcatgtgagcccctttctttaaatctaccaaacatttttacttgtgtctaattttgtgtagt
tatcacaaattcttagaaatatgtatcagttactttacctttattgatgaaagcacctgtgatttt
gaacaaatgaaatgcaatgaaatcttgatggtcaatgatgcaaaactatgcaacaaaatataatcg
tgtataataaaaccaaagctttgatctgatgtacttttggcataaggaatgatctagttgtttgat
aggggtaattaaattgattgacatatatgcatttttattctaagcaactggttgagggtggttgtc
tggaacccagcagaggctaattatgccatagttcttgcatatacctgaccttgatgtgtatgactt
aatggcagtcttttcactgtggccttgcagggtttacaaattctcaaattgcaagtagtgtttta
cgttggcaaccgccgctgttcttccatttacaccctcatggttctggctccaaaagctactctgg
taataatttattgagacatggtgactgctttgactgattttatgttcacaacttcacatatgtaat
cagacatgaaaataatagaaacttgagccatgtgactaattatttgttttatctaccaaattcaga
ctaagaagtgtattcaaagtgcagttccatatgttggtcttggacttttatatgcatacctactct
acctctcttggacacctgatacatttcggttgatgtttgcaagtcaatactggctgcctgaggtac
gtctcagactagcacaaacaaaagcttaagctttttactcgttaaaattattaaacattttgggaa
atttttttgaggtaaaagtgatgatttggtccatctttggctcaatatttttattgtgcagtta
tctggtatagctaagatgttttccagtgagttgacattagcttcggcatggattcatttgttggct
gtggatctctttgcagcaaggttcgtaagtgtttgaatgtgcatatacgtcagggtgcctgcagtc
cattaaaattaaattctcacagttaaaccatttttctaattatgcaggcaaatatttcaagatggac
tgcagaattctgttgaaacaaggcattctgtttccttctgtctactcttttgcccgataggaatct
tatcgcatgaaattaccaaagctctaaccacaggtggaagaactgccaaacgcgagatccattaat
gcaaaaatgatcagctgacagagtatccatttcctatgacaaagatagtagaggcttttcttgct
attagtgatttgttttcgag

Fig. 2B

SEQ ID No: 4

>*Daucus carota* variant 2 NXS DNA atggcttccctgtcttgcctctgcagttctcctctgtttcttaaggtacgtgttctgtgtttgctg
ttcatatagtctcaattctaatcatgcttggaaactcgttatgtgtttgctgttcatatagtttct
gtttgtattcgttagattgttagaagatataatataatcctgataagcactcctttcaacatctcg
aggttttgggagaactgatcacttgacataagtgtttgcatgatttattcccagggagggcggcaa
aaccctgatttaaagggaaaactaacccagcagtactacagatcatagttataaataggtatcatt
cagtagaagaaaattatgcaattcagttaagcaattggatcatgaataaaaaaggacggtgatgag
ttcacttttcattgtagtttaggttttggcctttatatatgttgttgtcatagttcttggtattga
actccaggtttcagaaaagaatttcaaattctataagaatcttaaactgaattagttgtacgagtt
atgtgagaagttcaagtttgaatccagtagaagttcaagtttgaatccagtagagtttattcgctt
tgttaattggacatgtttttactaaaggtagtcggccttttgatcaatgatctatctccgtttata
gtagaaaatataacagacttgatgtgaaatttagctaatagtttaaccttgctgtgatttctataa
tagtgaatagtcttcactcttcagatatcttgttggtgataaccttgtttctgctttaacattgta
gaacgacgaatcaagactggctaacaaatcgttattagcctataccagaaaggaccggataacaac
ttattgtcttaatagtgtcgaaactgaccctttagtcgacatccacatagcataaagacaaagag
atggagtttcaaaggaggatcgagggtgatcactggacccaatattcaaagatttgcttgttacag
aaaaagctgtggagtttatgctttatgtaaattcctttttcacaaataactttgattgagaatttt
aatttactatgcataccctaagctgttatccttggtatcttctatatcgagaattcttcttatcct
ttaataaaaaaaattgccatgcgctcaatattgaactgctttttgtgaccttgcagggttgacaaa
tcctcaaattgcaagtagtgctttcaccctgggaactgcagctgttctcccctactacacccttat
ggttgtagctccaaaatctgagctggtaagcctaatatggtgacagcttttactgaattgcaaata
ctacgatccattctgaatccaaaatgttttattttctaatagttgagctaaattactgatatgcct
gatgtttacatgcttcgatattcagaccaaaaaatctattgaaagtggcataccatatgttgcgct
tggtcttttgtatggttacctactctacctctcatggacacctgatacaatgaagatgatgtttgc
aagtgaatattggctccccgaggtgtgtttgaactgtgggaagaacacgcggtttttctaattgca
gaaatactttgtttaaaaaaaatttaattaacatatttacattctgacagttatctggcatagcaa
agatgttctccagtgagatgacactagcttctgcatggattcatttgttagctgtagatctctttg
ctgcaaggtccgtttctctccctcatttcccgcgagccttaactcttataccatgttaagtgacca
attctcccaaaatttcaagatgttgggggaggggcttacgaggatcatatttattctaacagttc
taacatttgacgtattgtgatcctattaatcaggcaggtttatcaagatggactggagaacaagat
cgagactcggcattcaatttccctctgcttacttttctgtcctataggaattatatctcatgtagt
caccaaagcactaaccaaaagtacagagtaatccagtaagtagcaagattcacttgtgcctaaagc
atgcttttcatttgactacagaagtacaatgtttgttactgcagattccctggttttgcatttcac
aattttagtcggcttttccatgatatattgctcacaattgctaacttctga

Fig. 2C

SEQ ID No: 5

>*Cichorium endivia* NXS DNA atggctttctcttcttgtctttgccaccatcaattggcactcaaggtattggttaatttcccttt
tactctctctatgtgtgtttgcatatgctcaaacgacttcactttcacgaattcatggtttatttg
gcatttttcgatttgggtacgagtcatttcgcgttattggtactaaatctggttgatttgccgat
ttaactaccggtgtcatccaatttgtgcattttcacatgtttttagctacctcacttttacatatt
cctgtttgtttgcgaatttactatctgggtgtgattcagtttgctgtgttcgtgttaatttggttg
ttttggctcatttgattctgtttattacatccatttctgtattgtgtgactgcagattgaatcatt
cactttagatatacatattatgctgtctgtaaatctattcgtttgtatcttctccccaattgaatt
ggttcactcttccgattttgagttcggttagcagtttagggttcatagatgtttatgttcaaatta
gaaccatcaaaaggcttacatgagtgagaaatcttgaagatgttatatctttgttgcagatcaacc
tcttaacgagtccatcgaaacccacattcgttcttaaagccatgaacaccgaattttacggaatac
atatcggaagcaagatagaaaatcaatggagttttatgaaaggatcacgagccataatcagaccga
accctggaagcttcaatctgcatcaaaaaagctcaaaattgcaagcatcatgtaatcctttcgtat
cctttcgtttatcatgagataatttagcgattaaacatccaaaactttgttaatcttatcgtgtttt
agttcgattggatctttttttcatgtagggtttgcgagtatgcatttagcgagcgatgcttttacat
taggaaccgctgctgttcttccattctacacccttatggtcgctgctccaaaatccgaattggtaa
ggtttacaatgttgtcataaagcaaagaaaattaaaaaaaaaaaaaaaaaatcattcaaatacctta
tctatatatcaatataattggaatttaagtgatgtttctttttttactcatttaaagtgttgaatgg
ataaattggttttttttttctttttgggtaaagtgtcgaatggtctaatattaattgtttaatat
taattgtttaatatattaagtccattaagtgaaaaagaaaacagacgctaagtgtttacaaatttg
gtcgacattaatgcagacgaaaaagtgtatgagaagtagcataccgtatgtggtactcggggtttt
atactcgtatcttctttacctctcgtggacgcccgacacaatccgattaatgtttgcaagcaaata
ctggctgcccgaagtatgattttacaccccctatagtttgctagatagccaacttttaaccctagtg
atggttttatttgcagcttcccggtgttgctaagatgttttctaatgagatgacattagcctccgc
ttggatccatttgttagcggtcgacctctatgctgcaaggtaggaggacatttacgtcttttgcac
aaacaacaaatcggaagctagtccatgtcccaccttcttcggtgggatgaaaaattgcaatttttc
tcccattgacttctgtgtacctgtacctgtacctgtacctgatgaattgtggttttgattggtgga
aacagacaggtgtatcatgatggattggagaaggagatcgagacacggcattcggtttctctttgt
ttgttgttttgtccgattgggatacttgttcatgctatcaccaaggctttgataagtacatataga
gaatcaaaaacagagattcattgatgggtttttttgtgccattaagtcttaaagcatttatgttat
cttttaatctaatcgattatggttttggcagaaatgtttacaagggttggttatgtagacgctgtc
atagggttttattatagcattggcataattaatgttatgcgactataa

Fig. 2D

SEQ ID No: 6

>*Solanum melongena* variant 1 NKS DNA gatgaactgctgggcaccagcctcggtgtcattgagtacccgcagaaaccacactgcctttcttgc
tcttagagaaattataagtcaacgtattggtggatttggaaccaagcttagcagtggagggagttc
tctgggaggatcaagagtcattattcaactaaatcttcaaagaactctttcgcaaagaaaaagctc
tagggtgcatgcttgctgtaattactttcttacaaactccattctttgtgataaaatatctctggt
tttgaatgtttatgacaaagtaatcttaaatgtgtgcttaattaagttctcgctgtacttaagatt
tatcgtctcatccattcccccttttttttggttgttgttgtttatttggagagaaattgtttaaaa
agctactactatttttgcctttagttttaatgaattataaattactcaagtctaaatggtgctttgt
gcatagttaagagtaaaacttgctataggtgctttaagagtaatcttcttcatgcagctgttaatg
ttccttgacccttctgtacagtttagcctctggttttggcagacttttatgccaacgactaacact
ggttcagtttttagctaagtttctatattcttttgcagggttgccaagttcagaaattgcatctac
tgctttcacagtgggaacagcagcagttcttccgttttataccgtcatggttgtggctcctaaagc
tgaactggtaagatttctatagtactttcagtctgaactccttaagcgattccttttctagtgtac
tagagatcaaacttggcactcaaattatgaattcaaaagaccttaaacacttatcagcttcagaca
aagtagaacagttgggcacaacttcagtccttttatgtatatggaagtcactgctttatttaaaag
agaaattgtaattgaacataatttcgaatgcagaccagaaaagcaatgaaaagcagcataccctac
attgtgcttggacttctatatgcatatctattatacctctcctggacaccagatacaattcggctg
atgtttgctagcaaatattggcttcctgaggtctgtgctcgactacataataatttgtacaaattg
catggtcgggatcttaacacttcctttcattcagctgtctggtatagctaagatgttttccaacga
ggtgacgttagcttctgcatggattcatctgttagccatagatcttttttgctgcaaggtcaatctt
taggcgtctttatctttgttgggctatgcccctttgctttctttttgggacaacatgaggaggatg
ccactgttagacatctaactagagtatctcacttgaaacaggcaggtttatcatgacggattgcag
aatgatattgaaacccgccactctgtgactctgtgtttgctgttttgccctgttggaattcttact
cactgcatcaccaaagctctaactagcagcccagaaaagaaacagcataggactc

Fig. 2E

SEQ ID No: 7

>*Solanum melongena* variant 2 NKS DNA tctacttgcttttgtcactctcaattctcactcaaggtgtgccttttctgcttctcctctattcat
agcttgtaatatatgttcttcttcatttgtctaggtaattaaattggtgtttattgttctcaattt
ttttaattgaatacccatacctggtctgtatgttcaactgacacacaactgtttgtttagatctga
agttgctccattgctatatgataatgaaaaattcaatttgagagcacctaaaatgctagtgaaggc
ttcaggtagatactgcaatagtggagctagcattttcaccaagggtgttcatactttagaacata
tgggtgggtgggtgatttttgtatcaaggtatatatataaaaatatttatattttgaaaaagtttt
ccaacgaaagatggttcacccttgggtgaatgtagttcgcccoctggtagatagtgagcaacatct
atgatttaaagatgtttttggcaatagagggtggggatggtggttttagtgaattgaatgtcaatc
tggcaccattgaattatcacttgttcgttgaattatgctatgagaaataaggcttagtgaatggca
tttcatgctcaacacatattcgataaaattaatttatacttggtagttgaaacaaaaaagaaagaa
agaaatgaggttttctacgcactaaaaatgaccaagtttgaaaatacaatgaaatgtcattcctg
ctgaacgactatgctacttaccttagatggaaagctggacacctgctctgtcatcaaatatccgat
gttatatcaggaggaaccagtttccatcctccatgcttaaaacaataaattctgacctttcaagtc
aacaagttcaggaacgaggaaccaagcatagcaatgggtccagtttcctcggaggatcaagagtaa
tgcgtcagcctaacctccaaaatcttccacaaagaagaagctgcagggtgtctgctatgtgtaatc
ttttcttcgctgcttccttagtctttatcatttattttagctctcattctgtgtcttgctacttt
ctttttggataattcttgggaatcagctatacacagtcaggaatctggttatccatcttaatttac
agtcatcacataatgttgcgaattaggttattatgacacctccctgccaactgctaacacatctgt
tagtttaccacacttgataaaaaaaatttattacaatgcttgttaactttgtacaaatactctata
tggccttttcttaacacgtttggcttaatatccacacctactttcctccttttagatgaaccaggg
aaaacaaattcgaaaaagaaaagaagttgtagaagtacaacaatttgctgtcttccttcatctggt
tgaaactttgatatctcccaccctgagtcacatgttccattggaatcttgtttccctcattacgtt
gctggattttccatctcatgtcaataaagactatgcttacttgctcatgtagatgtgtaaattgct
agtctcccagatcttatcaagtgacagttttgatgtattgtatatggaatatcaaactaaatatca
aattgatctactccatttgattataaatccatacgtatatgtataaatacttatttatgaagcttc
ttattgtttactctctttgcaaatgttgcaagtatcacctatttgaacttttgggacaactgatgt
cttattttacagggttgcctagttctcaagtagctagtagtgtctttactctaggaacagcagcc
gttcttccgttttacaccctcatggttgcagcacctaaagctgaacttgtaagttatctcagttct
gtaaagctacattctattttgaaaattttctagagtaaaccctctgggtgtattttcaacttaag
aagctcttgtttatttttttaaaattggaagacataaaaagtgttacttgcaaagttctctctccc
cgtgtcatgcacaaaagtagaactcggggcatgatttcagttgtattgatttgttatctaattgca
agatacttaatttcgtgcctttccgagatatactgtaatagggcataattaaatacttaatgcaga
ccagaaaattgatgggaagtgccataccatatgttgcgctcggacttctgtacacatatctgttgt
acctgtcttggacaccagatacaatccggctaatgtttgctagtaaatactggcttccagaggttt

Fig. 2F (continued)

gttcttgtgcttagcaaatgatggttgtcatcttgtgctgattctataattagggttgttgacgtt
tcattctgttcagctctccagtatagcgaagatgttctccagtgagatgacactagcatcagcttg
gattcacctattggctgtagatctttttgctgcaaggtctctctttctctcgcacacacactttat
tgtatgtgttagattgttccatgctagttgaggaaatgggtagttgtctccttgttaggtgttgcc
atgttggacaatccgcattttatgagctagtgtttcgggtggtatcagactcatcacactcttggt
ttactcaatgtttccacgcgccagatgtccggtcaagggcatacagggagggtggaggaaggatgt
ttggttgtccgactgttctcgcatgtttgtgtagccagttgtttgcttgctaatcctattgggttg
aggaaaatggaggaaggtgctttgttaaactattctaatgctgtttttatttgaaacaggcaggt
ttatcatgatggtttgcaaaatggtattgaaacgcgccattctgtgtctctctgcttgctttttg
ccccattggaattgttattcatctcctcaccaaagctgtactaagtaatgcggaaaacatagtgcc
tagaactcactgaca

Fig. 2G

SEQ ID No: 8

>*Solanum lycopersicum* variant 1 NKS DNA caaaaaggtgtaaagtagcaccaaggagtaagtgcttaaacaactttccgtccaaatagaggtgtg
tggtcggatttggcaaattctcaactaacatcacaaaatgcaatatattattaacattattagtca
cttcatgatttctttatttgcaccaaactttgagttgcttctaaagctaaaaataaattatacttt
ttgttgcttctgtttttctcattattgttgcaacttcaacaacaataaagcatgtacttctcttct
tcttcccatgtttcactcaaggtatgctctttctttctttctgcttctatgtcttgctctctgttt
ctgttttagctctgatatgtttttttgcctctcaaaagggcctcccacagtcatccactgtttcttgc
tgggtattgatatttagttgagttgtttgatcagtttataagcttgatatttagttgagttgtttg
atcagtttataagcttgaacgaacgccctcgtgatgctttaggaagatattgttagcccacaagtt
agggcttattcccactgaaaaatagtcggtacatattttgattgaatcgatgagaaaaagaaaaaa
gtaataatcttttagtatagaaaaattaggaagtttcccactattatgattcgtagtgggaaacgc
ttgtgtttctagtaatgacgtgggaatagcctcttttcgaaatacaagaagtgtgtacagtgtata
tatgcccactctttccctctgctggcactagcagaagtcctttttgcacagggtaagctcttaggt
tcacattattgagttacaggcaaccagaaatggaaatttacgctaacttcttcgttggaagagatg
ttggcgaaggccacaaagctagaagggcattttgtcatcttaaccaacgtgcacgtgcaatgatgt
gaaatccaatatcttcgtctacaattacttgtcgtaacacgtttctgctctaagactttctctcaa
catatctgtaagcagggagtccgcattcactattaagcctacatagatgtggagattattgaagat
tgaggcactagctaaatgaaggtgttttagatcaatgtgaggtctagcacacctttcggaatagga
ctacaaataaataaggttttgcaatgcattgaacctgaacaagttggaggctacaacgaaatttaa
ctgcttttcacgcagtcatttttgtttatcagtctataatttcatttcctgaaacgaaccattact
tgttgcagatgaactgctgggcaccggccttggcgtcaaaagtccctctgaataccaggagaaacc
agactgcctctcctgctcttagacaaatgaagtctgacctttttaagtcaacgtattggtggatttg
gaaccaatcttagcagtggagggagttctctgggaggatcaagaatcattactcaactaaatcttc
aaagaactctttcgcgaagaaaaagtcctatggtgtctgcttgctgtaaattactttcttacaaac
cccattctttgtaataaattatctattgttttaaatgttcatgagaaagtagttttagatgtgtgt
ttgattgagttattgctgcagttgggaagtattgtctcattcattgcccttttttttgtttatctgg
agaataagattgtttttaaagctaatcttctgtacagtttagcttctggttttggcagacttttat
gccaactactgacattggtcaagctttttagttgagtttctatgttcttttgtaggggtgccaagtt
cagaagttgcatctactgctttcacagtgggaacagcagcagttcttccgttttataccgtcatgg
ttgtggctcctaaagctgaacttgtaaggtttttaagtactgtcaatctgaacttcttaaggatt
tcttttccagtgtactgaagattaaacttccactcatattatgaattcaaaagatttttctaaatt
aaacacttaccagcttcagacaaagtagaacggttagggcacaacttcagtccttgtcttgtgtat
atgaaagtcattgttttatttcaatgagaagttgtaactgaacataatttcaaatgcagaccagaa
aagcgatgaaaagcagcataccctacattgtgcttggacttctgtacgcatatctattatacctct

Fig. 2H (continued)

cctggacaccagatacaattcggctgatgtttgctagtaaatactggctcccggaggtctgtgctc
aaccacataataatttgtcaaaactgcattatcgggatcttaacacttcctttcattcagctgtct
ggtatagcgaagatgttctccaatgaagtgacgttagcttctgcatggattcatctgttggccatt
gatcttttgctgcaaggtcaatctctaggcatcttatctttgttggcctatgccccttcgttttt
ttcttttgtataacatgaggaggatgccatagttagacatctcacttggagtatttcacttgaaac
aggcaggtttatcatgatggattgcagaatgatatcgaaacccgccattctgtgtctctgtgcttg
ctgttttgccctgttggaattcttactcactgcatcaccaaagctctaactagtagcccagaaaag
aaacagcataggactcattaaccaatgttttaggccttcttatgttatccgtaaatgatcagccag
cgcgtgaacttatgagcaaagtgtaaaggttttaagtcaatgaatacataagctatttcaataact
tgtttctaagatggatgaatgtacaagatttcttcctttagttccactccaaacttctgatttact
gcatccttaactaagcgtatgagctcaagcatgtcttgagaagttgcagaaccacaatttatgaaa
aagttggcatgcttgtttgagaccatggctccaccaactctcaacccttcaacccactttctct
atcaattctgcagcagaaacacccatagaa

Fig. 2I

SEQ ID No: 9

>*Solanum lycopersicum* variant 2 NXS DNA taaacgtgagggaccatttttgtcatttaatttggtaaaattttagttgtatttgaagtcggtctg
tttcactcttatatgagaagagaattcatcaagagggccagggctcatgatttatcattctgttgg
tgaaacctctcattactgtacttgcaatgtttaattttattttccagatgccatttttgctataat
tcttattgttgttgctcgcaattctcacacccatcaaccatggccttatcttctacttgcttttct
cactctcaattctcactcaaggtatgccctttctctgctactctctattcatagcttgtaatataa
gtttttcttcattaaattgctgtttattgtttgttctcagtttttttaattcataccccgtatgta
tgttaaactgatacacacattatttgctacttgtactgtgtggttagatctgaagtttctccgttg
ctatatgaatacattgaaattgaaaatgaaaatttgagagcaattaagatgctagtaaagtcttca
tgtagatagtgctgagcaactatctatcatttgaagatattttggcaatagggagtgtttggaaga
aaaaactttgaagaatgaggtgctagtgtttggaggtttagtgaattgaatgtcaatcaggtaccg
ttgaagtctcaatgtcatttgaattatgctattagaaattaggcttggtatattgcatgccaagca
aatcttcaataaaatttatctatacttggtaacggaaaaaagaaaatgaggtttccaactcacta
agcactaacgagtttgaagctacaatgaaattccaaacctgctaaactattgttttattagaagta
atcaatctctactacttactgtagatggactgctggacgcctgctctgtcatcaaatatcctatgt
tatatcaggaggaagcagcctccatcctccacacttaaaacaataaactcaaacctttaagtcaa
caagttcataaacgaagaaccaagcatggcaatggatggagtttcctcggaggatcaagagtaaag
tgtcagcctaacctccaaaatcttccacaaagaagaagctacagggtgtctgctatgtgtaatctt
ttcttccactgcttatctttatttctcaactcgtgtcatgctacttccttttggttcttttggat
aattcttgggaatcagctatgttcggtcaggaatgtggttatttacagtcatctcataatgattcg
ctttaggttattatgacacctacctgccaaaacatatgttaatcaacaaactgaattcaaaaaatc
tgttacaatgcatattaactttgtacaaatacttttatgtgcccacttggcttaatgtccaaacct
gttatcctcctattagatgaaccaggaaaaacaaattcaaaaagaaaagtacttttagaagtataa
caatttgctgtcttctttcaatctggttgataatagaaatatctcccaccttgtccaatgttccgt
tgaaatctcgtttctctcatttcgttgctggattttctatctcatgtcaatgaaagaatattctta
cttgctaatgtacatgtgtaaactgctagtgtcttacattataccgaaagacagttttgatgtatt
gtatatggaatatcaaactgaatatcgaattgatctatttgattataaatatatatgtatataaat
atttatacatgtttttaagcttcttattgtgtactctctttgcaaatgttttagtgtcatctatt
tgaacttttgggacaactgatgtcttatttttacagggttgcctagttctcaagtagctagtagtg
tctttacgctaggaacagcaggcgttcttccatttacaccgtcatgattgcagcacctaaagcag
aacttgtaagtaatctcagttctgtaaagcaacactgtttttttatttctagagagtatgccct
atggatatattatcaacttaggaagctcttgtttatttcttttcttggaagacataaagaaaagtt
acacatgccaagttctctctccttatgtcatccacaaaagtagaagtcatggggcataatttcagt
tgcattgatttgtgatctaattgcaagatactgattttgtgcctttccaagatatattgtaatata
gggcataattaaatacttaatgcagaccagaaaattgatggatagtgcaataccatatattgtgct

Fig. 2J (continued)

cggacttctgtacgcatatctgttgtacttgtcttggacaccagatacaattcggctgatgtttgc
tagtaaatactggcttccagaggtttgttcttgtacttaacaaatgatagttgtcatcttgtgctg
ataccgtgatttaggctgttgacatttcattctgttcagctgtctggtatagcaaagatgttctcc
agtgagatgacattagcatctgcttggattcacctattggctgtagatcttttgctgcaaggtct
ctctctttctatctcaaaaccacacttcattattgtaaatgtgttggattgtccgtgttagttgag
gaaatggccatttgtctctttataaggtgttgacatgttgcacaatcctcatcttatgagctagtg
tttggagttgtgttggagccaggcgtaatatttggttgtcctacactagttgaggaatggactgt
tcttgcctcatataatcttggccatttctcaatttatgagctagcttttaagattgtttcagattc
aaggccatttcgttaacagtatgtttgtgcagccagttgttcttttctgatcctattgggtcgagg
aaaaaggaggaaggtgccttgttaaactattctaatgctgttttttatttgaaacaggcaagttta
tcatgatggcttgcaaaatggtatagaaacgcgccattcagtgtctctctgcttgctattttgccc
cattgggattgttattcatctcctcaccaaagctgtactactaagtagtgcagaaaaaacagtgtt
tagaactaactgacagagattcaacaattgtttcctgttaacgactaatgtaattgtgaacaaaag
ggtaatcttcattcaactacgtaaagtgtgcaaatttgtatatcattgatccaacactgcttgaag
cattcgaattgatgagctctccttatatttttcagtaaatctaaattcttttagatggccgaatg
tcagttttctttcttggatcgttactcctgccaaataaagaaaacgtttcttcttctccaatccaa
ttactgataggatgcaaataagaatttctcctctcatatttgccataaacattgcctataattgac
ttctaagtgacataaagttgaaatttgttctaat

Fig. 2K

SEQ ID No: 10

>*Capsicum annuum* NKS DNA gataccctcttgatagtttaggttgatattgttaacccataggttaagggtacggacgtgtaaata
acctctttgcaaaatacagggggagtggggcatatattgccccctcttccttctgccggcacaag
aagagatagtttgtgcacagggtaagttcttagaggttgatcttattgagcaacagacaaccagaa
actggagcttacgtgaacttcttcaaggaagagatgttgcagacaaagggcacaaagcgaggtatc
tattccttgaggaagaagggcatttatcatctagacagacgtgacacgcataatggtgtgaaatc
taacaccttcatcttcgatctctcgtagcaacacattttcagagctaagaatttctctcgacatca
ttctttttatttaagtcattaatattacaatctggaagcagggagtccgcattgactattaggcct
acatagatgtaaagatatttgaagattgaggcatgctagtgtctgaaggcctagcaaattgaaggt
ccattagatcaatgtgaggtctagcacaccttccggaataggactataaagaaataaggttttgca
acacattgaaccctaaacttggagggtacactgaaattcaactgcttttctggcggtcatatttgt
tttacccatctagaatttcatcatctgaaattaaccattacttattgcagatgaactgctggacac
cagctttcgtgtcaaaagtcccgctgaatacctggagaaaccagactgcctcccttgctcttagag
aaatgaagtctgaccttttaagtcaacatattggtggatttgaaaccaagcatagcagtggaggga
gttcactggcaggatccagagtcactattcaactaaatcaccaaagaactctttctcaacgaaaaa
gctttagggcgtctgcttgctgtaattactttcttacaatctccatttctttgtcataatttatct
ctggatttgaatgttcacgataaagtagttttaagtatgtgctttaagttattgctgcagttgggt
ttagtagtctcatcaatcgtcttctttttttttatttggagaataaaattgcttaaaaagcgcatat
tttgtcattagttttaatgaattataaagcactgaagttccaatgatactgagtgtaaaataaatt
agagttttaacagtaatctcccttcatgcagctattaatcttccttgatccttttgtacagttttt
cttattttggcagacttttatgccaactactaacattagctaagtgtatcactggcaagctcttag
ttaagtttcttattcatttgcagggttgccaagttcagaagttgcatctactgctttcacagtggg
aacagcagtagttcttccattttataccatcatggttgtggctcctaaagctaaacttgtaagatt
tctaaagtgcttttactctgaactccttaagcgatttcatttccagtgtactggagatcaaacttg
gcagtgaatttattaattcagaaggcgttcttaaattaaacactaaccagcttcaaacaaagtaga
acagttggtacacaatctcagtccttatgtatatgttttccattcagtgctttagtttgatagtat
tgaattataacatgctgatttggcaaaagatgtaagtcattgctttatttcaaagagcaagttgt
aactgaaaaaatttcaaatgcagaccaaaaaagcgatgaaaagtagcataccctacattgtgcttg
gacttttgtacgcatatctattatacctctcttggacaccagatacgatccggttgatgtttgcaa
gtcaatactggcttccagaggtctgtgctcaactacataataatttgtacaagttgtatggtcggg
atcttaacacttgcttccattcagctgcctggtatagctaagatgttctccaacgaggtgacgtta
gcttctgcatggattcatctgttggctatcgatctttttgctgcaaggtcaatctctaggcatcta
tctttgttgggctatggccctttgatttctttttgggacatcatgtggagggtttcacttttagac
atctaactagagtatttcacttgaaacaggcaggtttatcacgacggattgcagaatgatattgaa
acacgccattctgtgtcgctgtgcttgctgttttgccctgttgggattcttactcacttcatcacc

Fig. 2L (continued)

aaagctctaactagtagcccagaaaagagacagcgtaggattcattaaccaatgttttaggccttc ttatgttatctgtaaatggtcagccagcatgtgactatcagcaaagtgtaaagattttcagtcaa

Fig. 2M

SEQ ID No: 11

>*Brassica oleracea* NXS DNA agtttctgtcaaagagttcgtgaatcgaatcggagatggctttttctcagcctttgtcttcttcgt
ctctctcggtatttcgcttttttttttagtttactccaaaatatatacatctgtaattattgtatat
gttcatgtacacttgtttgatattgtccgattagtttctgtgtcgagctttacttactagtactca
tatagcttagattccttatccttaagaatcaaatcagccaatcgatgggttcgcttgagttcactt
gccctgtctctgtctgaaaatttcagattctgtgagttaaagtcgttatcaagtttttgttttttg
ttttttaatcagattagattcatttttttggtggtacagatgacgaatcggagctttgtagctaag
agctcggtgacagcaagtctttctcttaacaagtctttaaagattcgattccataatcgttggagc
ttcgacggaggatcaagaatcgttctgttccccagtgtatcatccgattcgtcctcccttgttcac
aagaaacgctcctgcgtacgagcttcatgtaatgtctcttttaactgaaaacattgaagcctcaa
actttgtcgagagattctagttagctcttgtgatttcagactaaaaacatgttgatgttcagggat
ggctacgtctcaaatcgcaagcagtgtatttgctgtcggaacaaccgcggttcttcctttttacac
tctgatggttgtagctcctaaagctgaaattgtgagtcccttttctttgttgcagtcttacaacttc
ttttgcagaactaaagaggttcatctgaaattgactttttttttcaagaaagaaattgaatatatg
tgtttctttcagatttacaaaaaaaagtgtctctcttttgtgcagaccaagaagtgtatggagagt
agcataccgtatgtcgtcttaggcgtattatacgcgtatttgttgtacctttcttggacacctgaa
acgctcaaatacatgttttccagtaaatacttgttgccagaggtttgttttcaatacatactgtat
aacaatgtttcatagtagctactaaatgttttcctctctctcttttctttggtcatttgcagttgt
ccggaatagcgaaaatgttctcaagtgaaatgactcttgcttctgcttggattcatcttcttgtta
ttgatctttttgctgccaggtatgttacaatttcaggttttggtttcaatcaaaagtctaaaaaca
tgtttcttataacacatgttttgtttgtttctatgcagacaagtttttaatgatggcttggagaat
aagatcgagacgaggcactcggtttcactttgccttctcttctgtccggttggaatcgtttctcat
gtggtaaccaaagctttaaccaacagttctacatccaacaccaacaaccagtgcaagtaaactgat
cattgtggctggtctctcatcactgtctttcttaactgcttataaagattttgattg

Fig. 2N

SEQ ID No: 12

>*Apium graveolens* variant 1 NXS DNA aactcatatctttgtccctgtctacatacatatgatatatagatatgtttatgaccaagttgtctt
tatgactttttgcaatgacctcaggatttctttaattatgtctactaccagacatatatgcatat
gaatgtcaagagtgaattgaagaattgttggtggatttgggtatttgttatgatatgtctctttg
ttttgactgatctgcggtgattctgcaattcttcttctcagtttgtattgtcaattggtgttctt
tttaaggtggaatttgaataaccagtaggttgaaaattctaccaatacattatgtgctggactgat
catttcattcaggacttgcggatgcaattgttgaatccttgttatttctaatcaatttttctccat
agccctcatgcctaagtgaaaaaaaaaactcaatttgttatgtgaaattcaaaatgtcccttttgt
ttcaatcctgaagtgggaatgcagttgccaagctgcgcatgattgaatcttttagaatccccata
tgctgatatagaaactgaatgattagttgattaataatattttcttattatttggtattgtgatcg
ttcgttggttctttatttataacttgaacttgaacatgaactattacttaacttcatttctttcct
tgtagaccgaacattcaacattgagtacgaagcccttatgtaacatcggccagagtcggctgaaca
ctgttgctattgaaggtataaacagcgacctttatggacaacatctggttctttggacaaagatga
gaaaagaatggagtttcaagggaggatcaacatctattgctgttcctactattcaaagatctgttc
tttacagaaaaagccttgaagtgcaggcttcatgtaagccccctatatttgattcctctaagcacc
tcaatttgtttctaaagctgagtagttaccgcaagttcttagagttaatatcattaattttgttct
atgcgacaattagtcgtcagcatctatgatcccttacaaataaatttatctagatggccaatgata
taaatctatgtaacagtgtgaaatgatgaactggaaacaaagctttgatctgatgtaattttggcg
caaggaatgatcttagttgtttgataaaggcagttaatgtgaccgacatgtagatatttttattct
aagcaactggtggaagttagttaggaacctagtaagggctaattgtgctaaattacttgctgttgc
ttaacttgatgtgtacaaattgttgctaaaattgaaatttgcaagtctgtagcattttgactggct
gtcttctcactgtgaccttgcagggtttacgaattctcatattgcaagtagtgtttttacattggc
aactgcagctgttcttccattttacaccctcatggttctggctccaaaagctaacctggtaaaaat
atttgttggaacatggtgactgctttgactggatctaatgttctacttcatatacataaccagatt
tcaacctcttaaataattacgccgagtgactaatagtttttcttttatactaaatttagactaaaa
agtgtattcaaagtacacttccatatgttgttcttggaattctgtatgcatatctactctacctct
cttggacacctgatacatttcggttgatgtttgcaagtcaatattggttgcctgaggtgcgtttca
cacaatcaaaaaacaaaagcttaggctttcaacacctagtttttattctgaaacaatttggaagtt
gtttttgagatgaaacttatgattgtggtccatcttttgctcaacctttaaactgtgcagttatcg
ggtatagctaagatgttctccagtgagctgacattagcttcggcgtggatccatttgttggctgtt
gatctctttgcagcaaggtctgtaagtgtgtgcatatgtgtgattctttttgcagtgtattaatat
aaatttctcacagtagccgttctgttctgcaggcaaatatttatagacggactgcagaactacgtt
gaaacaaggcattccgtttccttctgtctactgttttgtcctataggaatttttatctcatgaaatt
accaaagctctaaccacaggtggaagaaatactaaacgccagattcgttgatgcaaa

Fig. 2O

SEQ ID No: 13

>*Apium graveolens* variant 2 NXS DNA ggtaagtgtcctgtgktcatatagtttctattctaattgcgttttagtttgtagctatttttcttt
cttcgtttgtctacttgattaaatcttgtgaaggtgaattcaagtcatatttaaaaaaattgaata
ctaagtagaattattaagtactttagtatttacctttctatctatgttcatattgctctcttggat
cctagttggatattatgtttctatttgtgttcatcaagaaagtgtttgcatgatatatatttttgt
acagggtggcaaaaacccaaacttttatgcgaaaatttcgaaaaactgtatacagatcatcacagt
cagcagtactacaaatcagtagtttcaaagttacaaattaactggaggaataatacaagtcattta
aacagttggatcatcaataatagtggagtgtgatgatttaatctttttattacagttctggtttt
agcctattgatgatatgttggtgtcagtttgtcgattgaagttttaagggtcaagtctactggaat
ttgtatgatatcgactactttgtaaattgaaactctggggttcaaaaaagaattttgaaatttgaa
ctctaaaatgattttaatctgaatcagtttaccccagttgatttgctttattggacatatatattt
actcaaggtgtttggactttgatctatccaatcctatatagtacaaaaatatgctgaattttacct
ttaaagcgattgcttaaatagcgatccttatgtatccctcagatttttttgtctatagttaagttc
ttgtttcacaggtgaccctggaataaggatgctaataaccttcatgtttctgctttaaaactgtag
aatgacgacctaagactgactaacagattattagaagcctgttttagaaaggaccagttaacaaca
tgtgctcttaaaagtttcaaaactgaccctttttagtcgacatccaccaagcataaagacgaagagt
agaactgaatggagtttcaaaggcggatcaagggcaatccccggaccaaccattcacaaatttgct
cgtaatagaaaaagctgtggagtgtatgcttcatgtaagttcattttccagaaataatttgatagt
aaattttaatttgctatgcatatcctaagttgttatacttggtatctttttctctttgaatttgttc
ttatcctttcatatacaattgtcaagtgttcatgatctaactgctcttttatgttgcttgcagggt
tcacgaatcctcaaattgcaagtggtgctttcaccctgggaactgcagctgttcttccatactaca
ctcttatggttgtagcgccaaaatctgagctggtatgcttctatcaccaaatgcggtgacagcttt
tattgacatgcaaatagtaattaggcccaatctgaaactaaagtttttatttctgaaaattgag
aaaaacgactgatatgcatgtttacttgctccaacaatcagaccaagaagtctatcgaaagtggca
taccgtatgttacgcttggtcttttgtatggttacctactttacctctcatggaccccctgatacaa
tgaggctgatgtttgcgagccaatactggcttcctgaggtatgtttgagtagcttgtgggaaaaaa
atgtggtttttccatttgtagaaacgctttgttgttaaatgaatttaatgaaccaaattatgttgt
tacagttatctggaatagctaagatgttctcgagtgagatgacactagcttctgcatggattcatc
tgttagctgtagatctgtttgctgcaaggtttgtttctctccctcatccatgtgtagctttgtggt
gggagacttgccaagttctaacgtttgacatttctcatcctatcaggcaggtttatcatgatgga
ctggagaacaaggtcgagacacggcattcaatttccctttgcttactcttttgtcctataggaatt
atatctcatgtagtcaccaaagcactaaccaaaagttcaaagtaa

Fig. 2P

SEQ ID No: 14

>*Spinacia oleracea* NXS DNA gaatggggcatgaaaacgaagtgatgacaaaagagacagtggcgcactgtcatccctcccatctt
ttcttccttcaatggggaacaaagttatcttccttctttagtagtgatgatgatgtcaaatcaatt
tacatctaaacctaatcatcaacataaattcagtaattaagcattgttcattcattatactttctg
ggtcttttggaatttctgggtgtttttttgagctcttctggtatggctttatcttcatgctttgcct
atcatccccagatctcttccaaggtacccactcttttttttctcttcaattctttttttccaataaca
atttgtccaaattttgtgagtatcaaattgtttctggtttatattgagctcaaaattttgatttga
ttgcctttatattataaacgtgtgcatagttctgctggatttcatctgggtattgttcaaattaat
tgattttagtatatctttgtcgttgttttcttcattcatgtgtatttgtctgctggttaaaaaaaa
cagaacaaacacccataagtctgtaatttaccagcttatacgaatctggaaatgttaaaaaatgca
tgttttgatgttctgcaatctgcagtcaatcaagttcatcatgatgacactggttaatggattctg
cgcgaatgatttgatcttgtccatttttatgaattaaggttgtttgctgtagattgattgcagcgt
tctagtagataaaaaccatcatcaggtgggtttaagtccgagtttagttctatctgttcaaggtgt
gagaaatggaatatttagccagaaagtgcctaagctcagagcggagataatgcacggttgttgttt
ccttggaggtcttagaattgatattagaccgacagtaaacgaatccaatttttcgcgtaggaattc
tggagtatgttattcttgtaagccttctcgtctttagcctgaaaatcttaggtttgaaggttcttc
cttttaagttataacccattacatcatactttgtactgcttatgttatttcagggttgtcgaatac
tcaagttgctagcagtgcatttacattaggaacagctgctgtcctcccatttacactctcatgat
cgttgctccgaaagctgaacttgtaatcttctcagaacttactcagcaataataatgatacatcaa
gtttgttgatgtaacagtcgtcgttatttcttgtatgtatgaatgaatgtaaactggattactgca
gactaaaaagactatgaaaagtagcataccatatgttgtgctagggcttctgtacgcatatctttt
gtacctttcttggacgcctgaaaccatacgcttgatgtttgcgagtaaatactggttacctgaggt
tagtttgtttagcatcaactgacatattcaattatgaaatatgaaactaatttcatattcagtaat
ctgcatttttatggatgatatgcagcttcaaggtatagcgaaaatgttttccagtgagatgacttt
agcatctgcatggattcatctgctggtagtggacctctttgctgctaggtcacttcctactcaagt
caagaattatggtattctgttagaatgagacactgaattcagaagaaaaaaaaaactcacaaaatc
ctatatattttctgaacaggaatgtttatcaagatggtctggagaaggaagtcgagacccggcatt
cagtctcaatgtgcttgctattctgtcctgtaggaattctaagtcatctcatcaccacggcgctga
ccagaccttctgacaaaactcgacatagcgatactattatctaatttttctgaactagagttttaa
tctgtttttttgtgaactgatgtttttggttggatgtgccaaggaagttgctgtcaaatttaaatgaa
acaatgcatatagacaataattagccataagagacacttagagaaaaacattagcactgaatagtt
ttcttgtcatgaattgatag

Fig. 2Q

SEQ ID No: 15

>*Valerianella locusta* NXS DNA cttttgccaccctcaattctcactcaaggtaatcatttaatgctttctttactttgtttgtgtag
ttttatggtttttgatgttcttgattcatacccatttctcaattttgcctaattgtgaaatcttt
gaggagttttgattggatatgggtagttttgttgttttcttacaaagaaaatgtgaattttggca
ctttattgttctgggtttgtgctagatctgagaatacttcttgttaattgttcgaatttatgcgag
aatttgagtaatttggagctagtttgctttcggtttgactaatttagtgtttgatttggaaaattt
ggacattttaagctttaaaggtaactttctaaaccagtttatagagtcggtcaataaattcattat
cggtgatgtgtcagcatcctattggataattcacactccgtatgatcagcaaaaagtgtcactgtt
gattgtttgatgcattgggtaattgtacattagatcagagtacaaccctttattgcatacaattag
tttcagcttttgacattgaacttgtatatagaagagagttttactgtcatcaatctagttagctgt
atataatccctaacatttagagcttaatttgtagatggattgctcaatatcgactgtaaaatctt
cgtatattacaagaaaccaaaaacaactgacaaatttactctcgggagtacgaacggtcaacctt
ttggtcaacatttgcgtggaaagaagctaagctatcttgtgggtcgagtttctcaggaaggtcaa
aagcaatcgtttcatcgaaccctcgaaaacttattcacttcagaaaatactgtcgaatttacgctt
catgtatatcctttcccacagaactttgaatatcaaacttttgtatgaagtttgttaaatcgtatc
ttttgcagggtggtcgaatcctactacaattgcgaacaatgtattcaccttgggaaccgttgccgt
tcttcccttctacacactaatgcttgtggctccgaaagccgaactggtaaaacctagtcgaattac
tctcaagtttagtacagtaatttattttttcttgctttgactaaaagattgtaatctgaatgcaga
cacaaaaatcgatggaaagcagcataccgtatatcgtgcttggagtattatacgcatgcttattgt
atctgtcgtggtcgcctgatacattacgcctcatgtttgcgagcaaatactggcttccagaggttc
gtcatttgaataaaatgctaatttggtgtttatatgttaacaagggcaaaacagtcatatttaaa
gtaattagattcagattagttataacccgtggtagattaacagttcttttaaattcagatagcaga
ctttcgtaaagttttgttgagattccaaattccaaaccatcatacactatcttgcacttaaattga
ccttttcggtgtttcagctgcccggtatagctaagatgttctcgaatgaaattacattggcttctg
cttggcttcacttattagctatcgatctttacgctgccaggtcacctcctatctctctttctacac
acacatacacataatatataccgagcctttggtattaccaacttagcgtaaaattgggtgcaaaaa
aagggtatctatatgtatatatgtgtctctaatttctttatgatacacacacgcttctttttgaa
cctcgaaaggcttatttgaaatacgtattatgtattcacatttaaacacatttttgcacttttg
gcacctgaatatcacagcactttatatttctgacattggtaatctctgttaacaggcaggtttac
aaagatggaatcgagaacaacatcgagacgaggcattcagtttcgatatgtcttttattttgtcca
attggaatcattgttcatta

Fig. 2R

SEQ ID No: 16

>*Rhaphanus sativus* NXS DNA cccttttttagtcagtggaagactcttttaagatttcaagtcaaaaaaaaaaaaaaaaaaagactc
ttttaagatttgttttatttaacataaaaaatgcatttgagttcggtgtagaagctaaatgaagag
ccaatttccctcaaagagttcgtaaagtttgaatcggagatggctttttctcagcctctgtcttct
tcgtctctcatggtatttcgcttttagttaaaaaaaaaaattattctccagtatatgtacatcagt
aactaatgtatgcttatgtacagttgtttggattagattctgtgtcgagcttacttactagttagt
actcacatagttcagattccttatccttaagagtcaaagttcactttccctgtctctgtctgaaaa
tttcagattccgtgacttaatgtcgttatcaagtttttttttttgtttgatttttttttaatcagat
tagattcttttttttttggtggtacagatgatgaatcggagctttctagctaagagctcggtgacag
caagtctttctctcaacaagtctagagtgtgcgttgattctttaaaaattcaattccagaatcatt
ggagcttcgtcggaggatcacgactcgctttctccctagtctttcgacgaattcatcctcctttg
ttcacaagaaacgctcctgcgtacgagcttcatgtaatgtctcttcttaaccggaagatttaagc
tttgaactttgtcgagatttaatatattatgttgatgttcagggttagctacttctcagatcgcaa
gcagtgtatttgcggtcggaacaaccgcggttcttcctttttacactctgatggttgtagcaccta
aagctgaaattgtgagtccttttctgtgtttacaacttcttgtacagaactatgagaggttcatct
gaaattgaatattatatgtgtctctctttttgtgcagaccaagaagtgtatggagagtagcatacc
gtatgtcgtcttaggcctattatacgcgtatttgttataccttcttggacacctgatacgctcaa
atacatgttttccagtaaatacttgttgccagaggtttgttttcaatacaaactctataacaatgt
tttttatatagctgctaaatgttttcttctctctttttttttttccttggtcatttgcagttgtccg
gaatagcgaaaatgttctcaagtgaaatgactcttgcttctgcttggatccatcttcttgttatcg
atctttttgctgctaggtatgttgcaattttcaggttacttttggttttaatcaaaagttgcacat
gtttcttataacagatgttttgtttgtttcttctatgaagacaagttttaacgatggcttggaga
ataagatcgagactaggcactcggtttcactttgccttctcttctgtccggttggaatcgtttctc
atgtggttaccaaagctttaaccaacagttctacatccaataccaataaccagtgcaagtaaactg
atcatcttggttggtctctcaccattgtctttcttaactgcttataaatgtttttggtttgagata
gttcattttgctttagcttcggttaagtcagcagaacgagtttgttgtggatttagttattgaaaa
aaccaaataagaccaaacaacttgagacagtgtttcttttactatttggtagacataattttggat
tccctgatcagtcacagagattccccgtgatctctagctatttagagagtatccaactcctggaa
actcaaaaaaacacacggtcacctaatttagaatactctctaacaacatttgcctgcgatctctag
ctatttatactatagccattataaagaactatgttttaaattgtactagctt

Fig. 2S

SEQ ID No: 17

>*Capsicum baccatum* NXS DNA atgaactgctggacaccagctttggtgtcaaaagtcccgctgaatacctggagaaaccagactgcc
tcccttgctcttagagaaatgaagtctgaccttctaagtcaacatattggtggatttgaaatcaag
catagctgtggagggagttcactggcaggatccagagtcactattcaactaaatcaccaaagaact
ctttctcaacgaaaaagctttagggtgtctgcttgctgtaattactttcttaaaatctccatttct
ttgtcataatttatctctggatttgaatgttcacgataaagtagttttaaatatgtgctttaagtt
attgctgcagttgggtttagtagtctcatcaatcgccttcttttttttatttggagaataaaattg
cttaaaaagcgcatatttgtcattagttttaatgaattataaagcactgaagttccaatgatact
gagtgtaaaataaattagagttttaacagcaatctcccttcatgcagctattaatcttccttgatc
cttttgtacagtttttcttattttggcagactcaatcttccttgatccttttgtacagtttttctt
attttggcagactcaatcttccttgatccttttgtacagtttttcttattttggcagacttttatg
ccaactactaacattagctaagtgtatcactggcaagctcttagttaagtttcttattcatttata
gggttgccaagttcagaagttgcatctactgctttcacagtgggaacagcggtagttcttccattt
tataccatcatggttgtggctcctaaagctaaacttgtaagatttctaaagtgcttttactctgaa
ctccttttagcgatttcatttccagtgtactggagatcaaacttggcagtgaatttattaattcaga
aggcgttcttaaattacacactaaccagcttcaaacaaagtagaacagttggtacacaatctcagt
ccttatgtatatgttttccattcagtgctttagtttgatagtatttaattataacatgctgatttt
ggcaaaagatgtaagtcattgctttatttcaaagagcaagttgtaactgaacaaaatttcaaatgc
agaccagaaaagcgatgaaaagtagcataccctacattgtgcttggacttttgtacgcatatctat
tatacctctcttggacaccagatacgatccggttgatgtttgcaagtcaatactggcttccagagg
tctgtgctcaactacataataatttgtacaagttgtatggtcgggatcttaacacttgcttccatt
cagctgcctggtatagctaagatgttctccaatgaggtgacgttagcttctgcatggattcatctg
ttggctatcgatctttttgctgcaaggtcaatctctaggcatctatctttgttgggctatggccct
ttgatttctttttgggacatcatgtggagggtttcactttagacatctaactagagtatttcact
tgaaacaggcaggtttatcacgacggattgcagaatgatattgaaacacgccattctgtgtcgctg
tgcttgctgttttgccctgttgggattcttactcacttcatcaccaaagctctaactagtagccca
gaaaagagacagcgtaggattcattaaccaatgttttaggccagcatgtgactatcagcaaa

Fig. 2T

SEQ ID No: 18

>*Chenopodium quinoa* NXS DNA atggctttttcttcctgctttgcctttcatccccagatctcttcttccaagattgattgccgagtt
ttagtacataaaatccatcataaggcaggattaagtccaagtttagctctttctcatcagggtgta
agcactgaaatttatagccagcaagtgtctaagctaagacctgatgtaaagcatgattggtgtttc
cttggagggcttagaattgatgttagaccgaaagtaaacaaatttgtgttttcgcggaagaattct
ggagtatgctattcttgtaagatttctcttcttaatcctgaaaatgatggtttgctcaaagcctgt
aacatgtgattatcagtttttatccttttcgagtttataatctcaggttcgacctttaacccaatg
cagcatactttgcttgttatctcagggttgccggatcctcaaattgctaccagtgcatttaccata
gggacagcagctgtcctcccgttttacactcttatggttgttgctccgaaagctgaacttgtaact
tctctgaactaactgaactatgtatgaaatttttcttggtgtaacagtcatcgttaaatagtcta
aatgaatgttacaccaaggaaagtgtttattgtgtgctcttctattatgtgtatgacagtatgatt
actgaatatactgcagacaaaaaagaccatgaaaagtagcataccatatgttgtgtttggccttct
gtacgcttatcttctgtacctttcatggacacctgaaactataagcttgatgtttgccagtaaata
ctggttacccgaggttagtttgtttggcattaacaaattaacgacagattcaaatacaaaactaat
ttatattcacaattttgcattttatggatgatatgtagcttcagggtatagcgaaaatgttttcca
gtgagatgacattagcatcagcatggattcatctgttggtagtggacctctatgctgctaggtctc
ttcttccctctcctctgcttactctagtagtctagattatggtgttctattataatcaggcgttga
ttaaaatctaacacactcctatttgtgaacaggcaagtttatcatgatggtctacagaacgaaat
cgaaacccggcattcagtctcaatgtgcttgcttttctgtccaattggaatcctaagccacttgat
cacatcgtcactgaccaaacctgctgagaaaactagacatacagatactattatctaatttttct
gaa

Fig. 2U

SEQ ID No: 19

>*Fagopyrum esculentum* NKS DNA atggcgttatctacttgcttctcacatgcccggatcttcttacagaatgacatgggcagcaaggtt
cagaggactcagcttaacttcaggttggaaacaagacacaccgtttctcgtcaatctttgaacatt
caacactttgccaaaacccctcagtgaacagagccttggtctaggctgcatgaccgctgctaga
acaaagattaacacgacaagtctgtcaaaaaaaagacctggaatttgttcatgctggatggtaggg
tctcagattgctagcaacgctttcaccttaggaacggcagctgtactccccttctacacactcatg
gtctttgctcccaaagctgaaatgactaagaaagcaatggacagcagcataccgtatgtcatgctt
ggactcgtatatgcatacttactatacctttcgtggacaccagacaccataaagctaatgtttgca
agtaaatactggctacccgagttacccggtatagcaaaaatgttctcaaacgagatgacgttatcg
tctgcttggattcacctgctgatagtcgacctctttgctgccaggcgtatatatcatgacggattg
gagaataagattgaaactcgtcattcagtgtctatgtgcttgctcgtctgccctattgggatcttg
atgcatacaattaccaaagcactgaccagaacacgagttgaaagcagcaaacacaatgtatga

Fig. 2V

SEQ ID No: 20

>*Lens esculenta* NXS DNA gctgaatctgttattcactatccttgttttgcttcaaccatgtctttctcttcttgctattcccat
ttacctttagcatttaataaggtacacttttctgttttcatgtttttcaattctttgcacatgt
tgttttgtaatcttatctgcattttcttgtctttttggtggatttttttgtaccctttattt
taatttgatttttttcaaatggggtttctgtttgaggtttaaagttttgaactttggttaaaaata
tctgaaattgaaagtttttgctttctgtcattgatttgaatcaccaatgcattactaatcaaatg
gccatttgagtttttctttgttgttaatttttgtatgtaatagatctgatgatgctaggtgcat
gttggcatgttgatgataaactatgtagaacaacactttaggttgacggtgtgtctgatattggat
gtgagtcggcggataccgatagaatactgacacacgtagttacattgaatcattctattttctcaa
attatgatggtgttgacgtgtcactatcgtatctggtgttcatgttagtgtcggtgcttcgtaaaa
aacaaatacgggtttgttcaaatagtccttgaatattgagctgtatgattcacctgcacaaactat
gatatttcatatctgagctcaatgtagttcatttattctaattgattgatcatcactgggggcagg
atataaaactctgtaggacagttggacaagagaagctgaattttcctttcactataaggagtaata
gtgttgagctgtgcacccgacgcatttcgagcagtagagccggcttaagtggagattggagtttca
taggaggatccaaaattgtagtaaaacctaaagctacaacatcgtttcgcaatccaaaacgaagtc
aaatacatgcttcatgtaataatctcttttcatgctacttaatggtagggataatggtgacaatat
ttgttctgcatgttcattgttctagctctatgtttcagggttcataggatctcaacttgctagcac
tgtgtttacatggggaacaatcgcggtgctcccgtattacacacttatggttttcgccccgaaatc
cgagctagtacgtttgattagtgattgcaattcacttcattaaaataacatattgatattcttgtt
tttcatttcatttatttggttatgattctgatatcctgattcatttttctgaaatgcaaaattaca
gaccaaaaaggctatgcagagtaatttaccgtatgtaatcctcggcgttctatacgcttacttact
gtgcctttcttggacacctgaaacggttcgattgatttttgcaagtaaatacttactacctgaggt
gagtagtcattcattcatcgatgaagttcagtttctttctctaatgagttcttttatctaactcg
taactgtttatattcgctactccatcatgcagcttagcagcataggaaaaatgttctctagtgagt
tgactttagcctctgcttggattcacctttttggttgttgatctttttgctgcaaggtccggcattt
tatcttcctttttgcgataagatttgatatttggacacaaaaatcagcaacaatttggataaacat
cgttcaaatatatggttaatcgcattcagtgaatggtcaatgaatacaactctaaattaatcatgt
atttgagtcgcattaactctaaattgttgtcgaattttgtgtcaaaataacaactatttctcattc
tttagctatttttctaatagtatatttggttcaaaatccaggcatatttccgcgaaggaatggag
aatcagattgaaactcggcattcggtttcctttttgcttgttcttttgccctatagggattcttact
catgtcatcactaaagcaatgaccaaaactacaagaaaacagggtcatggtttatagatggcac

Fig. 2W

SEQ ID No: 21

>*Medicago sativa* NXS DNA atcatgtctttctcttcttgctattctcattcaccattaccatttaataaggtacamccctttcat
tgttttgttttgtaatcttatctgcatttttttgtctttttggtacctttttttgattttacac
aaatggggtttctgtttgaaatgtaaagttttgaactttgaataaatgtatctgaaattgaaaatt
gttttctgtgatagatcaraatcaccaatgcrttaywaatgtgaaawgggkctttgagttttttt
tttttttgttattttaagtttgtaatagatttgatgttaggtgcatgttggtattaaatatgta
gaattgacacttcacattgatgtcagtgtcatgtttgtgtaagtgcttcataggcaataaaaggga
gtttatattgccgcgtaagtataactcagatggtaaaatgttgcagtgacatttgatatgttaaaa
tgcatgttggtatattgtcgcgtgagtacacctcatatgatagaatgttgcagagaaatttgatat
gttgtggcgtcggttcaaccctcatttcaacttcttagcacttggttggtgtgagttttgccgc
taggttgtttaaaacaaaacaaataggagtttgtatttcaaaaagttggcactcttgtgtcatcaa
accaactttggagcaccgacacttaaaattgaagatttgtccagtgtttagcatgtgtcgatgtcc
aacaccggcatatgcggttacattgaattatttcatttttgagtcaatgtagtttatttattcgt
atgtatggataatctagtgtgtatttctgagctcaagaagttttattctatttcatattgatttat
aatcatttggggcaggatataaaactctgtaggacagttgggcaactgaagctgaattttcctttc
tctatcaggagtgatggtgttaccaaacacatttcgagaagtagattcagtttaagtggagattgg
agtttcataggagggtccagaattgttgtaaaaccaaaagctacaagatcggttcgccatccaaaa
agaagtcaaatacatgcttcatgtaatcctttttaatgctactttttcatgtaatctagaattgg
tgcaatttgtttcttacatataatttaccattcaatagaattggctgtgaaggaatttragcataa
tggatatatttaggttcttttgcaaaaattgttggatctgtaaggatctgatacacaagatgcatc
tctatatttatcttatctttttggcggcattatcataaagtaggttactattagggcatgtttgg
attgacttatttgagcttatctattgatatagagcctagtaagactgtttgagacttgagagaggt
tatgaaaacacttatacatgacatgtgcataagctgttttagtttatttccttaaatgcttaag
atagtttattgaaacagcttatagattatatgaaaacagtccaactttatttattgtttgttata
aaaatagcttagacagaagcacttatatgataagcgtcagctaagctgtttatccaaacagggtct
tgtctttctgagctctattctttttaagtttttggagacaagttatggatgttaacattgctcct
tttgcatgtattccctttctacaattattcatgtggcccctgatctcagctattcgagtttccta
attttctgttattcttttgtatattgtaactttcaaagccttgaacaaacacatttaggtcgacac
cattgaatcgaatarattgttataatatacttgaaaaaacttgattatgatctatgcttaaattgc
ttgttctgtataaatggyggtgattcattgttttacctcaatgttgcagggttcataggatctcaa
cttcctagcactgtatttacatggggaacaattgcagtgctcccgttttacaccccttatggttcta
gccccaaaatccgatctggtacgtttctttctgcatttgagaaaaattatgattagtaatctcatt
ttcacaattcatattcagtttttaggtacattaacaaaaaagcattctgatattcctttttcatttc
atttatttggttatgatactgatatcctgattaatttttctgaaattaaaaaatatagaccaaaaa
gtctatggaaagtagtttaccatatgtagtgctcggcattctatatgcttatttgctgtgcctttc
ttggacacctgaaacagttcgattgattttcgcgagtaaatacttactacctgaggtgtgtattca

Fig. 2X (continued)

ttcatcaacgaagttatgttttctttctttaaagagttctattattcaaactcataaccgtttata
tttgcatactccttgcagctttctagcataggaaaaatgttctctagtgagttgactttagcctct
gcttggattcacctttttggttgttgatctttttgctgcaaggtcctgttgtatctttttgtgatttc
tacttcacccaattttcctcgttattgctggtttttcattcatgaatgatattttgatacaaattt
gcgaacaaaaaatcgagaacaatttggataattaatgccgttaaggtayctggttgatcgwattaa
kkggttggttaatgaatataaktatatgtcacaactcattaatcatccggttaatgcaattaaccc
tgaatttggacgtcataaaccaatggtttttagatgttcaaatatacatggtatccattaatcatc
ccaattatattcatgatcttcaggttttcgaatgcacatgatattctattaaccataatctgttaa
tctgtgttaaactatacacatgatatcgtggttaatatcgtgattaatgacattcaaaaccgtggt
gaattttgttgtcgaatttgtgttaaaataacacagctctttctcattctttagttatttctctga
cagtatttttggttcaaaatccaggcatatatttcatgatggactgaagaatcagattgaaactcg
gcattcagtttccttttgcttgttcttttgcccaattgggattcttactcatgtcatcaccaaagc
aatgaccaaaactacaagaaaagatggtcatggtttatagatggcac

Fig. 2Y

SEQ ID No: 22

>*Pisum sativum* NXS DNA atggttttcgccccgaaatccgaactaaccaaaaagtctatggaaagttatttaccgtatgtaatc
ctcggcgttctatacgcctacttgttgttcctttcttggacacctgaaacggttcgattgatttc
gcgagtaaatacttactacctgagcttagtagcatagggaaaatgttctctagtgagttgacttta
gcctctgcttggattcatcttttggttgttgatctttttgctgcaaggcacattttccgcgatgga
atggagaatcagattgaaactcgacattcggtttcctttgcttgttcttctgccctattgggatt
cttactcatgtcatcaccaaagcaatgactaaaactacaagaacagagagtcatggtttatag

Fig. 2Z

SEQ ID No: 23

>*Vigna radiata* variant 1 NXS DNA tgaatcacttattagctcttttgcttttccttcaatcatgtctttctcttcttgcctttcccattc
cccattgacactcaaggtacactttctcttagctttcctattgctgccattgatttctaattttac
atgcaatttttcttccaccttttgctcattcgctacctttatttatcacttattttctttcctg
gcttcagctcatttccccatgcccactagattggagtttgattccctacgtttgaactctaaagt
tttaaactttgaatggttattggaccgaaagtggccattttgcgtagatttcaaccacctaagcat
taccaacgaattgggcatttgtgaatttatttttttgctttgcatggttgtttgcttgttttgctt
tgcatggatctattctaggcgcttgttggtgtagtagagttaaaaaggagtttgtatttctgaact
ggctttccgtgtcttcaaaagctctaaattcattcagttctgtgggtttgttcaaagagtccttg
cgtgttgaagtttcattcaaataataatctgcacaacctggttatttccactctagaaaaggttta
atataatttattcgtatatatggatagcataaggtgtactttctgggcttaagacaaactgtgctt
ataattgagattctgtttgtttcattttggcagcctataaaaccttgtggttctgttgggatgagg
caaaatttttgctttctctttcagaagtaattggcctgagctttgtaacagacacattgtagggagt
agaaggttgcagggaaatttaccaagggtcaacttaagtggagattggagtttyataggaggatcc
aaaattgttatgaaaccaaatgctacaagattgcttcattatccaaaaaggggtcaaatgcaagct
tcatgtaaccctcttatactacagcttctcattttcaaactcatttgaaaataacgtgtgtcttg
tgctggaccaaatttatttaagaaccaattgaagtctctggtattttgatgtggtgatactttc
tgtgtctctgagcaacttacaggtgaaattggaggttttataattaggcctctttcctctaaattt
ttctcatttgaccaccctggaaaatttcactgcattctgatttatataaatatcattagcgcaag
ctgtttcttcattcatatatttgattcttattaaaaaactgttggatttgtcttgccactaaact
aatttgtttatctcgaaatagagcacaaattaaggatttgattcacagaatgaatttacatggtta
gcttaaattaccccctcgtgtcagtatatctataacttaaattactgtatgatatacacgcacattg
aaactaccgagagctataaatatccgtgcattgtctgcatgacttcaccaagtgttgttcttagtt
caagcttaaccaagttactccgctttatttttttgaaattttagggaccagttattgattttaagt
tgtccctttgatttagtcttccccatttcatgtggctgccgattccggctatctgtgctgttgt
ggttcctacttttttcattattctctagcataatgtgactttgaatttgatagccttgaggaaagtc
attttgtttggacagaaaactctttaatgtcgaatctgaacagctttttctaacatggtgcttaaa
atttaaatcttgctactagttctgctcttgaagcagatgttcaatttcttggaaaggtatgctagg
aatcaggtttcactgaagctattcagctgtggtctaaatttcgtacgaccattacattcattatgg
ttgggtttaaagtctgcctttacctttcgatatttttctatttactgttaaagcaatcgatcaca
atgagtaattctaaatagcaaagatgtgcttattgttatcttaactacttagacattttggtaatc
tgtttctctttgtataaagttgactgaatgttcctttattctgtataactgatggtgactatattt
ttcgcctgatactcactttcttcctttcattttcaggcttcataggatctcaacttgctagcact
gcatttacggctggaactgtagctgttctcccatttacacacttatggttctagctccaaattct
gatctagtatgtttctaactgcagtggagaaaatttacgaccaacgagcacgattcattgcaacaa
ctttgctttattacatgtctgtttagttaccatgcaaaaatcattcacatatataattattttcta
tagtagtaaataatccttgtgtggaatttggatattcttctttctcgtaagcttctattgggtctc
tgatttgtacttcacgtctttcctgattcatgttaagtgcaaaaatgcagaccaagaagtctatg
gagagtagtctgccatatgtagtgcttgggattctttatgcatatttgttgtacctttcttggaca
cctgagacagttcgattgattttgcaagtaaatacttgctaccagaggtgtgtgtgaatgcattc
agcaatgaagtttttcttcccaaaagagttgtatgcaactgataaatctgaatacttgatgcagct
gcctggtatagcaagaatgttctccagtgagttgactttggcctctgcatggattcacctgttggt
tgttgatctttttgctgcaaggtcgtggatttatctttctcttggtttctcattctttacttatt
tatctaatcctatttctggttatgaattcaggcatgtttttcaagatggactgaagaatcagattg
aaactcggcattctgtttctttttgcttgttcttttgccccattgggattcttactcatatcatca
ccaaagccatcaccaaagctgccacaaaagagggtcatggtttatagatggcac

Fig. 2AA

SEQ ID No: 24

>*Vigna radiata* variant 2 NXS DNA atggctttctcttccttctttttccattctccgacactattgaagattgatcacttggggcagact
aaaagaccttgtggtaaagttgaaaaggggcaaaagtttcctttctctgtcaggagtaatggtgct
gagactgaactttgtaaccagagtcaacttagtcagagaagtagagtcagagattggagtttcatg
agaggatcaagagttgctatgaaaccaaaaatcttgagattggctccttctcgaaaagtccctcgt
ctatatgcttcatggttgtcaggatcagaacttgctagcactgcctttacattaggaacaaccgca
gtgcttccattttacacactaatggttctagctccaaattctcaactaacgaagaagtctatggaa
agtagtgtaccatatattgggcttggagttctatatgcatatttattgcacctttcttggacccct
gagacagttggacttatttttgcaagcaaatatttgctaccagagctgactagtatagggaaaatg
ttctccagtgagatgactttagcctcagcatggattcacctttggttattgatctctatgctgca
agacatgtttttctggatggacttgagaatcagattgagacaagacattcagtttctctgtgcttg
ttcttttgccctattggtgttcttactcatgtcatcaccaaagcaacgactaaaagtagcagagaa
aacaagagtggattatag

Fig. 2BB

SEQ ID No: 70

>*Trigonella foenum-graecum* NXS DNA

Tgtctttctcttcwtgctattcwcaytcrccattgccatttaataataaggtacaacactttctctgc
tttcttttcctgttttttcaatttctgttttgtaatcttatctgcattttcttgtcttttttatgg
atatttgtacttttttttttttttttaatttccacaaatggggtttctgtttgatgtgtaaagtttg
aactttgaataaatatagctgaaattgaagattctttttgtcatagatttgaatcaccaatgcatta
ctaatgaaatgggcctttgagcttttatttttagtttgtaatagatctgatgctaggtgcatgttga
tgttggtatattggtaatgaactatgtagaagctacacttcagattgataatgtgtctggtgtttgac
acgtgtttgcggatacaacacgacattaacacatgtggttgcatttgatcactttcattttcttaaat
tgttacaggtgtctacgacttagtgtcgtgtcgtgtatgtgttagtgtttcaaaaagttgacactcct
gtatmaacaaaccaatatgtgtaaaaaaaactatgtagcaccgacacttcatattgaagatatgtatg
gtgtttgagatgcatcagtgtccagcaccgacacaatactgacacatgtggttacatttaattayttc
attttctcaaattatgatcaatgtcaatctgtcagtgtcgtgtctggtgtccgtatctggcttcattg
gcaacaamtatgtatttgttcatgtagtcattgcatattgagktgtaagaatcgtcagcrcgacctgt
atatttcctgttgaagatcaaacaatttagttcatttactcttaygaatggataacctagggtgtatt
tctgggttcaagaaattttattctattattgattgatcatcacttggggcaggatataaaactctgta
ggacagttgggcaagtgaagttgaattttcctttcgctataaggagtaatggtgttgagctgtgtact
cggcgcatttcgagatgtagattcgacttaagtggagattggagtttcataggagggtccagaattgt
tgtaaaacctaaagctgcaagatcggttcgctatacaaaaagaagtcaaatacatgcttcatgtaatc
tttttcatctaatctaaaatttgtacaagctgttccttagttcatataatttaccattcaktagaat
tggctgtgasggcgtttgaacataawaaagttaaattgytttcwtataacctataagttttttcsta
wsttatattckagagcttacraaaataarctgaaaacaacttatggacatgtcgtaacctgtttccag
aaactatactaaacagtctcataasttcttatgccaataaataagctcaaataastcaatccaaacag
gaatgcatttaatttttargttaccattttttggtggcgttatcataaagtagattactgtaagtactt
ttgtcttatcatctttatatgaacaacgaaactggaggcagtggttaatatctgttcattgatcatgg
tgtacaatgctatatatgataarttataaccttgcaatgtgttgctgaaggcaatatggttcacaatt
catgctttagttgagttagggtctgtttggattckcttatttgagtttaccttctaacataagcattt
gtgagactgtttgagagagtttatggaaacaacttatatacgacatgtgcataacttgttttaagtta
atttttataaattctccaagatagcttatgaaaacaacttacagattatatgaaaacagctcgacttt
atttatttttgttatagaaataacatatgcataagcacttatatgataaacaaggttttcttgttt
aggtggataccattgacttgaattgcttgttmtaatatacytgaaaattgaytaygatctatgcttaa
attgcttgttctgcatattcaytgtxxxxxxxxxxxxxxxxxxggttcatgggatctcaacttgctag
cactgtatttacatggggaacgattgcagtgctcccgttttacaccccttatggttctagccccgaaat
ccgagctggtacgtttctttttttgtatttgtgaaaaattatgattagtaatctcatttcacaattcat
attcagttatgatattctttttcatttcatttatttggttatgattctgatatgctgattcggttttc
tgaaatgcaaaaatacagaccaaaaagtctatggaaagtaatttaccatatgtagtgctcggcgtt

Fig. 2CC (continued)

ctatacgcttatttgttgtgcctttcttggacccctgaaacagttcgattgattttcgcgagtaaa
tacttactacctgaggtgtgtattcatttattaatgaagttaaatttctttctctaaagagttca
attatcaataattgtgttatatttgcatactctatgcagcttactagcatagggaaaatgttctct
agtgagttgactttagcctctgcttggattcacctttggttgttgatctttttgctgcaaggtcc
tgattttatctctttgtttttgttgctcagtaatgagatttgacacaaatttgacaaaaaaaagt
agaaaacaatttggatagttaatgccgttcgaatatgcggttaattacatagtgaatggttaatga
atattacaaaatacaaaatgtcacaagtcattaaccctgattttgaacgccgttaatcataaactt
taggtgttcaaacatacgtgatattcattaaccattccaattatgttcacgatcttcaggtttca
aatatacataatattctattaatcacaattttgttcaaatatacaaatgtaattgtggttaatga
cattcaaaatagtggttaattgtgatctattgatgggtaatgagttatgacactttgttataatca
gtaaccatctactaaatgtaattaaccttatatttgaactacattaacatttaaattgttgtcaaa
ttttatggtctaattttgtgtcaaaataacacggctctttctcatgcttaaattatttttctgata
gtatttgtggttctaaatccaggcatattttccgcgatggaatggagaatcaaattgaaacacgac
attcggtttccttttgcttgttcttttgccctgttgggattgtaactcatgtcatcaccaaagcaa
tgaccataaaaacaagaaaagagggtcatggtt

Fig. 2DD

SEQ ID No: 26

>*Chicorium intybus* NXS DNA atggctttctcttcttgtctttgccaccatcaattggcactcaaggtattggttaatttccctttt
tactctctctatgtgtgtttgcatatgctcaaacgacttcactttcacgaattcatggtttatttg
gcattttgcgatttgggtacgagtcatttcgcgttattggtactaaatctggttgattttgccgat
ttaactaccagtgtcatccaatttgtgcattttcacatgtttttagctacctcactttttacatatt
cctgtttgtttgcgaatttactatctgggtgtgattcagtttgctgtgttcgtgttaatttggttg
ttttggctcatttgattctgtttattacatccatttctgtattgtgtgactgcagattgaatcatt
cactttacatatacatattatgctgtctgtaaatctattcgtttgtatcttctccccaattgaatt
ggttcacttttccgatttgatttcggttagcagtttagggttcatagatgtttatgttcaaatta
gaaccatcaaaagggttacattagtgagaaatcttgaagatgttaaatcttgttgcagatcaacc
tcttaacgagtccatcaaaacccacattcgctcttaaagccatgaacaccgaattttacggaatac
atatcggaagcaagctaggaaatcaatggagttttatgaaaggatcacaagccataatcagaccga
accctggaagcttcaatctgcatcaaaaaagctcaaaattgcaagcatcatgtaatcctttcgtac
cctttgtttatcatgatacaatttatcgattaaacatccaaaactttgttaatcttatcgtttttt
agttcgattggatatttttttcatgtagggtttgcgagtatgcatttagcgagcgatgcttttacat
taggaaccgctgctgttcttccattctacacccttatggtcgcagctccaaaatccgaattggtaa
ggtttataatgttgtcataaagcaaagaaattaaaaaaaaacaaaaaaaaaaaaaaaattcatt
caaatacctatatcaatatagttggaatttaagtgatgtttctttttgactcatttaaagtgttga
atggataaattgtttttttttttctttttgggtaaagtgtcgaacatggtatatattaattgttta
atatattaagttcattaagtaaaaaagaagctaattgtttacaaatttggttgacattaatgcaga
cgaaaaagtgtatgagaagtagcataccgtatgtggtactcggggtttatactcgtatcttcttt
acctctcgtggacgcccgacacagtccgattaatgtttgcaagcaaatactggctgcccgaagtat
gattttacacccctatagtttgctagatagccgacttttaaccctagtgatggtttatttgcagc
ttccgggtgttgctaagatgttttctaatgagatgacattagcctccgcttggatccatttgttag
ccgtcgacctctatgctgcaaggtaggagggcatttacgtcttttacacaaacaacatatcgaaag
ctagtccatgtcccaccttcttccgtaggatgaaaaattgcaatttttttcccctgtacctgtacc
tgtacctgtacctgatgaattgtggttttgattggtggaaacagacaggtgtatcatgatggattg
gagaaggagatcgagacacgacattcggtttctctttgtttgttgttttgtccgattgggatactt
gttcatgccatcaccaaggctttgattagtacatatagagaatcaaaaacagagattcattga

Fig. 2EE

SEQ ID No: 27

>*Allium cepa* variant 1 NXS DNA atgcctctcctttgctcctgcgattccaggatctataaacaggcaactccattgtcaaatcaactg
aataaatggcgaggtcttagttcacatgcccaacaattcattcctaatggaagcaaagatatagtt
caatggagttttaaaggagggtcaaagatagttattcaaccaaaaatatcaaagatcagttaccac
aaaagaggctccgacatatctgcttattggattcctacatcgcaaatagcttcgaatgccttcaca
atgggaaccgttgccgttcttccattttatacgttgatggttgttgctcccaactcaaagcttaca
aaaaggacaatggaaagcagcataccgtatgttgttcttggtatgctatacatgtatcttctatat
ctatcgtggacacctgagacgttggggtatatatttgcaactaaatattggctgcccgagttatcc
ggcatatcaaaaatgttctcaaatgaaacttgcacgtcttctgcctggattcatctactgactgta
gatctttttgccgcaagacaagtattccaagatggtataaagaacaagatagaaacccgacattct
gtttcattgtgccttctctgttgtccaattggtatcgccactcacgcaattacaaaagctctgaag
agggtgtcagatagtcgatcacactga

Fig. 2FF

SEQ ID No: 28

>*Allium cepa* variant 2 NXS DNA atgtctctccattacagcttttgcaacacccgcatctctcatcaggttgttcattcatggaatgct
ccagatagatatgcagtttatgcatttttatcagctagaaataaacatgatgaacatattgggcga
caggtagcacatacaaaaagcagaaacagggttaaatggagcttcagaggaggatcagagctgttt
attcaaccaaaagccacaaggactgaccgtcaaaaacatcgatctgctctgttaacatcgtgctta
acaagttcacaaattgctgcaaaagcttttacatggggaaccattgcagttcttccattctacaca
ctaatggtagtagctcccaatgctaaacttactaaaagagccatagaaagcaacacaccatacatc
attcttggagcaatatacagctaccttctctacctgtcctggagtccttccacattgcgaacaatg
ttcgctagtaaatactggttgcctcagttatctggcatctgcagcatgttctcgaaggaaatgacc
gttgcttcagcttggattcacttgctagctgtggatctcttcgctgccagacaagtatactgtgat
ggcatattgaacaacatagaaacaaggcattctatttcattgtgccttctcttctgcccaatcggg
attgcgattcatgccattaccaaggcacttaccaaatatttttgaactataatttttcggaagag
atgaaactggggctaaggagttag

Fig. 2GG

SEQ ID No: 29

>*Hordeum vulgare* NXS DNA atggccgcccctcttccctccccccttccccgagcccggcagctccaccacctcgtcgactcccgg
caagaaatggcggcctccccaccgccctcgccctcgccctctcccccaccacgcgggtggttgtc
aggcggacgccggcgccgcgcgtggccgccgtctcccccggccagctccgcgcgagctcctggggc
gcgccgctccctctccggccggagctcgccgcggcccctcctcgacccggcgccgcccgccgcagg
gcgcctctgctccggcctcgagcatggctgtcgacgtcccagatcgccagctccgccttcaccctg
ggcaccgtcgccgtgctccccttctacacgctcatgatcgccgcccccaacgccaacatcactaag
cgcacagtggagagcaccgcccccctacgtggccctcggcatcctctacgcctacttgctctacctc
tcctggacccccgacaccatccgcgccatgttcgccagcaagtactggctcccggagttgcctggc
attgtgaggatgtttgcgagcgagatgaccgtcgcctccgcctggatccacctccttgccgtcgac
ctcttcgccgcaagacaggtgtaccatgatggcatcaagaacaacatcgagaccaggcattcggtt
tccctgtgcctgctcttctgccccatcgggatcgccgctcacgcgctcactaaggtactggcgggg
tcgacagggcgatcgcactga

Fig. 3A

SEQ ID No: 30

>*Daucus carota* variant 1 NXS PROTEIN

MNKFVLENQNALLVSILKLGQYLPSWTWELLKYLSLYCLPNAYDENLETECLTEHSSLTRKGFYNI
SKIQLNPVAIEGTNSDLYGQHVVLWTKMRKEWSFKRGSISIAGPTMERFVLHRKSSGVQASWFTNS
QIASSVFTLATAAVLPFYTLMVLAPKATLTKKCIQSAVPYVGLGLLYAYLLYLSWTPDTFRLMFAS
QYWLPELSGIAKMFSSELTLASAWIHLLAVDLFAARQIFQDGLQNSVETRHSVSFCLLFCPIGILS
HEITKALTTGGRTAKREIH

SEQ ID No: 31

>*Daucus carota* variant 2 NXS PROTEIN

MASLSCLCSSPLFLKNDESRLANKSLLAYTRKDRITTYCLNSVETDFFSRHPHSIKTKRWSFKGGS
RVITGPNIQRFACYRKSCGVYALWLTNPQIASSAFTLGTAAVLPYYTLMVVAPKSELTKKSIESGI
PYVALGLLYGYLLYLSWTPDTMKMMFASEYWLPELSGIAKMFSSEMTLASAWIHLLAVDLFAARQV
YQDGLENKIETRHSISLCLLFCPIGIISHVVTKALTKSTEFPGFAFHNFSRLFHDILLTIANF

SEQ ID No: 32

>*Cichorium endivia* NXS PROTEIN

MAFSSCLCHHQLALKINLLTSPSKPTFVLKAMNTEFYGIHIGSKIENQWSFMKGSRAIIRPNPGSF
NLHQKSSKLQASWFASMHLASDAFTLGTAAVLPFYTLMVAAPKSELTKKCMRSSIPYVVLGVLYSY
LLYLSWTPDTIRLMFASKYWLPELPGVAKMFSNEMTLASAWIHLLAVDLYAARQVYHDGLEKEIET
RHSVSLCLLFCPIGILVHAITKALISTYRESKTEIH

SEQ ID No: 33

>*Solanum melongena* variant 1 NXS PROTEIN

MNCWAPASVSLSTRRNHTAFLALREIISQRIGGFGTKLSSGGSSLGGSRVIIQLNLQRTLSQRKSS
RVHACWLPSSEIASTAFTVGTAAVLPFYTVMVVAPKAELTRKAMKSSIPYIVLGLLYAYLLYLSWT
PDTIRLMFASKYWLPELSGIAKMFSNEVTLASAWIHLLAIDLFAARQVYHDGLQNDIETRHSVTLC
LLFCPVGILTHCITKALTSSPEKKQHRT

SEQ ID No: 34

>*Solanum melongena* variant 2 NXS PROTEIN

MALSSTCFCHSQFSLKMESWTPALSSNIRCYIRRNQFPSSMLKTINSDLSSQQVQERGTKHSNGSS
FLGGSRVMRQFNLQNLPQRRSCRVSAMWLPSSQVASSVFTLGTAAVLPFYTLMVAAPKAELTRKLM
GSAIPYVALGLLYTYLLYLSWTPDTIRLMFASKYWLPELSSIAKMFSSEMTLASAWIHLLAVDLFA
ARQVYHDGLQNGIETRHSVSLCLLFCPIGIVIHLLTKAVLSNAENIVPRTH

Fig. 3B

SEQ ID No: 35

>*Solanum lycopersicum* variant 1 NXS PROTEIN

MYFSSSSHVSLKMNCWAPALASKVPLNTRRNQTASPALRQMKSDLLSQRIGGFGTNLSSGGSSLGG
SRIITQLNLQRTLSRRKSPMVSACWVPSSEVASTAFTVGTAAVLPFYTVMVVAPKAELTRKAMKSS
IPYIVLGLLYAYLLYLSWTPDTIRLMFASKYWLPELSGIAKMFSNEVTLASAWIHLLAIDLFAARQ
VYHDGLQNDIETRHSVSLCLLFCPVGILTHCITKALTSSPEKKQHRTH

SEQ ID No: 36

>*Solanum lycopersicum* variant 2 NXS PROTEIN

MALSSTCFSHSQFSLKMDCWTPALSSNILCYIRRKQPPSSTLKTINSNLLSQQVHKRRTKHGNGWS
FLGGSRVKCQPNLQNLPQRRSYRVSAMWLPSSQVASSVFTLGTAGVLPFYTVMIAAPKAELTRKLM
DSAIPYIVLGLLYAYLLYLSWTPDTIRLMFASKYWLPELSGIAKMFSSEMTLASAWIHLLAVDLFA
ARQVYHDGLQNGIETRHSVSLCLLFCPIGIVIHLLTKAVLLSSAEKTVFRTN

SEQ ID No: 37

>*Capsicum annuum* NXS PROTEIN

MNCWTPAFVSKVPLNTWRNQTASLALREMKSDLLSQHIGGFETKHSSGGSSLAGSRVTIQLNHQRT
LSQRKSFRASACWLPSSEVASTAFTVGTAVVLPFYTIMVVAPKAKLTKKAMKSSIPYIVLGLLYAY
LLYLSWTPDTIRLMFASQYWLPELPGIAKMFSNEVTLASAWIHLLAIDLFAARQVYHDGLQNDIET
RHSVSLCLLFCPVGILTHFITKALTSSPEKRQRRIH

SEQ ID No: 38

>*Brassica oleracea* NXS PROTEIN

MAFSQPLSSSSLSMTNRSFVAKSSVTASLSLNKSLKIRFHNRWSFDGGSRIVLFPSVSSDSSSLVH
KKRSCVRASWMATSQIASSVFAVGTTAVLPFYTLMVVAPKAEITKKCMESSIPYVVLGVLYAYLLY
LSWTPETLKYMFSSKYLLPELSGIAKMFSSEMTLASAWIHLLVIDLFAARQVFNDGLENKIETRHS
VSLCLLFCPVGIVSHVVTKALTNSSTSNTNNQCK

Fig. 3C

SEQ ID No: 39

>*Apium graveolens* variant 1 NXS PROTEIN

MPLSSCLYCYQISSLKTEHSTLSTKPLCNIGQSRLNTVAIEGINSDLYGQHLVLWTKMKKEWSFKG
GSTSIAVPTIQRSVLYRKSLEVQASWFTNSHIASSVFTLATAAVLPFYTLMVLAPKANLTKKCIQS
TLPYVVLGILYAYLLYLSWTPDTFRLMFASQYWLPELSGIAKMFSSELTLASAWIHLLAVDLFAAR
QIFIDGLQNYVETRHSVSFCLLFCPIGILSHEITKALTTGGRNTKRQIR

SEQ ID No: 40

>*Apium graveolens* variant 2 NXS PROTEIN

MASFSCLCSSSLFVKNDDLRLTNRLLEACFRKDQLTTCALKSFKTDPFSRHPPSIKTKSRTEWSFK
GGSRAIPGPTIHKFARNRKSCGVYASWFTNPQIASGAFTLGTAAVLPYYTLMVVAPKSELTKKSIE
SGIPYVTLGLLYGYLLYLSWTPDTMRLMFASQYWLPELSGIAKMFSSEMTLASAWIHLLAVDLFAA
RQVYHDGLENKVETRHSISLCLLFCPIGIISHVVTKALTKSSK

SEQ ID No: 41

>*Spinacia oleracea* NXS PROTEIN

MALSSCFAYHPQISSKIDCSVLVDKNHHQVGLSPSLVLSVQGVRNGIFSQKVPKLRAEIMHGCCFL
GGLRIDIRPTVNESNFSRRNSGVCYSWLSNTQVASSAFTLGTAAVLPFYTLMIVAPKAELTKKTMK
SSIPYVVLGLLYAYLLYLSWTPETIRLMFASKYWLPELQGIAKMFSSEMTLASAWIHLLVVDLFAA
RNVYQDGLEKEVETRHSVSMCLLFCPVGILSHLITTALTRPSDKTRHSDTII

SEQ ID No: 42

>*Valerianella locusta* NXS PROTEIN

MAFSSCFCHPQFSLKMDCSISTVKSSYITRNQKQLTNFTLGSTNGQPFGQHFAWKEAKLSCGSSFS
GRSKAIVSSNPRKLIHPRKYCRIYASWWSNPTTIANNVFTLGTVAVLPFYTLMLVAPKAELTQKSM
ESSIPYIVLGVLYACLLYLSWSPDTLRLMFASKYWLPELPGIAKMFSNEITLASAWLHLLAIDLYA
ARQVYKDGIENNIETRHSVSICLLFCPIGIIVHYITKALTI

SEQ ID No: 43

>*Rhaphanus sativus* NXS PROTEIN

MMNRSIIANSSVRASLCLNKSRVCVDSLKIQFQNRWSFIGGSRLAFLPSLSSNPSSFVHKKPSCVR
ASWLATSQIASSVFAVGTTAVLPFYTLMVVAPKAEITKKCMESSIPYVVLGLLYAYLLYLSWTPDT
LKYMFSSKYLLPELSGIAKMFSSEMTLASAWIHLLVIDLFAARQVFNDGLENKIETRHSVSLCLLF
CPVGIVSHVVTKALTNSSTSNTNNQCK

Fig. 3D

SEQ ID No: 44

>*Capsicum baccatum* NXS PROTEIN

MNCWTPALVSKVPLNTWRNQTASLALREMKSDLLSQHIGGFEIKHSCGGSSLAGSRVTIQLNHQRTLS
QRKSFRVSACWLPSSEVASTAFTVGTAVVLPFYTIMVVAPKAKLTRKAMKSSIPYIVLGLLYAYLLYL
SWTPDTIRLMFASQYWLPELPGIAKMFSNEVTLASAWTHLLAIDLFAARQVYHDGLQNDIETRHSVSL
CLLFCPVGILTHFITKALTSSPEKRQRRIH

SEQ ID No: 45

>*Chenopodium quinoa* NXS PROTEIN

MAFSSCFAFHPQISSSKIDCRVLVHKIHHKAGLSPSLALSHQGVSTEIYSQQVSKLRPDVKHDWCFLG
GLRIDVRPKVNKFVFSKKNSGVCYSCSTFNPMQHTLLVISGLPDPQIATSAFTIGTAAVLPFYTLMVV
APKAELTKKTMKSSIPYVVFGLLYAYLLYLSWTPETISLMFASKYWLPELQGIAKMFSSEMTLASAWI
HLLVVDLYAARQVYHDGLQNEIETRHSVSMCLLFCPIGILSHLITSSLTKPAEKTRHTDTII

SEQ ID No: 46

>*Fagopyrum esculentum* NXS PROTEIN

MALSTCFSHARIFLQNDMGSKVQRTQLNFRLETRHTVSRQSLNIQHFCQNPLSEQSLGLGCMTAARTK
INTTSLSKKRPGICSCWMVGSQIASNAFTLGTAAVLPFYTLMVFAPKAEMTKKAMDSSIPYVMLGLVY
AYLLYLSWTPDTIKLMFASKYWLPELPGIAKMFSNEMTLSSAWIHLLIVDLFAARRIYHDGLENKIET
RHSVSMCLLVCPIGILMHTITKALTRTRVESSKHNV

SEQ ID No: 47

>*Lens esculenta* NXS PROTEIN

MSFSSCYSHLPLAFNKDIKLCRTVGQEKLNFPFTIRSNSVELCTRRISSSRAGLSGDWSFIGGSKIVV
KPKATTSFRNPKRSQIHASWFIGSQLASTVFTWGTIAVLPYYTLMVFAPKSELTKKAMQSNLPYVILG
VLYAYLLCLSWTPETVRLIFASKYLLPELSSIGKMFSSELTLASAWIHLLVVDLFAARHIFREGMENQ
IETRHSVSFCLFFCPIGILTHVITKAMTKTTRKQGHGL

SEQ ID No: 48

>*Medicago sativa* NXS PROTEIN

MSFSSCYSHSPLPFNKDIKLCRTVGQLKLNFPFSIRSDGVTKHISRSRFSLSGDWSFIGGSRIVVKPK
ATRSVRHPKRSQIHASWFIGSQLPSTVFTWGTIAVLPFYTLMVLAPKSDLTKKSMESSLPYVVLGILY
AYLLCLSWTPETVRLIFASKYLLPELSSIGKMFSSELTLASAWIHLLVVDLFAARHIFHDGLKNQIET
RHSVSFCLFFCPIGILTHVITKAMTKTTRKDGHGL

Fig. 3E

SEQ ID No: 49

>*Pisum sativum* NKS PROTEIN

MVFAPKSELTKKSMESYLPYVILGVLYAYLLFLSWTPETVRLIFASKYLLPELSSIGKMFSSELTLAS
AWIHLLVVDLFAARHIFRDGMENQIETRHSVSFCLFFCPIGILTHVITKAMTKTTRTESHGL

SEQ ID No: 50

>*Vigna radiata* Variant 1 NKS PROTEIN

MSFSSCLSHSPLTLKPIKPCGSVGMRQNFAFSFRSNWPELCNRHIVGSRRLQGNLPRVNLSGDWSFIG
GSKIVMKPNATRLLHYPKRGQMQASCFIGSQLASTAFTAGTVAVLPFYTLMVLAPNSDLTKKSMESSL
PYVVLGILYAYLLYLSWTPETVRLIFASKYLLPELPGIARMFSSELTLASAWIHLLVVDLFAARHVFQ
DGLKNQIETRHSVSFCLFFCPIGILTHIITKAITKAATKEGHGV

SEQ ID No: 51

>*Vigna radiata* Variant 2 NXS PROTEIN

MAFSSFFFHSPTLLKIDHLGQTKRPCGKVEKGQKFPFSVRSNGAETELCNQSQLSQRSRVRDWSFMRG
SRVAMKPKILRLAPSRKVPRLYASWLSGSELASTAFTLGTTAVLPFYTLMVLAPNSQLTKKSMESSVP
YIGLGVLYAYLLHLSWTPETVGLIFASKYLLPELTSIGKMFSSEMTLASAWIHLLVIDLYAARHVFLD
GLENQIETRHSVSLCLFFCPIGVLTHVITKATTKSSRENKSGL

SEQ ID No: 52

>*Trigonella foenum-graecum* NXS PROTEIN

MSFSSCYSHSPLPFNNKDIKLCRTVGQVKLNFPFAIRSNGVELCTRRISRCRFDLSGDWSFIGGSRIV
VKPKAARSVRYTKRSQIHASWFMGSQLASTVFTWGTIAVLPFYTLMVLAPKSELTKKSMESNLPYVVL
GVLYAYLLCLSWTPETVRLIFASKYLLPELTSIGKMFSSELTLASAWIHLLVVDLFAARHIFRDGMEN
QIETRHSVSFCLFFCPVGIVTHVITKAMTIKTRKEGHGL

SEQ ID No: 53

>*Chicorium intybus* NKS PROTEIN

MAFSSCLCHHQLALKINLLTSPSKPTFALKAMNTEFYGIHIGSKLGNQWSFMKGSQAIIRPNPGSFNL
HQKSSKLQASWFASMHLASDAFTLGTAAVLPFYTLMVAAPKSELTKKCMRSSIPYVVLGVLYSYLLYL
SWTPDTVRLMFASKYWLPELPGVAKMFSNEMTLASAWIHLLAVDLYAARQVYHDGLEKEIETRHSVSL
CLLFCPIGILVHAITKALISTYRESKTEIH

Fig. 3F

SEQ ID No: 54

>*Allium cepa* Variant 1 NXS PROTEIN

MPLLCSCDSRIYKQATPLSNQLNKWRGLSSHAQQFIPNGSKDIVQWSFKGGSKIVIQPKISKISYHKR
GSDISAYWIPTSQIASNAFTMGTVAVLPFYTLMVVAPNSKLTKRTMESSIPYVVLGMLYMYLLYLSWT
PETLGYIFATKYWLPELSGISKMFSNETCTSSAWIHLLTVDLFAARQVFQDGIKNKIETRHSVSLCLL
CCPIGIATHAITKALKRVSDSRSH

SEQ ID No: 55

>*Allium cepa* Variant 2 NXS PROTEIN

MSLHYSFCNTRISHQVVHSWNAPDRYAVYAFLSARNEHDEHIGRQVAHTESRNRVKWSFRGGSELFIQ
PKATRTDRQKHRSALLTSCLTSSQIAAKAFTWGTIAVLPFYTLMVVAPNAKLTKRAIESNTPYIILGA
IYSYLLYLSWSPSTLRTMFASKYWLPQLSGICSMFSKEMTVASAWIHLLAVDLFAARQVYCDGILNNI
ETRHSISLCLLFCPIGIAIHAITKALTKYFLNYNFSEEMKLGLRS

SEQ ID No: 56

>*Hordeum vulgare* NXS PROTEIN

MAAPLPSPLPRARQLHHLVDSRQEMAASPTALALALSPTTRVVVRRTPAPRVAAVSPGQLRASSWGAP
LPLRPELAAAPPRPGAARRRAPLLRPRAWLSTSQIASSAFTLGTVAVLPFYTLMIAAPNANITKRTVE
STAPYVALGILYAYLLYLSWTPDTIRAMFASKYWLPELPGIVRMFASEMTVASAWIHLLAVDLFAARQ
VYHDGIKNNIETRHSVSLCLLFCPIGIAAHALTKVLAGSTGRSH

HIGH TEMPERATURE SEED GERMINATION

RELATED APPLICATIONS AND INCORPORATION BY REFERENCE

This application is a divisional of U.S. application Ser. No. 15/451,497 file Mar. 7, 2017, which is a continuation-in-part application of International Patent Application Serial No. PCT/EP2015/071082 filed Sep. 15, 2015, which published as PCT Publication No. WO 2016/041952 on Mar. 24, 2016, which claims benefit of European Patent Application Serial Nos. 14184800.2 filed Sep. 15, 2014 and 14198005.2 filed Dec. 15, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Jun. 28, 2017, is named 43104_00_2296 SL.txt and is 165,955 bytes in size.

FIELD OF THE INVENTION

The present invention relates to a seed that is capable of germinating at a high temperature. The invention further relates to plants, progeny and propagation material that produce seeds with this capacity and their uses. The invention relates in particular to high temperature germination in lettuce.

BACKGROUND OF THE INVENTION

The ability of a seed to germinate quickly and uniformly in different environmental conditions is a highly desirable characteristic amongst growers. Temperature is a key environmental signal that regulates germination. Seeds have developed a mechanism known as thermoinhibition, a form of secondary or induced dormancy, to prevent premature seed germination during supraoptimal temperatures, such as those that may occur during hot summer months.

In seeds, the plant phytohormone abscisic acid (ABA), a stress hormone, has been implicated in the thermoinhibition of seed germination. Levels of ABA have been shown to rise in response to abiotic stress such as high temperatures but rapidly decrease at optimal temperatures. ABA thus plays an important role in the regulation of thermoinhibition of seed germination.

Seed priming allows for the controlled hydration of seeds, allowing the seeds to complete the first steps in the germination process before they are dried back to their original moisture content, and stored until planting. One of the primary benefits of seed priming is the ability to alleviate thermoinhibition by increasing the maximum temperature at which germination will occur.

Although seed priming may be beneficial to seed germination, it is an expensive procedure in terms of labour and equipment requirements, the types of ingredients that are used, and the time it requires for hydrating and drying back the seeds. In addition, the priming process may result in a reduction of the shelf life of primed seeds, as compared to untreated seeds. This undesirable side effect is influenced by the rate and extent of the drying back procedure.

Moreover, there is an inherent risk of "overpriming" which may lead to damage of the radical tips of the seeds, and subsequently, poor seedling growth. Overpriming would render primed seeds useless, thus making elaborate seed quality checks an additional necessity of the priming process.

By developing seeds that are capable of germinating at high temperatures without the need for priming, the expensive and potentially precarious process of seed priming becomes obsolete.

Improving the capability of seeds to germinate at a high temperature may also enlarge the total acreage for vegetable cultivation. Areas of the world with relatively warm winters are currently unsuitable for certain crops to grow, since the germination capabilities of such varieties may be insufficient to overcome thermoinhibition under such high temperatures.

In a more global context, rising temperatures due to global warming may have a considerable impact on soil temperature. As such, high temperature and the resulting increase in soil temperatures, is considered a significant environmental stress that may limit worldwide crop productivity in the near future.

Citation or identification of any document in this application is not an admission that such document is available as prior art to the present invention.

SUMMARY OF THE INVENTION

In the research leading to the present invention, it was surprisingly found that modification(s) to the lettuce neoxanthin synthase gene provided lettuce seeds with the capability to germinate at a high temperature, which is significantly above the germination temperature for lettuce seed which may comprise a wild type neoxanthin synthase gene. As used herein, neoxanthin synthase is abbreviated as NXS. NXS is an enzyme in the ABA pathway which catalyses the formation of neoxanthin from violaxanthin, precursors of ABA. Since NXS is an enzyme in the ABA pathway, it is expected that modifications to the NXS gene and/or encoded NXS protein that will lead to a lower neoxanthin level will also lead to a reduction in ABA levels, thus allowing for seed germination to still occur at high temperatures. The highly conserved nature of the ABA pathway means that modifications to the NXS gene and the resultant trait, like those which were found in the present research, are widely applicable to other plant species in which an orthologous NXS gene with a similar function exists.

It is thus the object of the present invention to provide seeds with an improved capability to germinate at a high temperature. In turn this would reduce or eliminate the need for costly priming treatments, and/or allow greater uniformity and reliability of germination, and/or potentially increase the total acreage for crop cultivation.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIGS. 1A-C: Lettuce (*Lactuca sativa*) NXS (genomic) DNA (SEQ ID No. 1; FIGS. 1A-1B) and NXS protein sequence (SEQ ID No. 2; FIG. 1C). The ATG translation start site is bolded and underlined. The wild type positions of the two modified codons ($T_{3017}G_{3018}G_{3019}$ and $C_{3518}C_{3519}A_{3520}$) and conserved tryptophan codon ($T_{3196}G_{3197}G_{3198}$) are in bold and underlined.

The numbering of FIGS. 1A-C in the priority applications and all references to FIGS. 1A-C therein began at and included the ATG translation start site which is located downstream from the first nucleotide in the figure. The numbering of SEQ ID No:1 in the current application and all references to SEQ ID No:1 herein begins at the first nucleotide position that is shown in the figure, which is upstream of the start codon. For ease of reference, the following Table indicates nucleotide positions as they were numbered in the priority application(s) in relation to the ATG start codon and their corresponding numbering in SEQ ID NO:1 of the current application.

| Numbering in priority application(s) | Numbering in current application |
|---|---|
| $T_{1218}G_{1219}G_{1220}$ | $T_{3017}G_{3018}G_{3019}$ |
| $C_{1719}C_{1720}A_{1721}$ | $C_{3518}C_{3519}A_{3520}$ |
| $T_{1397}G_{1398}G_{1399}$ | $T_{3196}G_{3197}G_{3198}$ |
| $T_{1218}G_{1219}G_{1220}$ > $T_{1218}A_{1219}G_{1220}$ | $T_{3017}G_{3018}G_{3019}$ > $T_{3017}A_{3018}G_{3019}$ |
| $C_{1719}C_{1720}A_{1721}$ > $T_{1719}C_{1720}A_{1721}$ | $C_{3518}C_{3519}A_{3520}$ > $T_{3518}C_{3519}A_{3520}$ |
| SNP $G_{1219}$ > $A_{1219}$ | SNP $G_{3018}$ > $A_{3018}$ |
| SNP $C_{1719}$ > $T_{1719}$ | SNP $C_{3518}$ > $T_{3518}$ |

FIG. 2A-2GG: DNA sequence of NXS orthologues.

FIG. 2A; 2B: *Daucus carota* (variant 1 and 2),

FIG. 2C: *Cichorium endivia,*

FIGS. 2D; 2E and 2F: *Solanum melongena* (variant 1 and 2),

FIG. 2G; 2H, 2I, 2J: *Solanum lycopersicum* (variant 1 and 2),

FIG. 2K; 2L: *Capsicum annuum,*

FIG. 2M: *Brassica oleracea,*

FIG. 2N; 2O: *Apium graveolens* (variant 1 and 2),

FIG. 2P: *Spinacia oleracea,*

FIG. 2Q: *Valerianella locusta,*

FIG. 2R: *Rhaphanus sativus,*

FIG. 2S: *Capsicum baccatum,*

FIG. 2T: *Chenopodium quinoa,*

FIG. 2U: *Fagopyrum esculentum,*

FIG. 2V: *Lens esculenta,*

FIG. 2W; 2X: *Medicago sativa,*

FIG. 2Y: *Pisum sativum,*

FIG. 2Z; 2AA: *Vigna radiata* (variant 1 and 2),

FIG. 2BB; 2CC: *Trigonella foenum-graecum,*

FIG. 2DD: *Chicorium intybus,*

FIG. 2EE; 2FF: *Allium cepa* (variant 1 and 2),

FIG. 2GG: *Hordeum vulgare.*

FIGS. 3A-3F: Protein sequence of NXS orthologues *Daucus carota* (variant 1 and 2), *Cichorium endivia, Solanum melongena* (variant 1 and 2), *Solanum lycopersicum* (variant 1 and 2), *Capsicum annuum, Brassica oleracea, Apium graveolens* (variant 1 and 2), *Spinacia oleracea, Valerianella locusta, Rhaphanus sativus, Capsicum baccatum, Chenopodium quinoa, Fagopyrum esculentum, Lens esculenta, Medicago sativa, Pisum sativum, Vigna radiata* (variant 1 and 2), *Trigonella foenum-graecum, Chicorium intybus, Allium cepa* (variant 1 and 2), *Hordeum vulgare.*

Figure 4A:
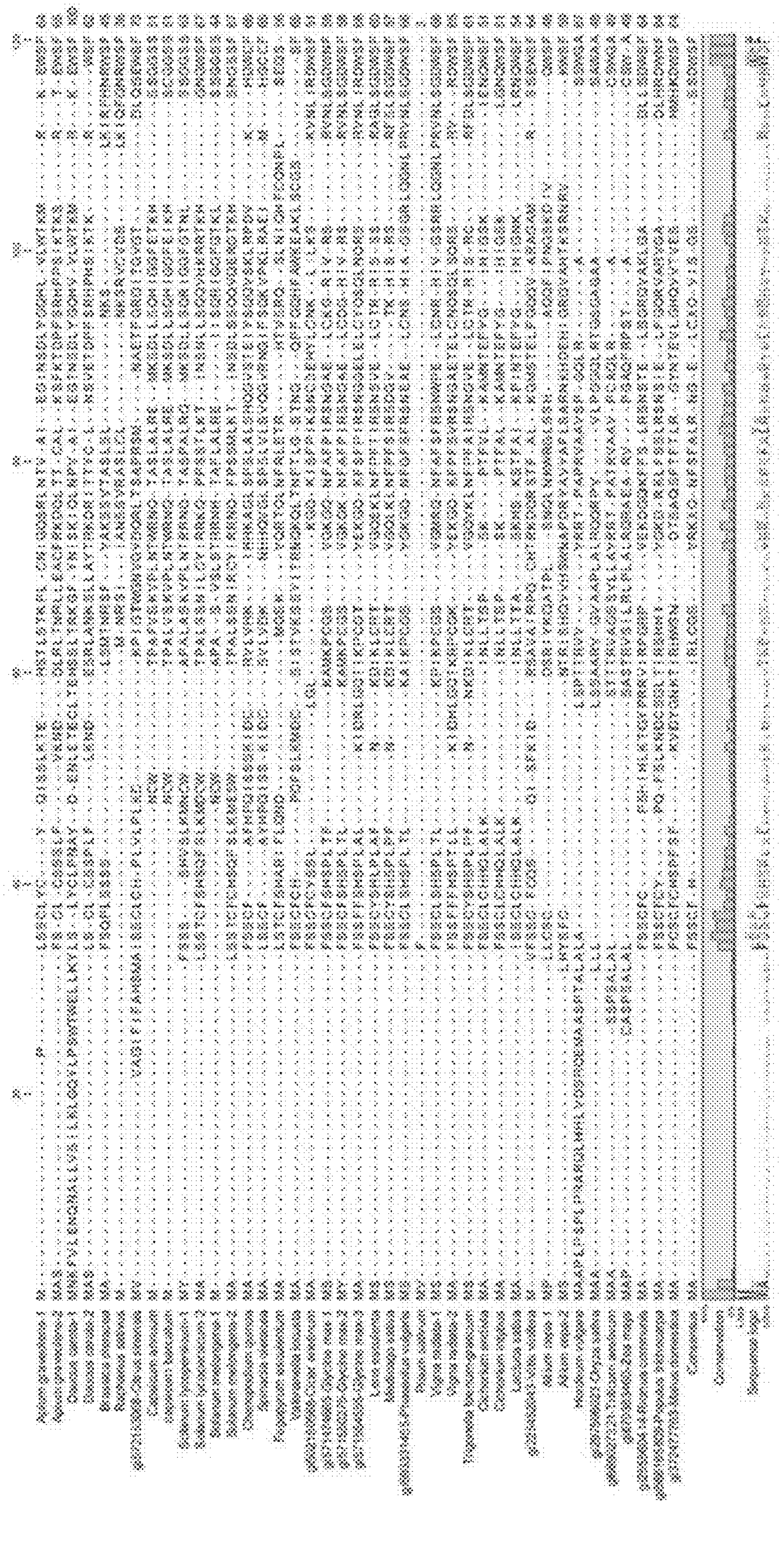
Figure 4B:
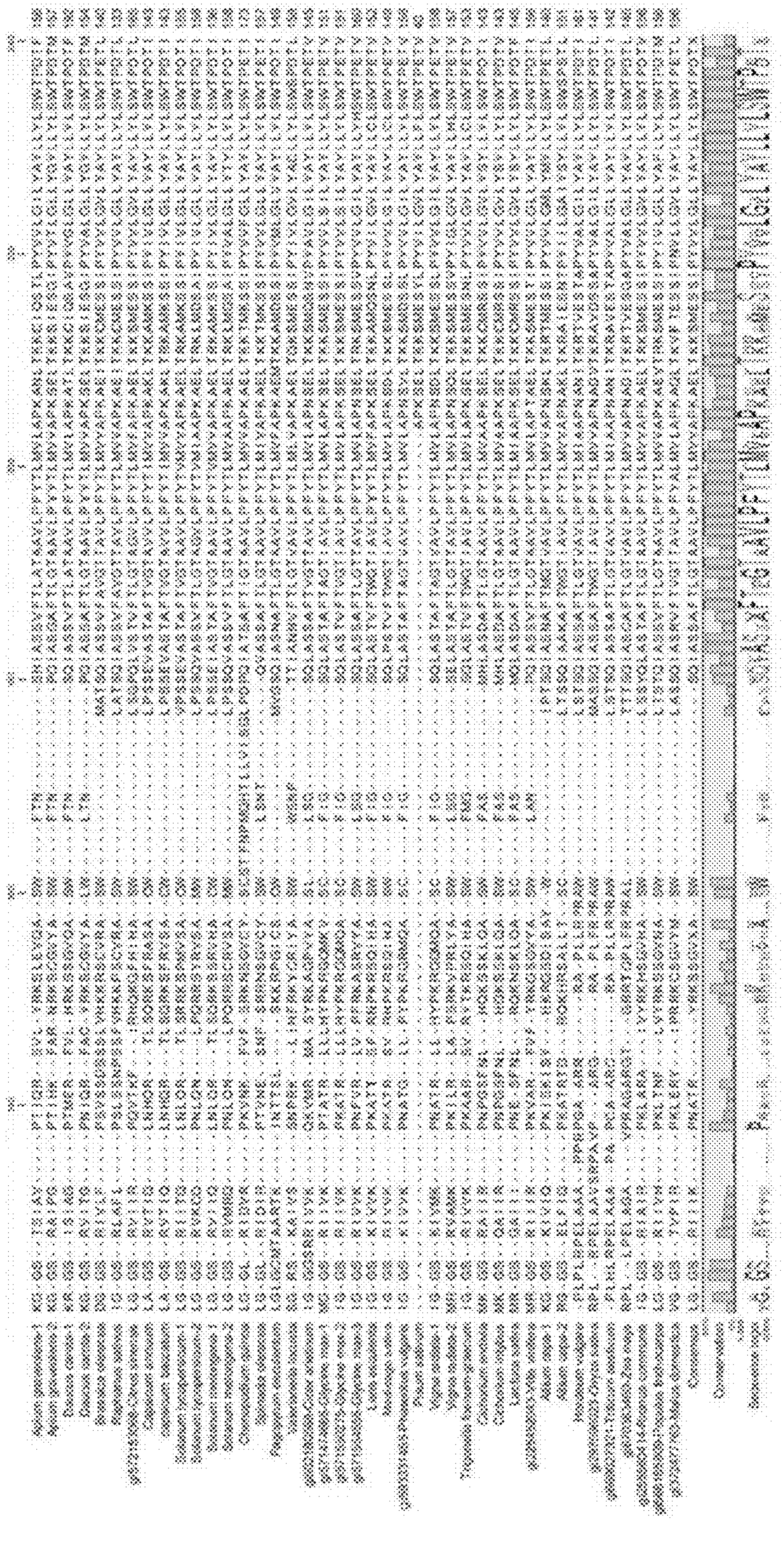
Figure 4C:
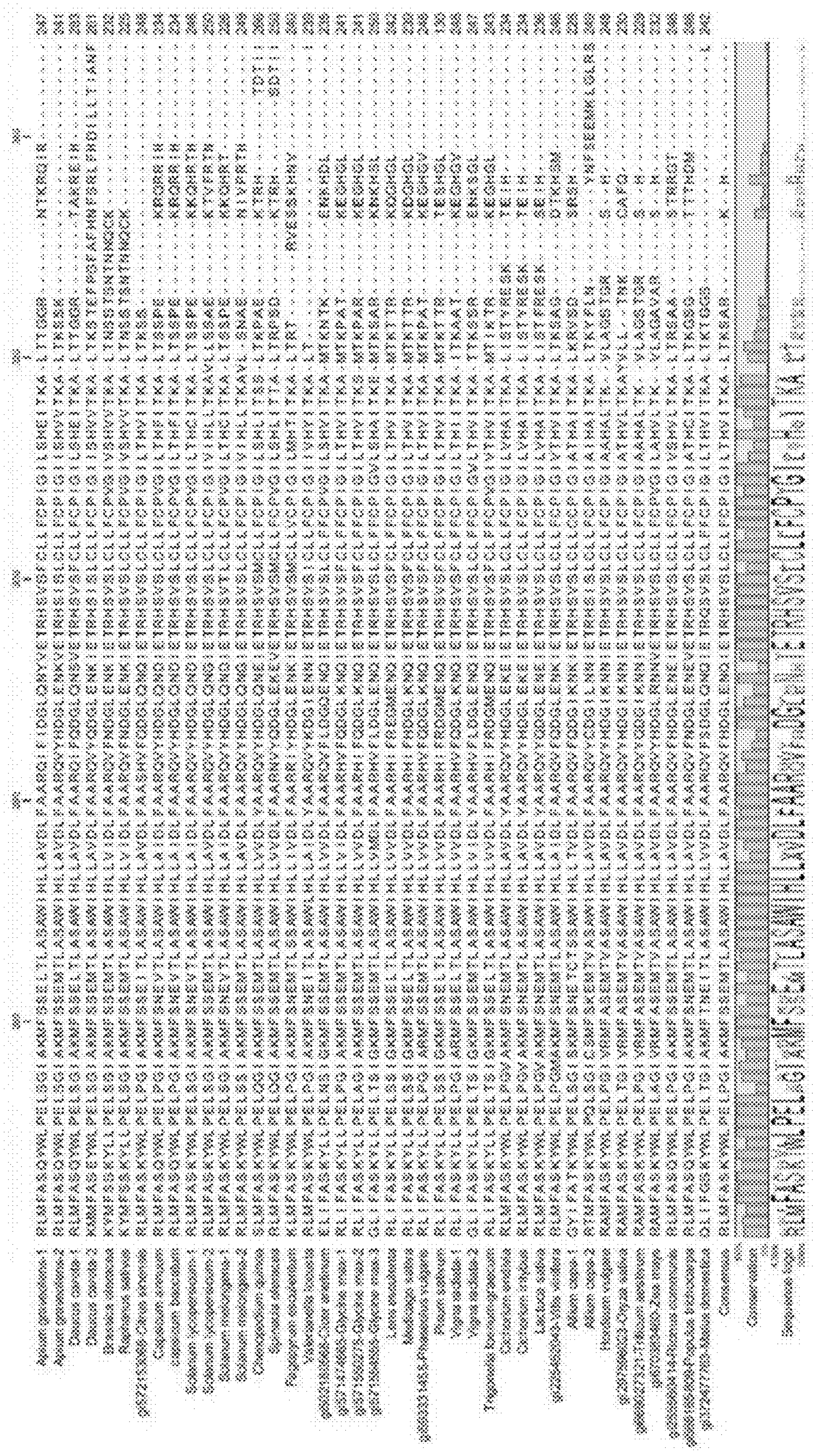

FIGS. 4A-4C: Multiple sequence alignment of orthologous NXS protein sequences from plant species from FIGS. 3A-3F and Table 1. FIGS. 4A-4C disclose SEQ ID NOS 39, 40, 30, 31, 38, 43, 57, 37, 44, 35, 36, 33, 34, 45, 41, 46, 42, 58-61, 47, 48, 62, 49-52, 32, 53, 2, 63, 54-56 and 64-69, respectively, in order of appearance.

Figure 5A:
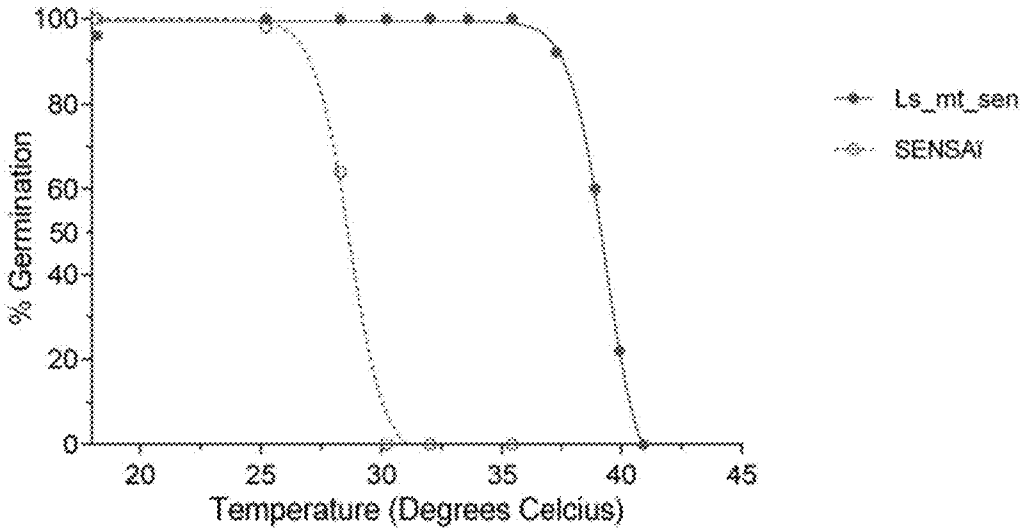

FIG. 5A: Graph showing the final germination percentages over a given temperature range, for the wild type Sensaï seed lot and Ls_mt_sen mutant seed lot. The GT50 Dark is the temperature at which the final germination percentage is expected to be 50%.

Figure 5B:
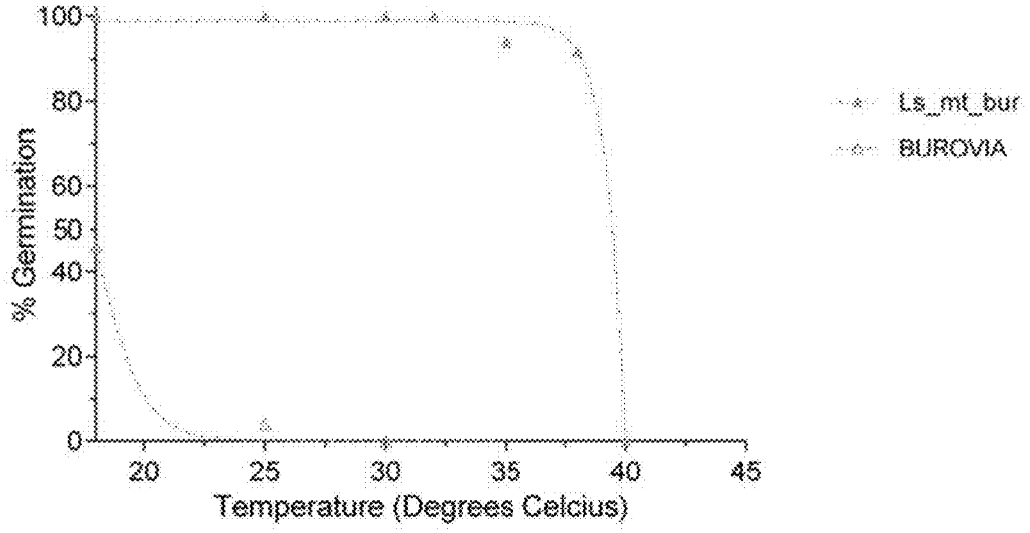

FIG. 5B: Graph showing the final germination percentages over a given temperature range, for the wild type Burovia seed lot and Ls_mt_bur mutant seed lot. The GT50 Dark is the temperature at which the final germination percentage is expected to be 50%.

Figure 5C:
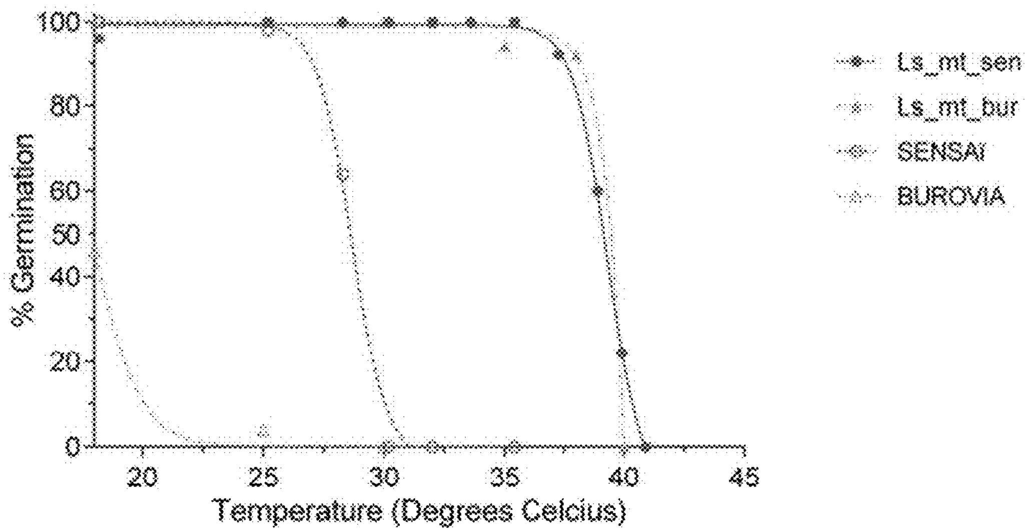

FIG. 5C: Graph showing the final germination percentages over a given temperature range, for both wild type seed lots of Sensaï and Burovia and mutant seed lots. The GT50

Dark is the temperature at which the final germination percentage is expected to be 50%.

DETAILED DESCRIPTION OF THE INVENTION

The present invention thus provides seeds which may comprise a modified NXS gene and/or modified regulatory sequences thereof in its genome. In one embodiment, the invention relates to seed which may comprise in its genome a modified NXS gene and/or modified regulatory sequences thereof, wherein the modified NXS gene and/or modified regulatory sequences thereof provides the seed with the capability to germinate at a high temperature as compared to wild type seed not having the modified NXS gene and/or modified regulatory sequences thereof. In another embodiment, the invention relates to a modified NXS gene and/or modified regulatory sequences thereof which provides a seed with the capability to germinate at a high temperature as compared to a wild type seed not having the modified NXS gene and/or modified regulatory sequences thereof in its genome. Thus, in the context of this application, the trait of the invention is the phenotype in which a seed which may comprise a modified NXS gene and/or modified regulatory sequences thereof in its genome has the capability to germinate at a high temperature. More in particular, in one embodiment the invention is the phenotype in which a seed which may comprise a modified NXS gene and/or modified regulatory sequences thereof in its genome has the capability to germinate at a high temperature in the dark. "Trait of the invention", "trait", or "phenotypic trait", may be used interchangeably.

In a particular embodiment, the invention relates to a modified *Lactuca sativa* NXS gene, the wild type of which is identified in SEQ ID No. 1, encoding the protein of SEQ ID No. 2.

In a more particular embodiment, the invention relates to lettuce (*Lactuca sativa*) seed which may comprise in its genome a modified NXS gene, wherein the modified NXS gene provides the seed in an unprimed state with the capability to germinate at a high temperature as compared to wild type seed not having the modified NXS gene.

When reference is made herein to the NXS gene of lettuce, the modification can also relate to the regulatory sequences of the gene. In the context of the present invention, such regulatory sequences can be enhancer sequences that are located within the intronic regions of the gene or may be located upstream or downstream of the gene that it regulates. Such regulatory sequences may even be located far removed from the gene on another part of the chromosome or even on another chromosome. Regulatory sequences thus control or regulate gene expression.

The said capability to germinate at a high temperature is controlled by modifications to the NXS gene and/or regulatory sequences thereof, the inheritance of which are consistent with that of a monogenic recessive trait. The term "recessive trait" is to mean in the context of this application that the fully achievable trait is only observable in seeds of a plant which may comprise a modified NXS gene and/or modified regulatory sequences thereof in the homozygous state. Since the inheritance of the trait is comparable to that of a monogenic trait, it is advantageous in that the trait can easily be incorporated into various plant types for a given plant species.

In this application the term "modification" refers to changes to the wild type NXS gene and/or wild type regulatory sequences thereof that lead to a "modified" version of the wild type gene. A "gene" in the context of this application may comprise exonic sequences and regulatory sequences such as a promoter sequence and if present also may comprise intronic sequences. Modifications to the NXS gene and/or regulatory sequences thereof, may inhibit gene transcription such that the expression of the modified gene is reduced or prevented. Modifications may also be changes to the sequence of the NXS gene and/or regulatory sequences thereof that lead to a reduced level, reduced activity or complete absence of the encoded NXS protein.

The invention also relates to an NXS gene which may comprise a modification in its coding sequence and/or its regulatory sequences and/or splice sites as compared to the wild type sequence, wherein the modification results in an increase in the germination temperature of the seed which may comprise the modified gene in its genome. As used herein the "coding sequence" is the portion of the gene's DNA composed of exons that code for protein. As used herein "splice site" is a recognition site at which splicing of an intron takes place during the processing of pre-mRNA into mature mRNA. Splice sites are found at the 5' and 3' ends of introns. Splice sites are also intended to fall under the more general term "regulatory sequences". Modifications to the gene when recessive are to be present in homozygous state to be visible. Some of the modifications described herein are recessive and thus only confer the capability to germinate at an increased temperature as compared to a wild type seed to seeds having the modification in homozygous form. Modifications that are dominant or intermediate can also be visible in heterozygous state. This type of modification is also part of this invention.

In a particular embodiment the invention relates to a lettuce NXS gene which may comprise a modification in its coding sequence and/or its regulatory sequences and/or splice sites as compared to the wild type sequence of SEQ ID No. 1, wherein the modification results in an increase in the germination temperature of the seed which may comprise the modified gene.

Examples of gene modification techniques, types of modifications and more specifically, examples of modifications of the NXS gene, are described throughout this application. As used herein, wild type refers to the form of an organism, strain, gene, characteristic or trait as it would occur in nature, and is in contrast to the mutated form for example.

As previously mentioned, seed germination is strongly temperature dependent. Within a batch of seeds every single seed may or may not germinate at a particular temperature. Preferably all seeds or at least a high percentage of the seeds germinate at an optimum germination temperature range. If the temperature increases above the optimum germination temperature range, the germination percentage of a batch of seeds declines sharply. The germination temperature of a seed lot can be measured in terms of the "Germination Temperature 50" (GT50), which is the temperature at which 50% of the seeds of a given seed lot will germinate. When seeds of a given seed lot are exposed to temperatures above the GT50, they may become thermodormant or die. The GT50 may differ amongst different cultivars within a given crop.

"Seed lot" as used in this application is to mean, a batch of seeds produced from a mother plant. A seed lot consists preferably of a minimum of 100 seeds. When less than 100 seeds are used to determine the GT50 of a seed lot, the GT50 becomes less accurate.

Seed lots which may comprise seeds having a modified NXS gene, as well as their corresponding wild type seed lots, should be produced in the same production environment to be comparable. The skilled person is familiar with the production environment for different plant species. For example, lettuce seed lots in the context of the invention, i.e. with the GT50 values described herein, were produced at a latitude of 52°, in an Oceanic climate having a Koppen-classification of Cfb (McKnight & Hess, 2000. Physical Geography: A Landscape Appreciation. Upper Saddle River, N.J.: Prentice Hall).

The upper temperature cut-off point "GT50 Dark", as used in this application is to mean, the temperature at which 50% of the seeds of a given seed lot will germinate when sown on paper in the dark. The GT50 Dark is measured under continuous dark conditions (24 h/day) as this mimics germination conditions when seeds are planted beneath the soil or when seeds are encapsulated in pellets. Exposure of seeds belonging to the seed lot above the GT50 Dark, may cause the seeds to become thermodormant or die.

The skilled person is able to determine the GT50 Dark of a seed lot using a two step method. Firstly, germination tests are performed at different temperatures, in order to determine the cumulative germination percentage over time at a given temperature. For each seed lot to be tested, preferably 100 seeds are sown on top of a round filter paper wetted with tap water. These are in turn placed inside of a non-transparent plastic tray, which itself is lined with a large square piece of beet filter paper also wetted with tap water. A temperature recording device is placed on the beet filter paper to record the actual germination temperature at seed level. The tray is then closed with a well-fitted non-transparent lid, and placed inside a dark plastic bag. The tray is then placed inside a pre-heated incubator at the desired temperature. Biological replicates are preferably sown in different trays and at different points of time to remove any biases related to sowing.

All precautions should be taken to ensure that the germination tests are performed under dark conditions. Setting up tests, the incubations and germination scoring is performed preferably inside a thermostable room, which is closed from all outside light sources. Additionally, the thermostable room is lit with for example, with green safe lights (Philips TL-D 36 W/17 Green) to prevent any light effects on germination.

For a given temperature, germination is preferably scored twice a day. As used herein, "germination" occurs when radical protrusion is visible. Germinated seeds are counted and then removed at every counting moment. If there are dead or dormant seeds in the seed lot being tested, germination is followed for at least four extra counting moments until no additional germination is observed. The final germination percentage of a given seed lot, at a given temperature, can then be determined by plotting a "Germination over Time" curve. The final germination percentage is calculated as the number of germinated seeds at the end of scoring/the number of seeds sown for testing×100%. For example, if at the end of scoring, all seeds of the seed lot being tested germinate, then the final germination percentage is 100%. As used herein, the "final germination percentage" is the percentage of germination of a seed lot, after which no more germination occurs.

The final germination percentage from each "Germination over Time" curve is then plotted per actual measured temperature, for example in the case of lettuce from 18° C. to 42° C. (FIGS. 5A, 5B and 5C). A line of best fit is used for example, to fit the final germination percentages into a curve for each seed lot. The skilled person is familiar with this practice.

From the line of best fit, the GT50 Dark can be determined per seed lot. The GT50 Dark corresponds to the temperature at which the final germination percentage is expected to be 50%. When seeds of a given seed lot are exposed to temperatures above the GT50 Dark, they may become thermodormant or die.

In one embodiment, the invention relates to a seed lot wherein the seeds belonging to the seed lot may comprise a modified NXS gene and/or modified regulatory sequences, which when homozygously present in a seed, provides the seed with the capability to germinate at a high temperature, and which seed lot is characterized in that the GT50 Dark of said seed lot is at least 5° C. higher than the GT50 Dark of a seed lot of seeds not comprising the modified NXS gene and/or modified regulatory sequences thereof.

In another embodiment, the invention relates to a seed which may comprise in its genome a modified NXS gene and/or modified regulatory sequences, wherein said seed belongs to a seed lot having a GT50 Dark that is at least 5° C. higher than the GT50 Dark of a seed lot which may comprise seeds not having the modified NXS gene and/or modified regulatory sequences thereof.

The GT50 Dark of a seed lot of seeds having a modified NXS gene and/or modified regulatory sequences thereof or the germination temperature of the seed having a modified NXS gene and/or modified regulatory sequences thereof is between 5° C. and 25° C., between 6° C. and 25° C., between 7° C. and 25° C., between 8° C. and 25° C., between 9° C. and 25° C., between 10° C. and 25° C., between 11° C. and 25° C., between 12° C. and 25° C., between 13° C. and 25° C., between 14° C. and 25° C., between 15° C. and 25° C., between 16° C. and 25° C., between 17° C. and 25° C., between 18° C. and 25° C., between 19° C. and 25° C., between 20° C. and 25° C., between 21° C. and 25° C., between 22° C. and 25° C., between 23° C. and 25° C. and between 24° C. and 25° C. higher than the GT50 Dark of a seed lot of seeds or the germination temperature of the seed which does not have the modified NXS gene and/or modified regulatory sequences thereof of the invention. Increases of more than 25° C. also fall within the invention.

The said seed may comprise a modified NXS gene and/or modified regulatory sequences thereof, which when homozygously present, provides the seed with the capability to germinate at a high temperature, in particular at a temperature of at least 20° C.

The GT50 Dark of the seed lot or the germination temperature of the seed lies between 20° C. and 40° C., between 21° C. and 40° C., between 22° C. and 40° C., between 23° C. and 40° C., between 24° C. and 40° C., between 25° C. and 40° C., between 26° C. and 40° C., between 27° C. and 40° C., between 28° C. and 40° C., between 29° C. and 40° C., between 30° C. and 40° C., between 31° C. and 40° C., between 32° C. and 40° C., between 33° C. and 40° C., between 34° C. and 40° C., between 35° C. and 40° C., between 36° C. and 40° C., between 37° C. and 40° C., between 38° C. and 40° C., between 39° C. and 40° C.

For most plant species, 40° C. is the maximal biological temperature allowable for seed germination. This also means that the increase in GT50 Dark of a seed lot of seeds or the germination temperature of the seed which is provided by having a modified NXS gene and/or modified regulatory sequences thereof homozygously present in the genome of said seeds, will not provide said seeds with the capability to germinate beyond the biological maximum of 40° C., regardless of the relative increase provided by the modified NXS gene.

For some plant species, for example celery (*Apium graveolens*) or quinoa (*Chenopodium quinoa*), the GT50 Dark of a seed lot of seeds which may comprise a modified NXS gene and/or modified regulatory sequences thereof or the germination temperature of the seed which may comprise a modified NXS gene and/or modified regulatory sequences thereof may be lower than temperatures of at least 20° C. However, the GT50 Dark of a seed lot of seeds having a modified NXS gene and/or modified regulatory sequences thereof or the germination temperature of the seed having a modified NXS gene and/or modified regulatory sequences thereof is still between 5° C. and 25° C., between 6° C. and 25° C., between 7° C. and 25° C., between 8° C. and 25° C., between 9° C. and 25° C., between 10° C. and 25° C., between 11° C. and 25° C., between 12° C. and 25° C., between 13° C. and 25° C., between 14° C. and 25° C., between 15° C. and 25° C., between 16° C. and 25° C., between 17° C. and 25° C., between 18° C. and 25° C., between 19° C. and 25° C., between 20° C. and 25° C., between 21° C. and 25° C., between 22° C. and 25° C., between 23° C. and 25° C. and between 24° C. and 25° C. higher than the GT50 Dark of a seed lot of seeds or the germination temperature of the seed which does not have the modified NXS gene and/or modified regulatory sequences thereof of the invention. Increases of more than 25° C. also fall within the invention.

In one embodiment, the invention relates to a plant which may comprise a modified NXS gene and/or modified regulatory sequences thereof in its genome, which when homozygously present in a seed, provides the seed with the capability to germinate at a high temperature. The high temperature is as defined above.

In a particular embodiment, the invention relates to a seed lot of the species *Lactuca sativa* wherein the seeds belonging to the seed lot may comprise a modified NXS gene, which when homozygously present in a seed, provides the seeds in an unprimed state with the capability to germinate at a high temperature, and which seed lot is characterized in that the GT50 Dark of said seed lot is at least 10° C. higher than the GT50 Dark of a seed lot of seeds not comprising the modified NXS gene.

In an additional embodiment, the invention relates to a *Lactuca sativa* seed which may comprise in its genome a modified NXS gene, wherein said seed belongs to a seed lot having a GT50 Dark that is at least 10° C. higher than the GT50 Dark of a seed lot which may comprise seeds not having the modified NXS gene.

The GT50 Dark of a seed lot of seeds of the species *Lactuca sativa* having a modified NXS gene or the germination temperature of the seed having a modified NXS gene is between 10° C. and 25° C., between 11° C. and 25° C., between 12° C. and 25° C., between 13° C. and 25° C., between 14° C. and 25° C., between 15° C. and 25° C., between 16° C. and 25° C., between 17° C. and 25° C., between 18° C. and 25° C., between 19° C. and 25° C., between 20° C. and 25° C., between 21° C. and 25° C., between 22° C. and 25° C., between 23° C. and 25° C. and between 24° C. and 25° C. higher than the GT50 Dark of a seed lot of seeds or the germination temperature of the seed which does not have the modified NXS gene. Increases of more than 25° C. also fall within the invention.

The said *Lactuca sativa* seed may comprise a modified NXS gene, which when homozygously present, provides the seed in an unprimed state with the capability to germinate at a high temperature, in particular at a temperature of at least 31.8° C.

The GT50 Dark of the seed lot or the germination temperature of the seed lies between 28° C. and 40° C., between 31.8° C. and 40° C., between 32° C. and 40° C., between 33° C. and 40° C., between 34° C. and 40° C., between 35° C. and 40° C., between 36° C. and 40° C., between 37° C. and 40° C., between 38° C. and 40° C., between 39° C. and 40° C.

In a particular embodiment, the invention relates to a lettuce plant (*Lactuca sativa*) which may comprise a modified NXS gene, which when homozygously present in a seed, provides the seed in an unprimed state with the capability to germinate at a high temperature. The high temperature is as defined above.

Modifying the NXS gene and/or modified regulatory sequences thereof may lead to changes in the expression of the gene. In one embodiment, the invention relates to seed which may comprise in its genome a modified NXS gene and/or modified regulatory sequences thereof, wherein the expression of the modified NXS gene is substantially reduced or prevented and this reduction or prevention causes the seed to be able to germinate at a higher temperature than the wild type seed not comprising a modified NXS gene and/or modified regulatory sequences thereof. In a further embodiment, the invention relates to seed which may comprise in its genome a modified NXS gene and/or modified regulatory sequences thereof, wherein the expression of the modified NXS gene is reduced or prevented.

In another embodiment, the invention relates to a modified NXS gene and/or modified regulatory sequences thereof wherein the expression of said gene when present in the genome of a seed or plant is substantially reduced or prevented. In another embodiment, the invention relates to a modified NXS gene and/or modified regulatory sequences thereof wherein the expression of said gene is reduced or prevented.

When the expression of the NXS gene is reduced or prevented in the context of this invention, this is to mean that the expression of the modified NXS gene is less than the expression of the wild type NXS gene or is prevented and thus absent. In the context of the invention, the said reduction or prevention of gene expression is directly or indirectly responsible for the trait of high temperature germination of the invention.

In a more particular embodiment, the invention relates to lettuce (*Lactuca sativa*) seed which may comprise in its genome a modified NXS gene, wherein the expression of the modified NXS gene is substantially reduced or prevented.

In general, gene expression may be reduced or prevented by means of preventing the transcription of the gene. Preventing transcription may for example be achieved by means of RNA oligonucleotides, DNA oligonucleotides or RNAi molecules directed against the NXS gene promoter, or preferably by means of the expression of a negatively acting transcription factor acting on the NXS gene promoter. Gene expression may also be reduced or prevented by destabilizing NXS mRNA or transcript, preferably by means of nucleic acid molecules that are complementary to the NXS mRNA or transcript, selected from the group consisting of antisense RNA, RNAi molecules, Virus-Induced Gene Silencing (VIGS) molecules, co-suppressor molecules, RNA oligonucleotides or DNA oligonucleotides. Such methods for destabilizing mRNA or transcripts are well known to the person skilled in the art.

In a further embodiment, the invention relates to seed having a reduced level, reduced activity or complete absence of NXS protein. In one embodiment, the invention relates to seed having a reduced level, reduced activity or complete absence of NXS protein, resulting from a modification of the NXS gene and/or modified regulatory sequences thereof which encodes it. In another embodiment, the invention relates to a modified NXS gene and/or modified regulatory sequences thereof, characterized in that seed which may comprise said modified gene and/or modified regulatory sequences thereof have a reduced level, reduced activity or complete absence of the encoded NXS protein. A reduced level or complete absence of the NXS protein may occur by disrupting the transcription of the NXS gene, for example by introducing one or more mutations in the NXS gene promoter sequence. A reduced activity of the NXS protein may occur for example by introducing one or more mutations into the coding sequence of the NXS gene. Mutation(s) to the NXS gene may affect the biological function of the encoded protein, as compared to NXS protein encoded by a wild type NXS gene where no such mutation(s) is present.

In a more particular embodiment, the invention relates to lettuce (*Lactuca sativa*) seed having a reduced level, reduced activity or complete absence of NXS protein.

In the course of research that led to the present invention, lettuce seeds that germinate at a high temperature were identified to comprise a mutation in the NXS gene. One of the identified mutations led to a premature stop codon in the coding sequence of the lettuce NXS gene (FIGS. 1A-B, SEQ ID No. 1). Another mutation led to an amino acid substitution in a highly conserved residue of the lettuce NXS protein (FIG. 1C, SEQ ID No. 2). In one embodiment, the invention relates to lettuce seed which may comprise in its genome a modified NXS gene, wherein the modified NXS gene may comprise a premature stop codon. In another embodiment, the invention relates to lettuce seed which may comprise in its genome a modified NXS gene, wherein the modified NXS gene encodes an NXS protein that may comprise one or more amino acid substitutions.

Both types of mutations provided the respective mutant lettuce seeds with the ability to germinate at a high temperature, which is well above the germination temperature for the corresponding wild type lettuce seeds (see Examples 1-3 and FIG. 5A, 5B, 5C). It was found that the modification to the NXS gene wherein a conserved proline residue is substituted with a serine residue, provided the seeds with a significantly higher capability to germinate at a high temperature as compared to the wild type seed. The modification to the NXS gene wherein a premature stop codon is introduced also increases the germination temperature (see Table 2 of Example 3B showing the relative increase in GT50 Dark between mutant seed lots and wild type seed lots, and Example 4).

While the NXS mutations that have been identified in the course of this research illustrate the causative effect between the aforementioned mutations of the lettuce NXS gene and the trait of the invention, these are certainly not the only mutations of the NXS gene that would lead to the trait of the invention and should not be limited as such.

Thus in one embodiment, the invention relates to seed which may comprise in its genome a modified NXS gene, wherein the modified NXS gene may comprise a premature stop codon. In another embodiment, the invention relates to a modified NXS gene wherein said gene may comprise a premature stop codon.

In a particular embodiment, the invention relates to lettuce seed having a modified NXS gene, wherein the modification is a premature stop codon located within exon 3, exon 4, or exon 5 of the lettuce NXS gene according to SEQ ID No. 1. More in particular, the premature stop codon is the result of a mutation of residue $G_{3018}>A_{3018}$ of the lettuce NXS gene according to SEQ ID No. 1.

In one embodiment, the invention relates to seed which may comprise in its genome a modified NXS gene, wherein the modified NXS gene encodes an NXS protein that may comprise one or more amino acid substitutions. In another embodiment, the invention relates to a modified NXS gene wherein said gene encodes an NXS protein that may comprise one or more amino acid substitutions.

In lettuce two types of mutations were identified that both led to an increase in the germination temperature. Both mutations were in the NXS gene. In addition to this, the skilled person is very well capable of introducing other mutations that have the same or a similar effect on the germination temperature in an NXS gene of lettuce or another crop. By using the germination tests as described herein it can be established whether the germination temperature is higher than in the wild type, i.e. the plant not comprising a modified NXS gene. This observation in lettuce is thus more broadly applicable to other crops that have an NXS gene.

Mutation(s) in the NXS gene and/or regulatory sequences thereof are preferably introduced randomly by means of one or more chemical compounds, such as ethyl methane sulphonate (EMS), nitrosomethylurea, hydroxylamine, proflavine, N-methly-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast neutron exposure, X-rays, gamma irradiation, and/or by insertion of genetic elements, such as transposons, T-DNA, retroviral elements. Mutagenesis also may comprise the more specific, targeted introduction of at least one modification by means of homologous recombination, oligonucleotide-based mutation introduction, zinc-finger nucleases (ZFN), transcription activator-like effector nucleases (TALENs) or Clustered Regularly Interspaced Short Palindromic Repeat (CRISPR) systems.

Examples of mutations that may lead to a reduced activity of the NXS protein are mutations to the NXS coding sequence that give rise to premature stop codons, frame shifts or amino acid changes in the encoded protein. Premature stop codons typically lead to the expression of a truncated version of the encoded protein. Depending on the position of the mutation in the coding sequence, a truncated version of a protein may lack one or more domains that are essential to perform its function and/or to interact with substrates or with other proteins, and/or it may lack the ability to fold properly into a functional protein.

Frame shift mutations are caused by the introduction or deletion of one or more base pairs in a DNA sequence encoding a protein. When the number of inserted or deleted base pairs at a certain position is not a multiple of 3, the triplet codon encoding the individual amino acids of the protein sequence become shifted relative to the original open-reading frame, and the encoded protein sequence changes dramatically. Protein translation will result in an entirely different amino acid sequence than that of the originally encoded protein, and often a frame shift also leads to a premature stop codon in the open reading frame. The overall result is that the encoded protein no longer has the same biological function as the originally encoded protein.

Amino acid changes in an encoded protein sequence arise when the mutation of one or more base pairs in the coding sequence results in an altered triplet codon, encoding a different amino acid. Due to the redundancy of the genetic code not all point mutations lead to amino acid changes. Such mutations are termed "silent mutations". Some amino acid changes are "conservative", i.e. they lead to the replacement of one amino acid by another amino acid with comparable properties, such that the mutation is unlikely to dramatically change the folding of the mature protein, or influence its function. Other amino acid changes are non-silent, non-conservative amino acid changes in domains that play a role in substrate-recognition, the active site of enzymes, interaction domains or in major structural domains (such as transmembrane helices) may partly or completely destroy the functionality of an encoded protein, without thereby necessarily affecting the expression level of the encoding gene. As used herein, a "non-conservative amino acid change" occurs when one amino acid is replaced by another amino acid with different chemical properties, which may lead to detrimental stability, functionality and/or structural effects of the encoded protein.

Mutations in the promoter sequence of the NXS gene may also perturb the biological function of the encoded NXS protein, as such mutations may lead to a complete lack of transcription of the gene (e.g. subsequently resulting in a complete absence of the NXS protein), or to a significantly decreased and biologically inadequate level of transcription (e.g. subsequently resulting in a reduced level of the NXS protein). Mutations in splice sites may also perturb the biological function of the encoded protein, because if a splice site is destroyed by a mutation, the amino acid sequence encoded in the mature mRNA transcribed from the gene will not be correct, and it may easily contain frame shifts and/or premature stop codons. In either case, the protein sequence translated from such an mRNA will not be identical to the originally encoded protein sequence, which will most likely have serious consequences for the biological functionality of the translated protein.

As previously mentioned, certain amino acid substitutions produce a conservative change and result in a functionally equivalent protein. Conservative amino acid substitutions may be made on the basis of chemical properties, for example similarity in polarity, charge, solubility, hydrophobicity, hydrophilicity or the amphipathic nature of the residues, in which case the resulting protein may still function normally. The amino acid substitution may occur in a region of the protein that does not significantly affect the protein structure or function. Conversely, an amino acid substitution that occurs at a well conserved or invariant position that is essential for the structure and/or function of the protein, or substitutions with amino acids that do not share conserved chemical properties (e.g. hydrophobic vs. charged vs. polar), may lead to non-conservative amino acid changes.

In a preferred embodiment, the invention relates to seed which may comprise in its genome a modified NXS gene, wherein the modified NXS gene may comprise a premature stop codon and/or encodes an NXS protein that may comprise one or more amino acid substitutions. In another preferred embodiment, the invention relates to a modified NXS gene wherein said gene may comprise a premature stop codon and/or encodes an NXS protein that may comprise one or more amino acid substitutions.

Multiple sequence alignments between orthologous NXS protein reveals highly conserved positions that may be relevant to the stability, function and/or structure of the NXS protein (FIGS. 4A-C). Modification of conserved residues is likely to cause changes in the expression level or activity of the protein. In one embodiment, the invention relates to seed which may comprise in its genome a modified NXS gene, wherein a conserved residue of the encoded NXS protein is substituted. In another embodiment, the invention relates to a modified NXS gene wherein said gene encodes a NXS protein in which a conserved residue is substituted. Mutations in the NXS gene leading to non-conservative amino acid changes at these conserved positions in the encoded protein, lead to a reduced level, reduced activity or complete absence of NXS protein.

In a further embodiment, the conserved residue is in particular a proline residue which was found to be very highly conserved in a multiple sequence alignment of the NXS protein of more than 200 unrelated species (results not shown). Preferably, this conserved proline is substituted with a serine residue, or any other non-conservative amino acid change which would disrupt the stability, functionality, and/or structure of the encoded NXS protein. The skilled person is familiar with substitutions which would be non-conservative amino acid changes for a given amino acid.

More in particular, the invention relates to a modified lettuce NXS gene, wherein a highly conserved proline residue at position 212 in the lettuce NXS protein (SEQ ID No. 2) which is encoded by $C_{3518}C_{3519}A_{3520}$ of the lettuce NXS DNA sequence (SEQ ID No. 1) is substituted with a serine residue ($C_{3518}C_{3519}A_{3520}$>$T_{3518}C_{3519}A_{3520}$).

In another embodiment, the conserved residue is in particular a tryptophan residue which was found to be very highly conserved in a multiple sequence alignment of the NXS protein of more than 200 unrelated species (results not shown).

More in particular, in lettuce the conserved tryptophan is located at position 175 in the lettuce NXS protein (SEQ ID No. 2) which is encoded by $T_{3196}$ $G_{3197}$ $G_{3198}$ of the lettuce NXS DNA sequence (SEQ ID No. 1). Preferably, this conserved tryptophan is substituted with any other non-conservative amino acid change which would disrupt the stability, functionality, and/or structure of the encoded NXS protein.

A seed of the invention is also a seed in which an orthologous NXS gene and/or regulatory sequences thereof is suitably modified, wherein the modified NXS gene and/or modified regulatory sequences thereof provides the seed with the capability to germinate at a high temperature, for example a seed selected from any of the species *Lactuca sativa, Cichorium endivia, Cichorium intybus, Solanum melongena, Solanum lycopersicum, Capsicum annuum, Capsicum baccatum, Brassica oleracea, Apium graveolens, Spinacia oleracea, Valerianella locusta, Daucus carota, Glycine max, Rhaphanus sativus, Chenopodium quinoa, Vigna radiata, Medicago sativa, Cicer arietinum, Fagopyrum esculentum, Trigonella foenum-graecum, Allium cepa, Lens esculenta, Oryza sativa, Zea mays, Phaseolus vulgaris, Pisum sativum, Vitis vinifera, Triticum aestivum*, and/or *Hordeum vulgare*. It is not intended to claim *Nicotiana tabacum* (tobacco) or *Arabidopsis thaliana* seeds in this application.

The invention further relates to a plant which may comprise in its genome a modified NXS gene and/or modified regulatory sequences thereof, which when homozygously present in a seed, provides the seed with the capability to germinate at a high temperature as compared to wild type seed not having the modified NXS gene and/or modified regulatory sequences thereof in homozygous form. The modification(s) to the NXS gene and/or encoded protein results in a substantial reduction or prevention of gene expression and/or reduced activity or complete absence of NXS protein, as described above for the seed of the invention which may comprise a modified NXS gene.

Accordingly, a plant of the invention is a plant that is grown from seed exhibiting the trait of the invention, or a plant that produces seeds exhibiting the trait of the invention. In the latter case, both parents of the seeds should have a modified NXS gene and/or modified regulatory sequences thereof.

A plant of the invention is also a plant in which an orthologous NXS gene and/or regulatory sequences thereof is suitably modified, which modification when present in a seed, provides the seed with the capability to germinate at a high temperature, for example a plant selected from any of the species *Lactuca sativa, Cichorium endivia, Cichorium intybus, Solanum melongena, Solanum lycopersicum, Capsicum annuum, Capsicum baccatum, Brassica oleracea, Apium graveolens, Spinacia oleracea, Valerianella locusta, Daucus carota, Glycine max, Rhaphanus sativus, Chenopodium quinoa, Vigna radiata, Medicago sativa, Cicer arietinum, Fagopyrum esculentum, Trigonella foenum-graecum, Allium cepa, Lens esculenta, Oryza sativa, Zea mays, Phaseolus vulgaris, Pisum sativum, Vitis vinifera, Triticum aestivum*, and/or *Hordeum vulgare*. It is not intended to claim *Nicotiana tabacum* (tobacco) or *Arabidopsis thaliana* plants in this application.

In one embodiment, the plant of the invention is a lettuce plant (*Lactuca sativa*) which may comprise in its genome a modified NXS gene, which when homozygously present in an unprimed seed, provides the seed with the capability to germinate at a high temperature as compared to wild type seed not having the modified NXS gene.

The genetic modifications leading to substantially reduced or prevented NXS gene expression and/or a reduced level, reduced activity or complete absence of the NXS protein, when recessive, result in the capability of a seed to germinate at a high temperature, once the modified NXS gene and/or modified regulatory sequences thereof is homozygously present in the plant. A modified NXS gene and/or modified regulatory sequences thereof can be introgressed from a plant which may comprise the modified NXS gene and/or modified regulatory sequences thereof into a plant lacking the modified NXS gene and/or modified regulatory sequences thereof but having other desired traits, using crossing when the plants are sexually compatible, optionally combined with techniques that aid the development of viable seeds or facilitate development into a plant. The desired traits of the plant lacking the modified NXS gene and/or modified regulatory sequences thereof can be selected from, but are not limited to, the following group: resistance to bacterial, fungal, or viral diseases, insect or pest resistance, plant size, plant type, improved shelf-life, water stress, heat tolerance, parthenocarpy and sterility. In a particular embodiment, a modified lettuce NXS gene can be introgressed from a *Lactuca sativa* plant which may comprise the modified lettuce NXS gene into a *Lactuca sativa* plant lacking the modified lettuce NXS gene and/or modified regulatory sequences thereof using standard breeding techniques.

Selection for plants that have obtained the high germination trait of the invention from a plant which may comprise the modified NXS gene and/or modified regulatory sequences thereof is started in the F1 or any further generation from a cross between the obtaining plant and a source plant by using a molecular marker that is based upon the modification to the NXS gene and/or modified regulatory sequences thereof that underlies the trait. The skilled person is familiar with creating and using molecular markers to identify such modifications. In a particular embodiment examples of suitable molecular markers are the SNP $C_{3518}>T_{3518}$ and the SNP $G_{3018}>A_{3018}$ in the NXS gene of lettuce (*Lactuca sativa*) according to SEQ ID No. 1.

Alternatively, selection for the modified NXS gene and/or modified regulatory sequences thereof is started in the F2 of a cross or alternatively of a backcross. Selection of plants in the F2 can also be done phenotypically based on germination tests performed on the F3 seed lots, as well as by using a molecular marker(s) which directly or indirectly detect(s) the modification of the NXS gene and/or modified regulatory sequences thereof that underlies the trait.

Selection for plants having the modified NXS gene, which when homozygously present in a seed provides the seed with the capability to germinate at a high temperature, can also be started in the F3 or a later generation.

Crossing can optionally be followed by embryo rescue techniques or other techniques that result in a successful combination and introgression, which techniques are known to the person skilled in the art.

The invention further relates to progeny of a plant which may comprise a modified NXS gene and/or modified regulatory sequences thereof, which when homozygously present in a seed, provides the seed with the capability to germinate at a high temperature. Such progeny can be produced by sexual or vegetative reproduction of a plant of the invention or a progeny plant thereof. The progeny carries the modified NXS gene and/or modified regulatory sequences thereof that causes the trait of the invention.

When the modified NXS gene and/or modified regulatory sequences thereof is homozygously present in a seed of the progeny plant, the seed has the capability to germinate at a high temperature in the same way as or in a way similar to a seed of the plant of the invention.

As used herein, "progeny" is intended to mean the offspring or the first and all further descendants from a cross with a plant of the invention that shows the trait of the invention and/or carries the modified NXS gene and/or modified regulatory sequences thereof underlying the trait.

In one embodiment, the invention relates to plants that carry the trait of the invention and that have acquired the said trait by introduction of the modified NXS gene and/or modified regulatory sequences thereof that is responsible for the trait from a suitable source, either by conventional breeding, or genetic modification, in particular by cisgenesis or trans-genesis. Cis-genesis is genetic modification of plants with a natural gene, encoding an (agricultural) trait from the crop plant itself or from a sexually compatible donor plant. Trans-genesis is a genetic modification of a plant with a gene from a non-crossable species or with a synthetic gene.

The invention also relates to propagation material suitable for producing a plant which may comprise in its genome a modified NXS gene and/or modified regulatory sequences thereof, which when homozygously present in a seed, provides the seed with the capability to germinate at a high temperature.

In one embodiment, the propagation material is suitable for sexual reproduction. Such propagation material may comprise for example microspores, pollen, ovaries, ovules, embryo sacs and egg cells. In another embodiment, the propagation material is suitable for vegetative reproduction. Such propagation material may comprise for example cuttings, roots, stems, cells, protoplasts, and in particular leaves, pollen, embryos, cotyledons, hypocotyls, meristematic cells, root tips, anthers, flowers, seeds and stems.

The invention further relates to a plant grown or regenerated from the said propagation material of a plant of the invention, which plant may comprise in its genome a modified NXS gene and/or modified regulatory sequences thereof as defined herein, wherein the modified NXS gene and/or modified regulatory sequences thereof which when homozygously present in a seed, provides the seed with the capability to germinate at a high temperature.

The invention further relates to a cell of a plant of the invention, which cell may comprise a modified NXS gene and/or modified regulatory sequences thereof, which when homozygously present in a seed, provides the seed with the capability to germinate at a high temperature. Preferably, the cell of the invention is part of a plant or plant part, but the cell may also be in isolated for.

The invention also relates to a cell of a plant of the invention, which cell may comprise a modified NXS gene and/or modified regulatory sequences thereof in its genome, which when homozygously present in a seed, provides the seed with the capability to germinate at a high temperature.

The invention also relates to the use of a plant of the invention that may comprise a modified NXS gene and/or modified regulatory sequences thereof, which when homozygously present in a seed, provides the seed with the capability to germinate at a high temperature, as a crop.

The invention also relates to the use of a plant of the invention that may comprise a modified NXS gene and/or modified regulatory sequences thereof, which when homozygously present in a seed, provides the seed with the capability to germinate at a high temperature, as a source of seed.

The invention also relates to the use of a plant of the invention that may comprise a modified NXS gene and/or modified regulatory sequences thereof, which when homozygously present in a seed, provides the seed with the capability to germinate at a high temperature, as a source of propagating material.

The invention also relates to the use of a plant of the invention that may comprise a modified NXS gene and/or modified regulatory sequences thereof, which when homozygously present in a seed, provides the seed with the capability to germinate at a high temperature, for consumption.

The invention also relates to the use of a plant of the invention that may comprise a modified NXS gene and/or modified regulatory sequences thereof, which when homozygously present in a seed, provides the seed with the capability to germinate at a high temperature, in plant breeding.

The invention further relates to the use of a seed of the invention that may comprise in its genome a modified NXS gene and/or modified regulatory sequences thereof, which when homozygously present in the seed, provides the seed with the capability to germinate at a high temperature, for sprouting. The term "sprouting" is to mean the practice of germinating a seed for consumption.

The invention further relates to the use of a sprouted seed of the invention that may comprise in its genome a modified NXS gene and/or modified regulatory sequences thereof, which when homozygously present in the seed, provides the seed with the capability to germinate at a high temperature, for consumption. The term "sprouted seed" is to mean a germinated seed which can be eaten raw or cooked. Examples of sprouted seeds that may be eaten raw or cooked may include, but are not limited to the sprouted seeds of the species *Rhaphanus sativus, Chenopodium quinoa, Vigna radiata, Medicago sativa, Cicer arietinum, Fagopyrum esculentum, Trigonella foenum-graecum, Allium cepa, Lens esculenta, Phaseolus vulgaris*, and *Pisum sativum.*

The invention further relates to a method for producing seeds that are capable of germinating at a high temperature, which may comprise modifying the NXS gene and/or regulatory sequences thereof of the seed to lower the expression level of the gene, to prevent expression of the gene and/or to lower the activity of the encoded NXS protein. Suitably the modification is achieved by mutating the gene. Mutation is suitably performed on seeds, in particular on seeds that have in their genome a wild type version of the NXS gene.

In one embodiment the plant which may comprise the modified NXS gene and/or modified regulatory sequences thereof is a plant of an inbred line, a hybrid, a doubled haploid, or of a segregating population.

The invention further provides a method for the production of a plant having the modified NXS gene and/or modified regulatory sequences thereof, which when homozygously present in a seed provides the seed with the capability to germinate at a high temperature, by using a doubled haploid generation technique to generate a doubled haploid line which may comprise the high temperature germination trait.

The invention furthermore relates to hybrid seed having the modified NXS gene and/or modified regulatory sequences thereof, which when homozygously present in a seed provides the seed with the capability to germinate at a high temperature, and to a method for producing such hybrid seed which may comprise crossing a first parent plant with a second parent plant and harvesting the resultant hybrid seed, wherein said first parent plant and said second parent plant is a plant that carries at least one allele of the modified NXS gene and/or modified regulatory sequences thereof. When the two parents both have the modified NXS gene and/or modified regulatory sequences thereof they suitably differ in one or more, preferably multiple, other traits.

The invention also relates to a method for the production of a plant having the modified NXS gene and/or modified regulatory sequences thereof, which when homozygously present in a seed provides the seed with the capability to germinate at a high temperature, by using a seed that may comprise the modified NXS gene and/or modified regulatory sequences thereof for growing the said plant.

The invention also relates to a method for seed production which may comprise growing plants from seeds of the invention, allowing the plants to produce seeds, and harvesting those seeds. Production of the seeds is suitably done by crossing or selfing. Preferably, the seeds so produced have the capability to germinate at a high temperature. For this, both parents should have the modified NXS gene and/or modified regulatory sequences thereof.

In one embodiment, the invention relates to a method for the production of a plant having the modified NXS gene and/or modified regulatory sequences thereof, which when homozygously present in a seed provides the seed with the capability to germinate at a high temperature, by using tissue culture.

The invention furthermore relates to a method for the production of a plant having the modified NXS gene and/or modified regulatory sequences thereof, which when homozygously present in a seed provides the seed with the capability to germinate at a high temperature, by using vegetative reproduction.

The present invention is broadly applicable to all plant species and crops that harbour an NXS gene in their genome. Identification of NXS orthologues, i.e. NXS genes in other species, can be performed in many crops, methods for which are known in the art. In the present research, a Basic Local Alignment Search Tool (BLAST) program was used to compare the lettuce NXS DNA and protein sequence (FIGS. 1A-C, SEQ ID No. 1 and 2) against sequences of other plant genomes. This resulted in 1-2 best hits per species and these were identified as candidate NXS orthologous genes. Primers were then designed to amplify the complete NXS gene. For some plant species, orthologous NXS protein sequence were identified by Blast X or Blast P as reciprocal best hits to the lettuce NXS or other plant NXS protein sequences. DNA and protein sequences of the NXS orthologues that were identified through this method are represented in FIGS. 2A-2GG, FIGS. 3A-F and Table 1. Multiple sequence alignments of the protein sequences confirmed that these were orthologous NXS genes (FIGS. 4A-C).

Once the DNA sequence of orthologous NXS genes are known, this information may be used to modulate or modify the expression of said genes by methods herein described. In one embodiment, the invention relates to modified versions of the NXS genes and/or modified regulatory sequences thereof of *Lactuca sativa, Cichorium endivia, Cichorium intybus, Solanum melongena, Solanum lycopersicum, Capsicum annuum, Capsicum baccatum, Brassica oleracea, Apium graveolens, Spinacia oleracea, Valerianella locusta, Daucus carota, Glycine max, Rhaphanus sativus, Chenopodium quinoa, Vigna radiata, Medicago sativa, Cicer arietinum, Fagopyrum esculentum, Trigonella foenum-graecum, Allium cepa, Lens esculenta, Oryza sativa, Zea mays, Phaseolus vulgaris, Pisum sativum, Vitis vinifera, Triticum aestivum*, and/or *Hordeum vulgare.*

When in the present application it is stated that the modified NXS gene "when homozygously present" provides seeds with the capability to germinate at a high temperature this is intended to encompass situations in which the modification is recessive but also situations in which the modification is dominant and the high temperature germination capacity is also expressed when the modified gene is present in heterozygous state. Such dominant modifications can be but need not be present in homozygous state but are also visible in heterozygous state. Seeds and plants having such dominant modification and their uses are also part of this invention.

An overview of the NXS orthologues are presented in Table 1. The overview indicates which SEQ ID Nos are linked to which plant species in FIGS. 2A-2GG, 3A-F and 4A-C. For some plant species, a GI number (GenInfo identifier) and Genbank Accession number is listed, which can be used to retrieve corresponding orthologous NXS sequence.

TABLE 1

| Species | Detail | GI number | GenBank Accession No. | SEQ ID No. in FIGS. 2A-2GG | SEQ ID No. in FIGS. 3A-F |
|---|---|---|---|---|---|
| *Zea mays* | mRNA | 670383460 | XM_008674309 | — | — |
| *Phaseolus vulgaris* | mRNA | 593331455 | XM_007139092 | — | — |
| *Citrus sinesis* | mRNA | 572153068 | NP_001275861 | — | — |
| *Glycine Max*-1 | mRNA | 571474665 | XP_006586290 | — | — |
| *Glycine Max*-2 | mRNA | 571550275 | XM_003552678.2 | — | — |
| *Glycine Max*-3 | Misc_RNA | 571554555 | XR_137640.2 | — | — |
| *Populus trichocarpa* | mRNA | 566165809 | XP_002305164 | — | — |
| *Malus domestica* | mRNA | 372477763 | AEX97076 | — | — |
| *Oryza sativa* | mRNA | 297596023 | NP_001041911 | — | — |
| *Ricinis communis* | mRNA | 255560414 | XP_002521222 | — | — |
| *Vitis vinifera* | mRNA | 225452043 | XP_002283875 | — | — |
| *Triticum aestivum* | protein | 669027321 | CDM80641 | — | — |
| *Cicer arietinum* | mRNA | 502180568 | XP_004516667 | — | — |
| *Daucus carota* (variant 1) | Genomic DNA | Sequence described in this application | | 3 | 30 |
| *Daucus carota* (variant 2) | Genomic DNA | Sequence described in this application | | 4 | 31 |
| *Chicorium endivia* | Genomic DNA | Sequence described in this application | | 5 | 32 |
| *Solanum melongena* (variant 1) | Genomic DNA | Sequence described in this application | | 6 | 33 |
| *Solanum melongena* (variant 2) | Genomic DNA | Sequence described in this application | | 7 | 34 |
| *Solanum lycopersicum* (variant 1) | Genomic DNA | Sequence described in this application | | 8 | 35 |
| *Solanum lycopersicum* (variant 2) | Genomic DNA | Sequence described in this application | | 9 | 36 |
| *Capsicum annuum* | Genomic DNA | Sequence described in this application | | 10 | 37 |
| *Brassica oleracea* | Genomic DNA | Sequence described in this application | | 11 | 38 |

TABLE 1-continued

| Species | Detail | GI number | GenBank Accession No. | SEQ ID No. in FIGS. 2A-2GG | SEQ ID No. in FIGS. 3A-F |
|---|---|---|---|---|---|
| *Apium graveolens* (variant 1) | Genomic DNA | Sequence described in this application | | 12 | 39 |
| *Apium graveolens* (variant 2) | Genomic DNA | Sequence described in this application | | 13 | 40 |
| *Spinacia oleracea* | Genomic DNA | Sequence described in this application | | 14 | 41 |
| *Valerianella locusta* | Genomic DNA | Sequence described in this application | | 15 | 42 |
| *Rhaphanus sativus* | Genomic DNA | Sequence described in this application | | 16 | 43 |
| *Capsicum baccatum* | Genomic DNA | Sequence described in this application | | 17 | 44 |
| *Chenopodium quinoa* | Genomic DNA | Sequence described in this application | | 18 | 45 |
| *Fagopyrum esculentum* | CDS | Sequence described in this application | | 19 | 46 |
| *Lens esculenta* | Genomic DNA | Sequence described in this application | | 20 | 47 |
| *Medicago sativa* | Genomic DNA | Sequence described in this application | | 21 | 48 |
| *Pisum sativum* | CDS | Sequence described in this application | | 22 | 49 |
| *Vigna radiata* (variant 1) | Genomic DNA | Sequence described in this application | | 23 | 50 |
| *Vigna radiata* (variant 2) | CDS | Sequence described in this application | | 24 | 51 |
| *Trigonella foenum-graecum* | Genomic DNA | Sequence described in this application | | 25 | 52 |
| *Chicorium intybus* | Genomic DNA | Sequence described in this application | | 26 | 53 |
| *Allium cepa* (variant 1) | CDS | Sequence described in this application | | 27 | 54 |
| *Allium cepa* (variant 2) | CDS | Sequence described in this application | | 28 | 55 |
| *Hordeum vulgare* | CDS | Sequence described in this application | | 29 | 56 |

CDS = coding DNA sequence

EXAMPLES

Example 1

Genetic Modification of Sensaï and Burovia Lettuce Seeds by Ethyl Methane Sulfonate (EMS)

Seeds of the wild type lettuce varieties Sensaï and Burovia RZ (both from Rijk Zwaan, De Lier, The Netherlands) were treated with EMS by submergence of approximately 2000 seeds per variety into an aerated solution of either 0.5% (w/v) or 0.7% EMS for 24 hours at room temperature.

Approximately 1500 treated seeds per variety per EMS dose were germinated and the resulting plants were grown in a greenhouse in The Netherlands (e.g. 52° latitude, Oceanic climate, Koppen-classification Cfb) from May to September to produce seeds.

Following maturation, M2 seeds were harvested and bulked in one pool per variety per treatment. The resulting four pools of M2 seeds were used as starting material to identify the individual M2 seeds containing high temperature germination alleles.

The efficacy of the genetic modification procedure was assessed by determining the occurrence of bleached plants, which is indicative for chlorophyll loss due to modification in genes directly or indirectly involved in the formation or accumulation of chlorophyll. Individual plants within each of the 4 pools of M2 seeds were observed to be bleached. This demonstrates that the applied treatments resulted in genetic modifications.

Example 2

Identification of Sensaï and Burovia Lettuce Seeds Capable of Germinating at a High Temperature Lettuce seeds capable of germinating at a high temperature were identified amongst the M2 seeds that were produced as a result of the EMS treatment described in Example 1.

Of each of the available M2 pools, approximately 2000 seeds were germinated on wetted filter paper in a closed container. The M2 seeds of Burovia were incubated at 35° C., whilst the M2 seeds of Sensai were incubated at 32° C., under continuous dark conditions (24 h/day) in order to mimic natural germination conditions beneath the soil or when seeds are encapsulated in pellets.

Any seeds that germinated at the given temperatures were grown into plants. These plants were self-fertilised to produce M3 seed. The M3 seeds were again germinated at 34° C. or 35° C. under continuous dark conditions, to confirm the presence of high temperature germination alleles.

The confirmed M3 seeds were grown into M3-lines which were then multiplied.

Example 3A

Seed Germination Testing of Sensaí and Burovia Wild Type and Mutant Lettuce Seeds Germination tests were performed at different temperatures, to determine the cumulative germination over time at a given temperature for each seed lot of wild type lettuce varieties Sensaï and Burovia, as well as the EMS treated seeds of the deposit (obtained in Example 2).

For each seed lot, 100 seeds were sown on top of round filter paper, which was wetted with tap water. The seeds sown on the round filter paper were in turn placed inside a non-transparent plastic tray, which itself was lined with a large square piece of beet filter paper wetted with tap water. Additionally, a temperature recording device was placed on the beet filter paper to record the actual germination temperature at seed level. The tray was then closed with a well-fitted non-transparent lid, and wrapped inside a layer of dark plastic. The trays were placed inside a pre-heated incubator at the desired temperature. The germination tests were conducted from 18° C. to 42° C. Biological replicates were sown in different trays and preferably at different points in time to remove any biases related to sowing.

All precautions were taken to ensure that the germination tests were performed under dark conditions. Setting up of the germination tests, the incubations and the germination scoring were all performed inside a thermostable room, closed from all outside light sources. In order to prevent any light effects on the germination, the room was lit with green safe lights (Philips TL-D 36 W/17 Green).

For a given temperature, germination was scored twice a day. A seed was scored as being germinated when radical protrusion through the pericarp of the seed was clearly visible. Germinated seeds were counted and then removed at every counting moment. If there were dead or dormant seeds in the seed lot being tested, germination was followed for at least four extra counting moments until no additional germination was observed. The final germination percentage of a given seed lot, at the given temperature, was determined by plotting a "Germination over Time" curve. The final germination percentage was calculated as the number of germinated seeds at the end of scoring/the number of seeds sown for testing×100%.

Example 3B

Determining the GT50 Dark of Sensaï and Burovia Wild-type and Mutant Seed Lots

To determine the GT50 Dark of a given seed lot, the final germination percentage from each "Germination over Time" curve from Example 3A, was plotted per actual measured temperature, from 18° C. to 42° C. (FIGS. 5A, 5B and 5C). A line of best fit was used to fit the final germination percentages into a curve.

The GT50 Dark was derived per seed lot, by determining the temperature at which the final germination percentage is expected to be 50% (Table 2). When seeds of a given seed lot are exposed to temperatures above the GT50 Dark, they may become thermodormant or die.

It is clear from Table 2 and FIGS. 5A, 5B and 5C (Relative increase in GT50 Dark between mutant seed lots and wild type seed lots) that the GT50 Dark of the seed lots which may comprise unprimed seeds of the invention which carry a mutation in the homozygous state, is significantly higher than seed lots which may comprise unprimed seeds which do not carry the said mutation. This illustrates that the capability of a seed of the invention to germinate at a high temperature results directly from the said mutation.

TABLE 2

GT50 Dark of mutant seed lots and wild type seed lots.

| Seed name or number | Origin | GT50 Dark (° C.) | Relative increase in GT50 Dark between mutant seed lots and wild type seed lots (° C.) |
|---|---|---|---|
| Sensaï | — | 28.1 | — |
| Burovia | — | 17.8 | — |
| Ls_mt_sen | S | 39.2 | 11.1 |
| Ls_mt_bur | B | 38.7 | 20.9 |

S = Sensaï;
B = Burovia RZ

Example 4

Identification of the NXS Gene in High Temperature Germination

M2 lettuce plants which yielded M3 seed lots capable of germinating at a high temperature as shown in Examples 3A and 3B, were sequenced. PCR amplification and sequencing primers were designed based on the lettuce (*Lactuca sativa*) NXS DNA sequence according to SEQ ID No. 1.

DNA sequencing revealed the presence of a $G_{3018}$>$A_{3018}$ mutation ($T_{3017}G_{3018}G_{3019}$>$T_{3017}A_{3018}G_{3019}$) in the NXS gene according to SEQ ID No. 1 of Ls_mt_sen, leading to the conversion of a Tryptophan to a premature stop codon at position 140 in the encoded protein according to SEQ ID No. 2. This mutation led to the expression of a truncated, non-functional version of the NXS protein in the M2 plant and corresponding seeds of the M3 seed lot.

In Ls_mt_bur, DNA sequencing revealed the presence of a $C_{3518}$>$T_{3518}$ mutation ($C_{3518}C_{3519}A_{3520}$>$T_{3518}C_{3519}A_{3520}$) in the NXS gene according to SEQ ID No. 1, leading to the conversion of a Proline to a Serine at position 212 in the encoded protein according to SEQ ID No. 2. This mutation led to the expression of a non-functional version of the NXS protein in the M2 plant and corresponding seeds of the M3 seed lot.

Example 5

Identification of NXS Orthologues

The DNA and protein sequence of the lettuce NXS gene are shown in FIGS. 1A-C, SEQ ID No. 1 and 2. Orthologues of the NXS gene were identified using a Basic Local Alignment Search Tool (BLAST) to compare the lettuce NXS DNA and protein sequences with the sequences of other plant species. Using this method, 1-2 best hits per species were identified as candidate NXS orthologous genes. Primers were then designed to amplify the complete NXS gene. For some plant species, orthologous NXS protein sequence were identified by Blast X or Blast P as reciprocal best hits to the lettuce NXS or other plant NXS protein sequences. DNA and protein sequences of the NXS orthologues that were identified through this method are represented in FIGS. 2A-2GG, FIGS. 3A-F and Table 1. Multiple sequence alignments of the predicted protein sequences confirmed that these were orthologous NXS genes (FIGS. 4A-C).

The alignment of the NXS protein of more than 200 unrelated species showed that there are a number of very highly conserved amino acids amongst the NXS orthologues (results not shown). For example, the proline residue at position 212 in the lettuce NXS protein according to SEQ ID No. 2 and encoded by $C_{3518}$ $C_{3519}$ $A_{3520}$ in the lettuce NXS DNA sequence according to SEQ ID No. 1, is part of a highly conserved motif in a number of unrelated species. A non-functional version of the NXS protein, as a result of the substitution of the proline residue with a serine residue at this position was found in lettuce mutant Ls_mt_bur (See Example 4). Since the proline at this position is a highly conserved amino acid and/or part of a highly conserved protein motif, its disruption in any of the NXS orthologues would also lead to the production of a non-functional NXS protein.

The same alignment of the NXS protein of more than 200 unrelated species also showed that another very highly conserved amino acid residue amongst the NXS orthologues is a tryptophan residue, which in lettuce is located at position 175 in the lettuce NXS protein according to SEQ ID No. 2 and encoded by $T_{3196}$ $G_{3197}$ $G_{3198}$ in the lettuce NXS DNA sequence according to SEQ ID No. 1. Likewise because the tryptophan is also a highly conserved amino acid and/or part of a highly conserved protein motif, its disruption in any of the NXS orthologues would lead to the production of a non-functional NXS protein.

Example 6

Modifying Orthologous NXS Genes to Produce a High Temperature Germination Trait

Seeds of the plant species of interest are mutagenized in order to introduce point mutations into the genome. Mutagenesis is achieved using chemical means, such as EMS treatment (see Example 1), or specific targeted means. The skilled person is familiar with both chemical and targeted means for introducing mutations into a genome.

Mutagenized seed is then germinated, the resultant plants are selfed or crossed to produce M2 seed. A tilling screen for NXS gene modifications which are responsible for the absence or reduction of NXS gene expression or activity is performed. NXS gene modifications are identified based on the NXS DNA sequences listed in Table 1 for the given plant species. The skilled person is also familiar with tilling (McCallum et. al. (2000) Nature Biotechnology, 18: 455-457) and techniques for identifying nucleotide changes such as DNA sequencing amongst others.

Plants with a modified NXS gene are homozygous or made homozygous by selfing, crossing or doubled haploid techniques which are familiar to the skilled person. Seed lots from plants selected on the basis of modifications to the NXS gene are then tested for their ability to germinate at a high temperature. To confirm the high temperature germination trait resulting from modifications of the NXS gene, germination tests in the dark are performed (see Example 3). Seeds belonging to a seed lot having a modified NXS gene and a GT50 Dark which is significantly above the GT50 Dark of the wild type seed lot are identified as plants of the invention.

Example 7

Transferring the Trait of the Invention to Other Plants

A lettuce plant of the invention, grown from seeds of the Burovia NXS mutant Ls_mt_bur which is homozygous for the modification in its NXS gene, was crossed with a wild type lettuce plant, which did not show the trait of the invention.

The GT50 Dark of the resulting F1 seeds were determined as described in Examples 3A and 3B. The F1 seeds had the same GT50 Dark as the seeds of the wild type plant (e.g. the seeds are not capable of germinating at a high temperature).

From the F1 population which was grown from the F1 seeds, a lettuce plant was selected which was selfed to obtain a population of F2 plants. The F2 plants were again selfed to produce F3 seed lots. These F3 seed lots were then germinated in the dark at 35° C. In approximately one quarter of the F3 seed lots, of the seeds tested no seeds germinated. In approximately another quarter of the F3 seed lots, nearly 100% of the seeds tested germinated, which indicated that the mutated NXS allele was present in the corresponding F2 mother plant in a homozygous state. In approximately half of the F3 seed lots, approximately 25% of the seeds that were tested germinated, indicating that the mutated NXS allele was present in the corresponding F2 mother plant in a heterozygous state. The segregation of the F3 seed lots corresponded to a monogenic recessive inheritance of the trait of the invention. The segregation of the F3 seed lots was confirmed by sequencing the NXS gene in the corresponding F2 mother plants.

An F3 plant was then grown from an F3 seed lot which had the modified NXS gene homozygously present in the corresponding F2 mother plant. This F3 plant was used for further crossing to transfer the trait of the invention to other lettuce plants.

In the same manner as described above for lettuce, the trait of the invention can be transferred from a plant of any one of the species listed in Table 1 which carries a modified orthologous NXS gene, into a corresponding wild type plant that does not exhibit the trait of the invention. Depending on the plant species, F2 plants and later generations need to be selfed or crossed in order to produce seed. The skilled person is familiar with the selfing and crossing steps necessary for a given plant species. Furthermore, the segregation ratio of the trait of the invention for a given plant species is also dependent on the number of orthologous copies of the NXS gene present that is present in the genome of the species. Regardless, the segregation of the trait of the invention should still correspond to a monogenic recessive inheritance.

The invention is further described by the following numbered paragraphs:

1. A seed comprising in its genome a modified NXS gene and/or modified regulatory sequences thereof.

2. The seed of paragraph 1, wherein the modified NXS gene and/or modified regulatory sequences thereof provides the seed with the capability to germinate at a high temperature as compared to a wild type seed not having the modified NXS gene.

3. The seed of paragraph 1 or 2, wherein the expression of the NXS gene is substantially reduced or prevented.

4. The seed of any one of the paragraphs 1 to 3, wherein the seed has a reduced level, reduced activity or complete absence of NXS protein, as compared to a wild type seed not having the modified NXS gene.

5. The seed of any one of the paragraphs 1 to 4, wherein the modified NXS gene comprises a premature stop codon and/or encodes an NXS protein that comprises one or more amino acid substitutions.

6. The seed of paragraph 5, wherein a conserved residue of the encoded NXS protein is substituted.

7. The seed of paragraph 6, wherein the conserved residue is in particular a proline residue which is substituted with a serine residue.

8. A plant comprising in its genome a modified NXS gene and/or modified regulatory sequences thereof, wherein the modified NXS gene is as defined in any one of the paragraphs 2 to 7.

9. The plant of paragraph 8, grown from seed as defined in any one of the paragraphs 1 to 7.

10. Progeny of a plant of paragraph 8 or 9, comprising in its genome a modified NXS gene as defined in any one of the paragraphs 2 to 7.

11. Propagation material derived from a plant or propagation material capable of growing into a plant of paragraph 8 or 9, comprising a modified NXS gene as defined in any one of the paragraphs 2 to 7.

12. Propagation material of paragraph 11, wherein the propagation material is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

13. Tissue culture of propagation material of paragraph 11 or 12.

14. The seed of any one of the paragraphs 1 to 7 or the plant of paragraph 8 or 9, wherein the seed or plant is selected from any of the species *Lactuca sativa, Cichorium endivia, Cichorium intybus, Solanum melongena, Solanum lycopersicum, Capsicum annuum, Capsicum baccatum, Brassica oleracea, Apium graveolens, Spinacia oleracea, Valerianella locusta, Daucus carota, Glycine max, Rhaphanus sativus, Chenopodium quinoa, Vigna radiata, Medicago sativa, Cicer arietinum, Fagopyrum esculentum, Trigonella foenum-graecum, Allium cepa, Lens esculenta, Oryza sativa, Zea mays, Phaseolus vulgaris, Pisum sativum, Vitis vinifera, Triticum aestivum*, and/or *Hordeum vulgare*.

15. A lettuce seed (*Lactuca sativa*) comprising in its genome a modified NXS gene, the wild type of which is identified in SEQ ID No. 1, encoding the protein of SEQ ID No.2.

16. The lettuce seed of paragraph 15, wherein the modified NXS gene provides the seed with the capability to germinate at a high temperature as compared to a wild type seed not having the modified NXS gene.

17. The lettuce seed of paragraphs 15 or 16, wherein the expression of the modified gene is substantially reduced or prevented, as compared to wild type lettuce seed not having the modified NXS gene.

18. The lettuce seed of any one of the paragraphs 15 to 17, wherein the modified NXS gene comprises a premature stop codon.

19. The lettuce seed of paragraph 18, wherein the modified gene comprises a premature stop codon which is located within exon 3, exon 4 or exon 5 of SEQ ID No. 1.

20. The lettuce seed of paragraph 18 or 19, wherein the premature stop codon is in particular the result of a G>A SNP at position 3018 of SEQ ID No. 1.

21. The lettuce seed of any one of the paragraphs 15 to 17, wherein the modified NXS gene encodes an NXS protein that comprises one or more amino acid substitutions.

22. The lettuce seed of paragraph 21, wherein a conserved residue of the encoded NXS protein of SEQ ID No. 2 is substituted.

23. The lettuce seed of paragraph 22, wherein the conserved residue is a proline residue which is substituted with a serine residue, in particular proline at position 212 in the encoded protein of SEQ ID No. 2 is substituted with serine as a result of a C>T SNP at position 3518 of SEQ ID No. 1.

24. The lettuce seed of paragraph 22, wherein the conserved residue is a tryptophan residue which is substituted with any other amino acid resulting in a non-conservative amino acid change, in particular tryptophan at position 175 of the encoded NXS protein of SEQ ID No. 2.

25. A seed lot of the species *Lactuca sativa* wherein the seeds belonging to the seed lot comprise a modified NXS gene as defined in any one of the paragraphs 15 to 24, which when homozygously present in a seed, provides the seeds in an unprimed state with the capability to germinate at a high temperature, and which seed lot is characterized in that the GT50 Dark of said seed lot is at least 10° C. higher than the GT50 Dark of a seed lot of seeds not comprising the modified NXS gene.

26. The seed lot of paragraph 25, wherein the GT50 Dark of the seed lot of seeds comprising a modified NXS gene is between 10° C. and 25° C., between 11° C. and 25° C., between 12° C. and 25° C., between 13° C. and 25° C., between 14° C. and 25° C., between 15° C. and 25° C., between 16° C. and 25° C., between 17° C. and 25° C., between 18° C. and 25° C., between 19° C. and 25° C., between 20° C. and 25° C., between 21° C. and 25° C., between 22° C. and 25° C., between 23° C. and 25° C. and between 24° C. and 25° C. higher than the GT50 Dark of a seed lot of seeds which do not comprise the modified NXS gene.

27. The seed lot of paragraph 25 or 26, wherein the GT50 Dark of the seed comprising a modified NXS gene, is at least 31.8° C.

28. The seed lot of any one of the paragraphs 25 to 27, wherein the GT50 Dark of the seed lot of seeds comprising a modified NXS gene lies between 28° C. and 40° C., between 31.8° C. and 40° C., between 32° C. and 40° C., between 33° C. and 40° C., between 34° C. and 40° C., between 35° C. and 40° C., between 36° C. and 40° C., between 37° C. and 40° C., between 38° C. and 40° C., between 39° C. and 40° C.

29. The lettuce seed of any one of the paragraphs 15 to 24, belonging to a seed lot of any one of the paragraphs 25 to 28.

30. A lettuce plant comprising in its genome a modified NXS gene as defined in any one of the paragraphs 15 to 24.

31. The lettuce plant of paragraph 30, grown from seed of any one of the paragraphs 15 to 24 and 29.

32. Progeny of a lettuce plant of paragraphs 30 or 31, comprising in its genome a modified NXS gene as defined in any one of the paragraphs 15 to 24.

33. Propagation material derived from a plant or propagation material capable of growing into a plant of paragraph 30 or 31, comprising a modified NXS gene as defined in any one of the paragraphs 15 to 24.

34. Propagation material of paragraph 33, wherein the propagation material is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

35. Tissue culture of propagation material of paragraph 33 or 34.

36. Marker for identifying a lettuce plant or seed comprising the modified NXS gene as defined in any one of the paragraphs 15 to 24 or a part thereof that comprises the modification.

37. Marker of paragraph 36, wherein the modification is a SNP, in particular a SNP at position 3018 or position 3518 of SEQ ID No. 1.

38. Use of the lettuce plant of paragraph 30 or 31, or progeny of paragraph 32, for producing lettuce seeds which have the capability to germinate at a high temperature as compared to wild type lettuce seeds not having the modified NXS gene.

39. A modified *Lactuca sativa* NXS gene the wild type of which is identified in SEQ ID No. 1, encoding the protein of SEQ ID No. 2, and wherein the modified gene is as defined in any one of the paragraphs 15 to 24.

40. Use of the modified *Lactuca sativa* NXS gene of paragraph 39, for producing lettuce seeds which have the capability to germinate at a high temperature as compared to wild type lettuce seeds not having the modified NXS gene.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A lettuce seed (*Lactuca sativa*) comprising in its genome a modified neoxanthin synthase (NXS) gene, the wild type of which is identified in SEQ ID NO: 1, encoding the protein of SEQ ID NO: 2 wherein the modified NXS gene encodes an NXS protein, and wherein a proline residue is substituted with a serine residue at position 212 in the encoded protein of SEQ ID No. 2 as a result of a C>T SNP at position 3518 of SEQ ID NO: 1.

2. The lettuce seed as claimed in claim 1, wherein the seed germinates at a high temperature as compared with a wild type seed not having the modified NXS gene.

3. The lettuce seed as claimed in claim 2, wherein said high temperature comprises at least 29° C. to 40° C.

4. The lettuce seed of claim 2, wherein the high temperature comprises at least 31.8° C. to 40° C.

5. A seed lot comprising a plurality of the lettuce seed of claim 1.

6. A plant grown from the seed of claim 2, wherein the plant comprises the modified NXS gene and seed of the plant has the modified NXS gene homozygously and germinates at the high temperature.

7. A lettuce plant that is progeny of the plant of claim 6, wherein the progeny plant comprises the modified NXS gene and seed of the progeny plant has the modified NXS gene homozygously and germinates at the high temperature.

8. A propagation material from the plant of claim 6, wherein the propagation material comprises the modified NXS gene and is capable of growing into the plant.

9. The propagation material of claim 8, wherein the propagation material comprises a microspore, pollen, ovary, ovule, embryo, embryo sac, egg cell, cutting, root, root tip, hypocotyl, cotyledon, stem, leaf, flower, anther, seed, meristematic cell, protoplast or cell.

10. A tissue culture of the propagation material of claim 8.

11. A method for growing a lettuce plant, comprising germinating the seed of claim 1 at a temperature between 29° C. and 40° C.

12. The method of claim 11, wherein the temperature is between 31.8° C. to 40° C.

13. A method for producing lettuce seed having the capability to germinate at a high temperature comprising 29° C. to 40° C., comprising growing a lettuce plant from the seed of claim 1, selfing the lettuce plant or crossing the lettuce plant with another lettuce plant that is homozygous as to the modified NXS gene, and isolating seed from the selfing or crossing.

* * * * *

SEQUENCE LISTING

```
<160> NUMBER OF SEQ ID NOS: 70

<210> SEQ ID NO 1
<211> LENGTH: 3900
<212> TYPE: DNA
<213> ORGANISM: Lactuca sativa

<400> SEQUENCE: 1

tcgattttga gactgatttt caatgtttaa gaaagtcact atattaccat aaaatttcga      60

ttttgacatg agttttttt tctcaattat atgattaaat tttcaattct gttgccatgt     120

caaccaacag agcgattcag gagatgttat tatggtttag aagctcgatt tgtacaacaa     180

ataaataaag gtcaatataa ttgttcaaac tcacttgtaa gtcagtgaaa agggcatagt     240

caccatttta ggagatgtta ttgcagttta gaagctcgtt gtttacaaca aataaatgac     300

aagacaatat tgtgatgtgg aagctatgcc cgatcttatg tggtaggatt gagtttcaaa     360

tatagggttt gcatcgaacc caatttcaca tatcttttta ggtcgaccta gtgggtcaaa     420

ctcacttaaa gttcagcaaa aatggtgtaa tcgcccattt aggtgacact ttttattata     480

atgtttaatg tttaattctt gtcagagtat ttcttcacaa atgacgtctg aaggtcaatc     540

tagtggttca aactaactta aaagtcggtg aaaagggtgt actcaccctt tcaggagata     600

ttattgtggt ttagaagctc gatttgtaca acaagtaaat taagacccct acaaggtcga     660

tcaagaagat gtttagtgag tttgaaccac taaatcgacc ttgtaggatt ctttatttat     720

ttattgtaca aatcgagctt ctaaaccata ataacatctt ttggaagggt gtctatgcat     780

tttttgctaa cttgtaagtg agtttgaatc attggaccga cctttattta attgttgtac     840

aaatcgagct tctaaaccac aacatctttt gaattggtca attggttgat attgcaaaaa     900

aattgtaaat gtagtgatat aattgaaaag aactcggtgt caaaatcaaa attttgtggt     960

aatataatga ctttcttgca atttgaaact cagtgtcaag atcaaaattt tggtaaactt    1020

agtgacttta ttgcaattcg ggaaaaatgg ttaccgggag aacatagaga agtggtcatt    1080

tggttgatat tgcaacaaaa ttataaatat attgacataa ttaaaaaaaa aaatttatgt    1140

caaaatcaaa attttatggt aatatagtga gtacttgtca tttgtccttt atgaaatcaa    1200

cccttgaggc tttaaatgag gttaccatat gaaattgagg atgcaacaaa ccttgaggac    1260

taaaatcgta atttacaaaa ctaaatatca ggcttgaagt gaggttacca tatgaaattg    1320

aggatgcaac aaaccttgag gactaaaatc gtaatttaca aaactaagta catgcgataa    1380

caaattttgt ttggaaaatg acatggatat cggatagtgt tggattgcac ctttgaaatt    1440

tgaatcttta tgtttttaag tagttatata tttggtaaca tatacaaata cacataacat    1500

aataaaatta agatgtaatt ttgtttctct tttttaaaat attcatacac aaaatcaatt    1560

ctatatcctc tcttcattaa aataaaagga aaactaaatt aaattgggtg agatgaatat    1620

tcactcaaca gacaaaactt ttcatttctt ttctgaaacg aaaggaaaac aagactaccc    1680

atctcttttg tatctatgat tgtactacca cttctaattt ctttttata taacgacaac     1740
```

-continued

```
ttcatgaaga atcctaaccc atttcatctc tcaatctcac ttactttctt acatctataa   1800
tggctatctc ttcttgcctt tgtcaccatc aattagcact caaggtattg ttgctttccc   1860
attctactgt atctacgtgt atctgcatat gttcaaacga attctccttc aacattcatg   1920
gtttatttgc catttttgcg atctgggttc gagttatttc acgttcttgg tgctgaattt   1980
ggttggtttt gccaatttgt gtatttgcaa atgttgtaat cacttcacct ttgcatattc   2040
atgatttgtt ttccaattta ccaactgggt atgattcatt ttgctttctt cgtatcaatt   2100
tagttatttg tgcccatttc actctgttta tattgtgtgt ttgcagattg aatcatcact   2160
ttgcatatat atgttatgat gttcatatac ttatataact tgtttgtttg tacttttccc   2220
ccaattgaat tggtttactt tcccgttttc atgtttgaac tcgattggca atttagggtt   2280
catagatgtt atctctttgt tgtagattaa cctcttaacg actgcatcca aacactcgaa   2340
atccacattc gctattaaac ccatcaacac cgaattttac ggaatacata tcggaaacaa   2400
gctaagaaat caatggagtt ttatgagagg atcaggagct ataatcatac caaacgaaag   2460
cttcaatctg cgtcaaaaaa actcaaaatt gcaagcatca tgtaatcctt tcgtaccctt   2520
tgtttatcat gagataattt atcgattaaa catctaaaac tttgttaatc ttatcaattt   2580
atagttcgat tggatctttg ttcatgtagg ttttgctagt atgcaattag cgagtgatgc   2640
ttttacatta ggaactgctg ctgttcttcc attctacact cttatgatcg cagctccaaa   2700
atccgaattg gtaaatttta caatgttata aagcaaacaa aaaaaagaaa aaaaaaaagg   2760
tatcgaaata actatttaat gctttttctt tttcttttga ctttataaaa acaagaatta   2820
atcttataaa ctatatatag atatttcttt ttgacataat acataaagaa ctaaacttta   2880
aacttacact catgggactc tgtctagctg atgtgagaca ctgaattgtt ttaacttgca   2940
gactaaaaag tgtatgagaa gtagcatacc atacgtagtg cttggggttt tatactcgta   3000
tcttctatat ctttcgtgga ccccggatac atttcggtta atgttcgcaa gcaaatattg   3060
gctgcccgag gtaagaattt ctgcccgaat gatttgataa atgataatag cgtattttta   3120
aactttacca tggtttattt tcagcttccg ggtgtagcta agatgttttc taatgagatg   3180
acattagcct cggcgtggat ccatttgtta gccgttgacc tctacgcagc aaggtatgag   3240
ggtatttacg tcttttgcac agacaagata tcagtagcca atcattgtcc cacctttatg   3300
ggtgggatga aaatttgtaa attatgtacc attgtgtata agtctggtgc atgtcaaaca   3360
caatctgatg cataccaaac acagtacatg aaacgacagt cgtactgatt gaagttaact   3420
tatggttttg attggtggta acagacaggt gtatcaggat ggattggaga atgagattga   3480
gacgcggcat tcggtttctc tttgtttgtt gttttgtcca attgggatac ttgttcatgc   3540
tatcaccaag gctttaatta gtacatttag agaatcaaaa agtgagattc attgatgttt   3600
ttatttttcc tatcaagtga tggagcattt atttgttcaa gtcttttaat ctaattggtt   3660
atggttttgg tgtaaatctt tacaatttta atcatgaata tgttgtagga tttgtcttag   3720
gggtttatga tagcattgac ataattaact cttcaacatt acacggaatc aaataaatct   3780
ctaattccat aaaacacctt gtaatcctcc cttatcccaa cataatctac aattccactt   3840
gtgccaataa ggacctttta gtcatttcac tattataagc tttttatcca cgacaagatc   3900
```

<210> SEQ ID NO 2
<211> LENGTH: 236
<212> TYPE: PRT
<213> ORGANISM: Lactuca sativa

<400> SEQUENCE: 2

```
Met Ala Ile Ser Ser Cys Leu Cys His His Gln Leu Ala Leu Lys Ile
1               5                   10                  15

Asn Leu Leu Thr Thr Ala Ser Lys His Ser Lys Ser Thr Phe Ala Ile
            20                  25                  30

Lys Pro Ile Asn Thr Glu Phe Tyr Gly Ile His Ile Gly Asn Lys Leu
        35                  40                  45

Arg Asn Gln Trp Ser Phe Met Arg Gly Ser Gly Ala Ile Ile Ile Pro
    50                  55                  60

Asn Glu Ser Phe Asn Leu Arg Gln Lys Asn Ser Lys Leu Gln Ala Ser
65                  70                  75                  80

Cys Phe Ala Ser Met Gln Leu Ala Ser Asp Ala Phe Thr Leu Gly Thr
                85                  90                  95

Ala Ala Val Leu Pro Phe Tyr Thr Leu Met Ile Ala Ala Pro Lys Ser
            100                 105                 110

Glu Leu Thr Lys Lys Cys Met Arg Ser Ser Ile Pro Tyr Val Val Leu
        115                 120                 125

Gly Val Leu Tyr Ser Tyr Leu Leu Tyr Leu Ser Trp Thr Pro Asp Thr
    130                 135                 140

Phe Arg Leu Met Phe Ala Ser Lys Tyr Trp Leu Pro Glu Leu Pro Gly
145                 150                 155                 160

Val Ala Lys Met Phe Ser Asn Glu Met Thr Leu Ala Ser Ala Trp Ile
                165                 170                 175

His Leu Leu Ala Val Asp Leu Tyr Ala Ala Arg Gln Val Tyr Gln Asp
            180                 185                 190

Gly Leu Glu Asn Glu Ile Glu Thr Arg His Ser Val Ser Leu Cys Leu
        195                 200                 205

Leu Phe Cys Pro Ile Gly Ile Leu Val His Ala Ile Thr Lys Ala Leu
    210                 215                 220

Ile Ser Thr Phe Arg Glu Ser Lys Ser Glu Ile His
225                 230                 235
```

<210> SEQ ID NO 3
<211> LENGTH: 2000
<212> TYPE: DNA
<213> ORGANISM: Daucus carota

<400> SEQUENCE: 3

```
ttggaatggg tgcattagtt tatcagttcg tattgtagat ttatgttttt ataagggtga      60

aattttctgg aattcataat taacaggttg aaattctgcc acctaaatgt gtgttggact     120

gatcatttca ggaactgaaa atgtgattgt tgaatccttc ttattcttga tcgattttct     180

ttatagccat cacagttaag tttgcaaaat aatgaacaag tttgttcttg agaatcaaaa     240

tgccctcctg gtttcaatcc taaagttggg gcagtacttg ccgagttgga catgggaatt     300

attaaagtat ctatctttat actgtctccc aaatgcttat gatgaaaatc ttgaaactga     360

atgcttagta aattttcgta ttatatggtg ctggtacttg gttgcttctc attaactgtt     420

acttccattc tcgccttgta gaccgaacat tcaagcttga ctaggaaggg cttctataat     480

atcagcaaga ttcagctaaa cccagttgct attgaaggca caaacagtga cctttatggc     540

caacatgtgg tgctttggac aaagatgaga aaagaatgga gttttaagag aggatcaata     600

tctattgctg gtccgactat ggaaagattt gtgcttcaca gaaaaagctc tggagtgcag     660

gcttcatgtg agccccccttt ctttaaatct accaaacatt tttacttgtg tctaattttg     720
```

-continued

```
tgtagttatc acaaattctt agaaatatgt atcagttact ttacctttat tgatgaaagc    780

acctgtgatt ttgaacaaat gaaatgcaat gaaatcttga tggtcaatga tgcaaaacta    840

tgcaacaaaa tataatcgtg tataataaaa ccaaagcttt gatctgatgt acttttggca    900

taaggaatga tctagttgtt tgataggggt aattaaattg attgacatat atgcattttt    960

attctaagca actggttgag ggtggttgtc tggaacccag cagaggctaa ttatgccata   1020

gttcttgcat atacctgacc ttgatgtgta tgacttaatg gcagtctttt cactgtggcc   1080

ttgcagggtt tacaaattct caaattgcaa gtagtgtttt tacgttggca accgccgctg   1140

ttcttccatt ttacaccctc atggttctgg ctccaaaagc tactctggta ataatttatt   1200

gagacatggt gactgctttg actgatttta tgttcacaac ttcacatatg taatcagaca   1260

tgaaaataat agaaacttga gccatgtgac taattatttg ttttatctac caaattcaga   1320

ctaagaagtg tattcaaagt gcagttccat atgttggtct tggactttta tatgcatacc   1380

tactctacct ctcttggaca cctgatacat ttcggttgat gtttgcaagt caatactggc   1440

tgcctgaggt acgtctcaga ctagcacaaa caaaagctta agctttttac tcgttaaaat   1500

tattaaacat tttgggaaat ttttttgag gtaaaagtga tgattttggt ccatctttgg    1560

ctcaatattt ttattgtgca gttatctggt atagctaaga tgttttccag tgagttgaca   1620

ttagcttcgg catggattca tttgttggct gtggatctct ttgcagcaag gttcgtaagt   1680

gtttgaatgt gcatatacgt cagggtgcct gcagtccatt aaaattaaat tctcacagtt   1740

aaaccatttt ctaattatgc aggcaaatat ttcaagatgg actgcagaat tctgttgaaa   1800

caaggcattc tgtttccttc tgtctactct tttgcccgat aggaatctta tcgcatgaaa   1860

ttaccaaagc tctaaccaca ggtggaagaa ctgccaaacg cgagatccat taatgcaaaa   1920

atgatcagct gacagagtat ccattttcct atgacaaaga tagtagaggc ttttcttgct   1980

attagtgatt tgttttcgag                                               2000
```

<210> SEQ ID NO 4
<211> LENGTH: 2163
<212> TYPE: DNA
<213> ORGANISM: Daucus carota

<400> SEQUENCE: 4

```
atggcttccc tgtcttgcct ctgcagttct cctctgtttc ttaaggtacg tgttctgtgt     60

ttgctgttca tatagtctca attctaatca tgcttggaaa ctcgttatgt gtttgctgtt    120

catatagttt ctgtttgtat tcgttagatt gttagaagat ataatataat cctgataagc    180

actcctttca acatctcgag gttttgggag aactgatcac ttgacataag tgtttgcatg    240

atttattccc agggagggcg gcaaaaccct gatttaaagg gaaaactaac ccagcagtac    300

tacagatcat agttataaat aggtatcatt cagtagaaga aaattatgca attcagttaa    360

gcaattggat catgaataaa aaaggacggt gatgagttca cttttcattg tagtttaggt    420

tttggccttt atatatgttg ttgtcatagt tcttggtatt gaactccagg tttcagaaaa    480

gaatttcaaa ttctataaga atcttaaact gaattagttg tacgagttat gtgagaagtt    540

caagtttgaa tccagtagaa gttcaagttt gaatccagta gagtttattc gctttgttaa    600

ttggacatgt ttttactaaa ggtagtcggc cttttgatca atgatctatc tccgtttata    660

gtagaaaata taacagactt gatgtgaaat ttagctaata gtttaacctt gctgtgattt    720

ctataatagt gaatagtctt cactcttcag atatcttgtt ggtgataacc ttgtttctgc    780

tttaacattg tagaacgacg aatcaagact ggctaacaaa tcgttattag cctataccag    840
```

-continued

```
aaaggaccgg ataacaactt attgtcttaa tagtgtcgaa actgaccctt ttagtcgaca    900
tccacatagc ataaagacaa agagatggag tttcaaagga ggatcgaggg tgatcactgg    960
acccaatatt caaagatttg cttgttacag aaaaagctgt ggagtttatg ctttatgtaa   1020
attccttttt cacaaataac tttgattgag aattttaatt tactatgcat accctaagct   1080
gttatccttg gtatcttcta tatcgagaat tcttcttatc ctttaataaa aaaaattgcc   1140
atgcgctcaa tattgaactg ctttttgtga ccttgcaggg ttgacaaatc ctcaaattgc   1200
aagtagtgct ttcaccctgg gaactgcagc tgttctcccc tactacaccc ttatggttgt   1260
agctccaaaa tctgagctgg taagcctaat atggtgacag cttttactga attgcaaata   1320
ctacgatcca ttctgaatcc aaaatgtttt attttctaat agttgagcta aattactgat   1380
atgcctgatg tttacatgct tcgatattca gaccaaaaaa tctattgaaa gtggcatacc   1440
atatgttgcg cttggtcttt tgtatggtta cctactctac ctctcatgga cacctgatac   1500
aatgaagatg atgtttgcaa gtgaatattg gctccccgag gtgtgtttga actgtgggaa   1560
gaacacgcgg tttttctaat tgcagaaata ctttgtttaa aaaaaattta attaacatat   1620
ttacattctg acagttatct ggcatagcaa agatgttctc cagtgagatg acactagctt   1680
ctgcatggat tcatttgtta gctgtagatc tctttgctgc aaggtccgtt tctctccctc   1740
atttcccgcg agccttaact cttataccat gttaagtgac caattctccc aaaatttcaa   1800
gatgttgggg gaggggctta cgaggatcat attttattct aacagttcta acatttgacg   1860
tattgtgatc ctattaatca ggcaggttta tcaagatgga ctggagaaca agatcgagac   1920
tcggcattca atttccctct gcttactttt ctgtcctata ggaattatat ctcatgtagt   1980
caccaaagca ctaaccaaaa gtacagagta atccagtaag tagcaagatt cacttgtgcc   2040
taaagcatgc ttttcatttg actacagaag tacaatgttt gttactgcag attccctggt   2100
tttgcatttc acaattttag tcggcttttc catgatatat tgctcacaat tgctaacttc   2160
tga                                                                  2163
```

<210> SEQ ID NO 5
<211> LENGTH: 2028
<212> TYPE: DNA
<213> ORGANISM: Cichorium endivia

<400> SEQUENCE: 5

```
atggctttct cttcttgtct ttgccaccat caattggcac tcaaggtatt ggttaatttc     60
ccctttttact ctctctatgt gtgtttgcat atgctcaaac gacttcactt tcacgaattc    120
atggtttatt tggcattttt cgatttgggt acgagtcatt tcgcgttatt ggtactaaat    180
ctggttgatt ttgccgattt aactaccggt gtcatccaat ttgtgcattt tcacatgttt    240
ttagctacct cacttttaca tattcctgtt tgtttgcgaa tttactatct gggtgtgatt    300
cagtttgctg tgttcgtgtt aatttggttg ttttggctca tttgattctg tttattacat    360
ccatttctgt attgtgtgac tgcagattga atcattcact ttagatatac atattatgct    420
gtctgtaaat ctattcgttt gtatcttctc cccaattgaa ttggttcact cttccgattt    480
tgagttcggt tagcagttta gggttcatag atgtttatgt tcaaattaga accatcaaaa    540
ggcttacatg agtgagaaat cttgaagatg ttatatcttt gttgcagatc aacctcttaa    600
cgagtccatc gaaacccaca ttcgttctta aagccatgaa caccgaattt tacggaatac    660
atatcggaag caagatagaa aatcaatgga gttttatgaa aggatcacga gccataatca    720
```

```
gaccgaaccc tggaagcttc aatctgcatc aaaaaagctc aaaattgcaa gcatcatgta    780
atcctttcgt atccttcgtt tatcatgaga taatttagcg attaaacatc caaaactttg    840
ttaatcttat cgtgttttag ttcgattgga tcttttttca tgtagggttt gcgagtatgc    900
atttagcgag cgatgctttt acattaggaa ccgctgctgt tcttccattc tacaccctta    960
tggtcgctgc tccaaaatcc gaattggtaa ggtttacaat gttgtcataa agcaaagaaa   1020
attaaaaaaa aaaaaaaaaa atcattcaaa tacctatcta tatatcaata taattggaat   1080
ttaagtgatg tttctttttt actcatttaa agtgttgaat ggataaattg gttttttttt   1140
tctttttggg gtaaagtgtc gaatggtcta atattaattg tttaatatta attgtttaat   1200
atattaagtc cattaagtga aaaagaaaac agacgctaag tgtttacaaa tttggtcgac   1260
attaatgcag acgaaaaagt gtatgagaag tagcataccg tatgtggtac tcggggtttt   1320
atactcgtat cttctttacc tctcgtggac gcccgacaca atccgattaa tgtttgcaag   1380
caaatactgg ctgcccgaag tatgatttta cacccctata gtttgctaga tagccaactt   1440
ttaaccctag tgatggtttt atttgcagct tcccggtgtt gctaagatgt tttctaatga   1500
gatgacatta gcctccgctt ggatccattt gttagcggtc gacctctatg ctgcaaggta   1560
ggaggacatt tacgtctttt gcacaaacaa caaatcggaa gctagtccat gtcccacctt   1620
cttcggtggg atgaaaaatt gcaatttttc tcccattgac ttctgtgtac ctgtacctgt   1680
acctgtacct gatgaattgt ggttttgatt ggtggaaaca gacaggtgta tcatgatgga   1740
ttggagaagg agatcgagac acggcattcg gtttctcttt gtttgttgtt ttgtccgatt   1800
gggatacttg ttcatgctat caccaaggct ttgataagta catatagaga atcaaaaaca   1860
gagattcatt gatgggtttt tttgtgccat taagtcttaa agcatttatg ttatctttta   1920
atctaatcga ttatggtttt ggcagaaatg tttacaaggg ttggttatgt agacgctgtc   1980
atagggtttt attatagcat tggcataatt aatgttatgc gactataa                2028
```

<210> SEQ ID NO 6
<211> LENGTH: 1507
<212> TYPE: DNA
<213> ORGANISM: Solanum melongena

<400> SEQUENCE: 6

```
gatgaactgc tgggcaccag cctcggtgtc attgagtacc cgcagaaacc acactgcctt     60
tcttgctctt agagaaatta taagtcaacg tattggtgga tttggaacca agcttagcag    120
tggagggagt tctctgggag gatcaagagt cattattcaa ctaaatcttc aaagaactct    180
ttcgcaaaga aaaagctcta gggtgcatgc ttgctgtaat tactttctta caaactccat    240
tctttgtgat aaaatatctc tggttttgaa tgtttatgac aaagtaatct taaatgtgtg    300
cttaattaag ttctcgctgt acttaagatt tatcgtctca tccattcccc cttttttttg    360
gttgttgttg tttatttgga gagaaattgt ttaaaaagct actactattt tgcctttagt    420
tttaatgaat tataaattac tcaagtctaa atggtgcttt gtgcatagtt aagagtaaaa    480
cttgctatag gtgctttaag agtaatcttc ttcatgcagc tgttaatgtt ccttgaccct    540
tctgtacagt ttagcctctg gttttggcag acttttatgc caacgactaa cactggttca    600
gtttttagct aagtttctat attcttttgc agggttgcca agttcagaaa ttgcatctac    660
tgctttcaca gtgggaacag cagcagttct tccgttttat accgtcatgg ttgtggctcc    720
taaagctgaa ctggtaagat ttctatagta ctttcagtct gaactcctta agcgattcct    780
tttctagtgt actagagatc aaacttggca ctcaaattat gaattcaaaa gaccttaaac    840
```

-continued

```
acttatcagc ttcagacaaa gtagaacagt tgggcacaac ttcagtcctt ttatgtatat    900

ggaagtcact gctttattta aaagagaaat tgtaattgaa cataatttcg aatgcagacc    960

agaaaagcaa tgaaaagcag cataccctac attgtgcttg gacttctata tgcatatcta   1020

ttatacctct cctggacacc agatacaatt cggctgatgt ttgctagcaa atattggctt   1080

cctgaggtct gtgctcgact acataataat ttgtacaaat tgcatggtcg ggatcttaac   1140

acttcctttc attcagctgt ctggtatagc taagatgttt tccaacgagg tgacgttagc   1200

ttctgcatgg attcatctgt tagccataga tctttttgct gcaaggtcaa tctttaggcg   1260

tctttatctt tgttgggcta tgcccctttg ctttcttttt gggacaacat gaggaggatg   1320

ccactgttag acatctaact agagtatctc acttgaaaca ggcaggttta tcatgacgga   1380

ttgcagaatg atattgaaac ccgccactct gtgactctgt gtttgctgtt ttgccctgtt   1440

ggaattctta ctcactgcat caccaaagct ctaactagca gcccagaaaa gaaacagcat   1500

aggactc                                                             1507
```

```
<210> SEQ ID NO 7
<211> LENGTH: 2919
<212> TYPE: DNA
<213> ORGANISM: Solanum melongena

<400> SEQUENCE: 7

tctacttgct tttgtcactc tcaattctca ctcaaggtgt gccttttctg cttctcctct     60

attcatagct tgtaatatat gttcttcttc atttgtctag gtaattaaat tggtgtttat    120

tgttctcaat ttttttaatt gaatacccat acctggtctg tatgttcaac tgacacacaa    180

ctgtttgttt agatctgaag ttgctccatt gctatatgat aatgaaaaat tcaatttgag    240

agcacctaaa atgctagtga aggcttcagg tagatactgc aatagtggag ctagcatttt    300

caccaagggt gttcatactt ttagaacata tgggtgggtg ggtgattttt gtatcaaggt    360

atatatataa aaatatttat attttgaaaa agttttccaa cgaaagatgg ttcacccttg    420

ggtgaatgta gttcgccccc tggtagatag tgagcaacat ctatgattta aagatgtttt    480

tggcaataga gggtggggat ggtggtttta gtgaattgaa tgtcaatctg gcaccattga    540

attatcactt gttcgttgaa ttatgctatg agaaataagg cttagtgaat ggcatttcat    600

gctcaacaca tattcgataa aattaattta tacttggtag ttgaaacaaa aaagaaagaa    660

agaaatgagg tttttctacg cactaaaaat gaccaagttt gaaaatacaa tgaaatgtca    720

ttcctgctga acgactatgc tacttacctt agatggaaag ctggacacct gctctgtcat    780

caaatatccg atgttatatc aggaggaacc agtttccatc ctccatgctt aaaacaataa    840

attctgacct ttcaagtcaa caagttcagg aacgaggaac caagcatagc aatgggtcca    900

gtttcctcgg aggatcaaga gtaatgcgtc agcctaacct ccaaaatctt ccacaaagaa    960

gaagctgcag ggtgtctgct atgtgtaatc ttttcttcgc tgcttcctta gtctttatca   1020

tttattttta gctctcattc tgtgtcttgc tactttcttt ttggataatt cttgggaatc   1080

agctatacac agtcaggaat ctggttatcc atcttaattt acagtcatca cataatgttg   1140

cgaattaggt tattatgaca cctccctgcc aactgctaac acatctgtta gtttaccaca   1200

cttgataaaa aaaatttatt acaatgcttg ttaactttgt acaaatactc tatatggcct   1260

tttcttaaca cgtttggctt aatatccaca cctactttcc tccttttaga tgaaccaggg   1320

aaaacaaatt cgaaaaagaa aagaagttgt agaagtacaa caatttgctg tcttccttca   1380
```

-continued tctggttgaa actttgatat ctcccaccct gagtcacatg ttccattgga atcttgtttc 1440
cctcattacg ttgctggatt ttccatctca tgtcaataaa gactatgctt acttgctcat 1500
gtagatgtgt aaattgctag tctcccagat cttatcaagt gacagttttg atgtattgta 1560
tatggaatat caaactaaat atcaaattga tctactccat ttgattataa atccatacgt 1620
atatgtataa atacttattt atgaagcttc ttattgttta ctctctttgc aaatgttgca 1680
agtatcacct atttgaactt ttgggacaac tgatgtctta tttttacagg gttgcctagt 1740
tctcaagtag ctagtagtgt ctttactcta ggaacagcag ccgttcttcc gttttacacc 1800
ctcatggttg cagcacctaa agctgaactt gtaagttatc tcagttctgt aaagctacat 1860
tctatttttg aaaatttttct agagtaaacc ctctgggtgt attttcaact taagaagctc 1920
ttgtttattt ttttaaaatt ggaagacata aaaagtgtta cttgcaaagt tctctctccc 1980
cgtgtcatgc acaaaagtag aactcggggc atgatttcag ttgtattgat ttgttatcta 2040
attgcaagat acttaatttc gtgcctttcc gagatatact gtaatagggc ataattaaat 2100
acttaatgca gaccagaaaa ttgatgggaa gtgccatacc atatgttgcg ctcggacttc 2160
tgtacacata tctgttgtac ctgtcttgga caccagatac aatccggcta atgtttgcta 2220
gtaaatactg gcttccagag gtttgttctt gtgcttagca aatgatggtt gtcatcttgt 2280
gctgattcta taattagggt tgttgacgtt tcattctgtt cagctctcca gtatagcgaa 2340
gatgttctcc agtgagatga cactagcatc agcttggatt cacctattgg ctgtagatct 2400
ttttgctgca aggtctctct ttctctcgca cacacacttt attgtatgtg ttagattgtt 2460
ccatgctagt tgaggaaatg ggtagttgtc tccttgttag gtgttgccat gttggacaat 2520
ccgcatttta tgagctagtg tttcgggtgg tatcagactc atcacactct tggtttactc 2580
aatgtttcca cgcgccagat gtccggtcaa gggcatacag ggagggtgga ggaaggatgt 2640
ttggttgtcc gactgttctc gcatgtttgt gtagccagtt gtttgcttgc taatcctatt 2700
gggttgagga aaatggagga aggtgctttg ttaaactatt ctaatgctgt tttttatttg 2760
aaacaggcag gtttatcatg atggtttgca aaatggtatt gaaacgcgcc attctgtgtc 2820
tctctgcttg ctttttttgcc ccattggaat tgttattcat ctcctcacca aagctgtact 2880
aagtaatgcg gaaaacatag tgcctagaac tcactgaca 2919

<210> SEQ ID NO 8
<211> LENGTH: 3000
<212> TYPE: DNA
<213> ORGANISM: Solanum lycopersicum

<400> SEQUENCE: 8
caaaaaggtg taaagtagca ccaaggagta agtgcttaaa caactttccg tccaaataga 60
ggtgtgtggt cggatttggc aaattctcaa ctaacatcac aaaatgcaat atattattaa 120
cattattagt cacttcatga tttctttatt tgcaccaaac tttgagttgc ttctaaagct 180
aaaaataaat tatacttttt gttgcttctg tttttctcat tattgttgca acttcaacaa 240
caataaagca tgtacttctc ttcttcttcc catgtttcac tcaaggtatg ctctttcttt 300
ctttctgctt ctatgtcttg ctctctgttt ctgttttagc tctgatatgt tttttgcctc 360
tcaaaagggc ctccacagtc atccactgtt tcttgctggg tattgatatt tagttgagtt 420
gtttgatcag tttataagct tgatatttag ttgagttgtt tgatcagttt ataagcttga 480
acgaacgccc tcgtgatgct ttaggaagat attgttagcc cacaagttag ggcttattcc 540
cactgaaaaa tagtcggtac atattttgat tgaatcgatg agaaaaagaa aaaagtaata 600

-continued

```
atcttttagt atagaaaaat taggaagttt cccactatta tgattcgtag tgggaaacgc    660
ttgtgtttct agtaatgacg tgggaatagc ctcttttcga aatacaagaa gtgtgtacag    720
tgtatatatg cccactcttt ccctctgctg gcactagcag aagtcctttt tgcacagggt    780
aagctcttag gttcacatta ttgagttaca ggcaaccaga aatggaaatt tacgctaact    840
tcttcgttgg aagagatgtt ggcgaaggcc acaaagctag aagggcattt tgtcatctta    900
accaacgtgc acgtgcaatg atgtgaaatc caatatcttc gtctacaatt acttgtcgta    960
acacgtttct gctctaagac tttctctcaa catatctgta agcagggagt ccgcattcac   1020
tattaagcct acatagatgt ggagattatt gaagattgag gcactagcta aatgaaggtg   1080
ttttagatca atgtgaggtc tagcacacct ttcggaatag gactacaaat aaataaggtt   1140
ttgcaatgca ttgaacctga acaagttgga ggctacaacg aaatttaact gcttttcacg   1200
cagtcatttt tgtttatcag tctataattt catttcctga aacgaaccat tacttgttgc   1260
agatgaactg ctgggcaccg gccttggcgt caaaagtccc tctgaatacc aggagaaacc   1320
agactgcctc tcctgctctt agacaaatga agtctgacct tttaagtcaa cgtattggtg   1380
gatttggaac caatcttagc agtggaggga gttctctggg aggatcaaga atcattactc   1440
aactaaatct tcaaagaact ctttcgcgaa gaaaaagtcc tatggtgtct gcttgctgta   1500
aattactttc ttacaaaccc cattctttgt aataaattat ctattgtttt aaatgttcat   1560
gagaaagtag ttttagatgt gtgtttgatt gagttattgc tgcagttggg aagtattgtc   1620
tcattcattg cccttttttt gtttatctgg agaataagat tgtttttaaa gctaatcttc   1680
tgtacagttt agcttctggt tttggcagac ttttatgcca actactgaca ttggtcaagc   1740
ttttagttga gtttctatgt tcttttgtag ggtgccaag ttcagaagtt gcatctactg    1800
ctttcacagt gggaacagca gcagttcttc cgttttatac cgtcatggtt gtggctccta   1860
aagctgaact tgtaaggttt tttaagtact gtcaatctga acttcttaag gatttctttt   1920
ccagtgtact gaagattaaa cttccactca tattatgaat tcaaaagatt tttctaaatt   1980
aaacacttac cagcttcaga caaagtagaa cggttagggc acaacttcag tccttgtctt   2040
gtgtatatga aagtcattgt tttatttcaa tgagaagttg taactgaaca taatttcaaa   2100
tgcagaccag aaaagcgatg aaaagcagca taccctacat tgtgcttgga cttctgtacg   2160
catatctatt atacctctcc tggacaccag atacaattcg gctgatgttt gctagtaaat   2220
actggctccc ggaggtctgt gctcaaccac ataataattt gtcaaaactg cattatcggg   2280
atcttaacac ttcctttcat tcagctgtct ggtatagcga agatgttctc caatgaagtg   2340
acgttagctt ctgcatggat tcatctgttg gccattgatc tttttgctgc aaggtcaatc   2400
tctaggcatc ttatctttgt tggcctatgc cccttcgttt ttttcttttg tataacatga   2460
ggaggatgcc atagttagac atctcacttg gagtatttca cttgaaacag gcaggtttat   2520
catgatggat tgcagaatga tatcgaaacc cgccattctg tgtctctgtg cttgctgttt   2580
tgccctgttg gaattcttac tcactgcatc accaaagctc taactagtag cccagaaaag   2640
aaacagcata ggactcatta accaatgttt taggccttct tatgttatcc gtaaatgatc   2700
agccagcgcg tgaacttatg agcaaagtgt aaaggtttta agtcaatgaa tacataagct   2760
atttcaataa cttgtttcta agatggatga atgtacaaga tttcttcctt tagttccact   2820
ccaaacttct gatttactgc atccttaact aagcgtatga gctcaagcat gtcttgagaa   2880
gttgcagaac cacaatttat gaaaaagttg gcatgcttgt ttgagaccat ggctccacca   2940
```

actctcaacc ctttcaaccc acttttctct atcaattctg cagcagaaac acccatagaa 3000

<210> SEQ ID NO 9
<211> LENGTH: 3400
<212> TYPE: DNA
<213> ORGANISM: Solanum lycopersicum

<400> SEQUENCE: 9
taaacgtgag ggaccatttt tgtcatttaa tttggtaaaa ttttagttgt atttgaagtc 60
ggtctgtttc actcttatat gagaagagaa ttcatcaaga gggccagggc tcatgattta 120
tcattctgtt ggtgaaacct ctcattactg tacttgcaat gtttaatttt attttccaga 180
tgccattttt gctataattc ttattgttgt tgctcgcaat tctcacaccc atcaaccatg 240
gccttatctt ctacttgctt ttctcactct caattctcac tcaaggtatg ccctttctct 300
gctactctct attcatagct tgtaatataa gtttttcttc attaaattgc tgtttattgt 360
ttgttctcag ttttttttaat tcataccccg tatgtatgtt aaactgatac acacattatt 420
tgctacttgt actgtgtggt tagatctgaa gtttctccgt tgctatatga atacattgaa 480
attgaaaatg aaaatttgag agcaattaag atgctagtaa agtcttcatg tagatagtgc 540
tgagcaacta tctatcattt gaagatattt tggcaatagg gagtgtttgg aagaaaaaac 600
tttgaagaat gaggtgctag tgtttggagg tttagtgaat tgaatgtcaa tcaggtaccg 660
ttgaagtctc aatgtcattt gaattatgct attagaaatt aggcttggta tattgcatgc 720
caagcaaatc ttcaataaaa tttatctata cttggtaacg gaaaaaagaa aatgaggttt 780
tccaactcac taagcactaa cgagtttgaa gctacaatga aattccaaac ctgctaaact 840
attgttttat tagaagtaat caatctctac tacttactgt agatggactg ctggacgcct 900
gctctgtcat caaatatcct atgttatatc aggaggaagc agcctccatc ctccacactt 960
aaaacaataa actcaaacct tttaagtcaa caagttcata aacgaagaac caagcatggc 1020
aatggatgga gtttcctcgg aggatcaaga gtaaagtgtc agcctaacct ccaaaatctt 1080
ccacaaagaa gaagctacag ggtgtctgct atgtgtaatc ttttcttcca ctgcttatct 1140
ttatttctca actcgtgtca tgctacttcc tttttggttc ttttggataa ttcttgggaa 1200
tcagctatgt tcggtcagga atgtggttat ttacagtcat ctcataatga ttcgctttag 1260
gttattatga cacctacctg ccaaaacata tgttaatcaa caaactgaat tcaaaaaatc 1320
tgttacaatg catattaact ttgtacaaat acttttatgt gcccacttgg cttaatgtcc 1380
aaacctgtta tcctcctatt agatgaacca ggaaaaacaa attcaaaaag aaaagtactt 1440
ttagaagtat aacaatttgc tgtcttcttt caatctggtt gataatagaa atatctccca 1500
ccttgtccaa tgttccgttg aaatctcgtt tctctcattt cgttgctgga ttttctatct 1560
catgtcaatg aaagaatatt cttacttgct aatgtacatg tgtaaactgc tagtgtctta 1620
cattataccg aaagacagtt ttgatgtatt gtatatggaa tatcaaactg aatatcgaat 1680
tgatctattt gattataaat atatatgtat ataaatattt atacatgttt tttaagcttc 1740
ttattgtgta ctctctttgc aaatgtttta gtgtcatcta tttgaacttt tgggacaact 1800
gatgtcttat ttttacaggg ttgcctagtt ctcaagtagc tagtagtgtc tttacgctag 1860
gaacagcagg cgttcttcca ttttacaccg tcatgattgc agcacctaaa gcagaacttg 1920
taagtaatct cagttctgta aagcaacact gttttttttta ttttctagag agtatgccct 1980
atggatatat tatcaactta ggaagctctt gtttatttct tttcttggaa gacataaaga 2040
aaagttacac atgccaagtt ctctctcctt atgtcatcca caaaagtaga agtcatgggg 2100
cataatttca gttgcattga tttgtgatct aattgcaaga tactgatttt gtgcctttcc 2160
aagatatatt gtaatatagg gcataattaa atacttaatg cagaccagaa aattgatgga 2220
tagtgcaata ccatatattg tgctcggact tctgtacgca tatctgttgt acttgtcttg 2280
gacaccagat acaattcggc tgatgtttgc tagtaaatac tggcttccag aggtttgttc 2340
ttgtacttaa caaatgatag ttgtcatctt gtgctgatac cgtgatttag gctgttgaca 2400
tttcattctg ttcagctgtc tggtatagca aagatgttct ccagtgagat gacattagca 2460
tctgcttgga ttcacctatt ggctgtagat ctttttgctg caaggtctct ctctttctat 2520
ctcaaaacca cacttcatta ttgtaaatgt gttggattgt ccgtgttagt tgaggaaatg 2580
gccatttgtc tctttataag gtgttgacat gttgcacaat cctcatctta tgagctagtg 2640
tttggagttg tgttggagcc aggcggtaat atttggttgt cctacactag ttgaggaatg 2700
gactgttctt gcctcatata atcttggcca tttctcaatt tatgagctag cttttaagat 2760
tgtttcagat tcaaggccat ttcgttaaca gtatgtttgt gcagccagtt gttcttttct 2820
gatcctattg ggtcgaggaa aaaggaggaa ggtgccttgt taaactattc taatgctgtt 2880
ttttatttga aacaggcaag tttatcatga tggcttgcaa aatggtatag aaacgcgcca 2940
ttcagtgtct ctctgcttgc tattttgccc cattgggatt gttattcatc tcctcaccaa 3000
agctgtacta ctaagtagtg cagaaaaaac agtgtttaga actaactgac agagattcaa 3060
caattgtttc ctgttaacga ctaatgtaat tgtgaacaaa agggtaatct tcattcaact 3120
acgtaaagtg tgcaaatttg tatatcattg atccaacact gcttgaagca ttcgaattga 3180
tgagctctcc ttatattttt cagtaaatct aaattctttt tagatggccg aatgtcagtt 3240
ttctttcttg gatcgttact cctgccaaat aaagaaaacg tttcttcttc tccaatccaa 3300
ttactgatag gatgcaaata agaatttctc ctctcatatt tgccataaac attgcctata 3360
attgacttct aagtgacata aagttgaaat ttgttctaat 3400

<210> SEQ ID NO 10
<211> LENGTH: 2375
<212> TYPE: DNA
<213> ORGANISM: Capsicum annuum

<400> SEQUENCE: 10
gataccctct tgatagttta ggttgatatt gttaacccat aggttaaggg tacggacgtg 60
taaataacct ctttgcaaaa tacagggggg agtggggcat atattgcccc ctcttccttc 120
tgccggcaca agaagagata gtttgtgcac agggtaagtt cttagaggtt gatcttattg 180
agcaacagac aaccagaaac tggagcttac gtgaacttct tcaaggaaga gatgttgcag 240
acaaagggca caaagcgagg tatctattcc ttgaggaaga agggcatttt atcatctaga 300
cagacgtgac acgcataatg gtgtgaaatc taacaccttc atcttcgatc tctcgtagca 360
acacattttc agagctaaga atttctctcg acatcattct ttttatttaa gtcattaata 420
ttacaatctg gaagcaggga gtccgcattg actattaggc ctacatagat gtaaagatat 480
ttgaagattg aggcatgcta gtgtctgaag gcctagcaaa ttgaaggtcc attagatcaa 540
tgtgaggtct agcacacctt ccggaatagg actataaaga aataaggttt tgcaacacat 600
tgaaccctaa acttggaggg tacactgaaa ttcaactgct tttctggcgg tcatatttgt 660
tttacccatc tagaatttca tcatctgaaa ttaaccatta cttattgcag atgaactgct 720
ggacaccagc tttcgtgtca aaagtcccgc tgaatacctg gagaaaccag actgcctccc 780

-continued ttgctcttag agaaatgaag tctgaccttt taagtcaaca tattggtgga tttgaaacca 840
agcatagcag tggagggagt tcactggcag gatccagagt cactattcaa ctaaatcacc 900
aaagaactct ttctcaacga aaaagcttta gggcgtctgc ttgctgtaat tactttctta 960
caatctccat ttctttgtca taatttatct ctggatttga atgttcacga taaagtagtt 1020
ttaagtatgt gctttaagtt attgctgcag ttgggtttag tagtctcatc aatcgtcttc 1080
ttttttttat ttggagaata aaattgctta aaaagcgcat attttgtcat tagttttaat 1140
gaattataaa gcactgaagt tccaatgata ctgagtgtaa aataaattag agttttaaca 1200
gtaatctccc ttcatgcagc tattaatctt ccttgatcct tttgtacagt ttttcttatt 1260
ttggcagact tttatgccaa ctactaacat tagctaagtg tatcactggc aagctcttag 1320
ttaagtttct tattcatttg cagggttgcc aagttcagaa gttgcatcta ctgctttcac 1380
agtgggaaca gcagtagttc ttccatttta taccatcatg gttgtggctc ctaaagctaa 1440
acttgtaaga tttctaaagt gcttttactc tgaactcctt aagcgatttc atttccagtg 1500
tactggagat caaacttggc agtgaattta ttaattcaga aggcgttctt aaattaaaca 1560
ctaaccagct tcaaacaaag tagaacagtt ggtacacaat ctcagtcctt atgtatatgt 1620
tttccattca gtgctttagt ttgatagtat tgaattataa catgctgatt ttggcaaaag 1680
atgtaagtca ttgctttatt tcaaagagca agttgtaact gaaaaaattt caaatgcaga 1740
ccaaaaaagc gatgaaaagt agcataccct acattgtgct tggacttttg tacgcatatc 1800
tattatacct ctcttggaca ccagatacga tccggttgat gtttgcaagt caatactggc 1860
ttccagaggt ctgtgctcaa ctacataata atttgtacaa gttgtatggt cgggatctta 1920
acacttgctt ccattcagct gcctggtata gctaagatgt tctccaacga ggtgacgtta 1980
gcttctgcat ggattcatct gttggctatc gatctttttg ctgcaaggtc aatctctagg 2040
catctatctt tgttgggcta tggccctttg atttcttttt gggacatcat gtggagggtt 2100
tcacttttag acatctaact agagtatttc acttgaaaca ggcaggttta tcacgacgga 2160
ttgcagaatg atattgaaac acgccattct gtgtcgctgt gcttgctgtt ttgccctgtt 2220
gggattctta ctcacttcat caccaaagct ctaactagta gcccagaaaa gagacagcgt 2280
aggattcatt aaccaatgtt ttaggccttc ttatgttatc tgtaaatggt cagccagcat 2340
gtgactatca gcaaagtgta aagattttca gtcaa 2375

<210> SEQ ID NO 11
<211> LENGTH: 1510
<212> TYPE: DNA
<213> ORGANISM: Brassica oleracea

<400> SEQUENCE: 11
agtttctgtc aaagagttcg tgaatcgaat cggagatggc tttttctcag cctttgtctt 60
cttcgtctct ctcggtattt cgcttttttt ttagtttact ccaaaatata tacatctgta 120
attattgtat atgttcatgt acacttgttt gatattgtcc gattagtttc tgtgtcgagc 180
tttacttact agtactcata tagcttagat tccttatcct taagaatcaa atcagccaat 240
cgatgggttc gcttgagttc acttgccctg tctctgtctg aaaatttcag attctgtgag 300
ttaaagtcgt tatcaagttt ttgttttttg ttttttaatc agattagatt catttttttg 360
gtggtacaga tgacgaatcg gagctttgta gctaagagct cggtgacagc aagtctttct 420
cttaacaagt ctttaaagat tcgattccat aatcgttgga gcttcgacgg aggatcaaga 480
atcgttctgt tccccagtgt atcatccgat tcgtcctccc ttgttcacaa gaaacgctcc 540

-continued tgcgtacgag cttcatgtaa tgtctctttt taactgaaaa cattgaagcc tcaaactttg 600
tcgagagatt ctagttagct cttgtgattt cagactaaaa acatgttgat gttcagggat 660
ggctacgtct caaatcgcaa gcagtgtatt tgctgtcgga acaaccgcgg ttcttccttt 720
ttacactctg atggttgtag ctcctaaagc tgaaattgtg agtccttttc tttgttgcag 780
tcttacaact tcttttgcag aactaaagag gttcatctga aattgacttt ttttttcaag 840
aaagaaattg aatatatgtg tttctttcag atttacaaaa aaaagtgtct ctcttttgtg 900
cagaccaaga agtgtatgga gagtagcata ccgtatgtcg tcttaggcgt attatacgcg 960
tatttgttgt acctttcttg gacacctgaa acgctcaaat acatgttttc cagtaaatac 1020
ttgttgccag aggtttgttt tcaatacata ctgtataaca atgtttcata gtagctacta 1080
aatgttttcc tctctctctt ttctttggtc atttgcagtt gtccggaata gcgaaaatgt 1140
tctcaagtga aatgactctt gcttctgctt ggattcatct tcttgttatt gatctttttg 1200
ctgccaggta tgttacaatt ttcaggtttt ggtttcaatc aaaagtctaa aacatgtttc 1260
ttataacaca tgttttgttt gtttctatgc agacaagttt ttaatgatgg cttggagaat 1320
aagatcgaga cgaggcactc ggtttcactt tgccttctct tctgtccggt tggaatcgtt 1380
tctcatgtgg taaccaaagc tttaaccaac agttctacat ccaacaccaa caaccagtgc 1440
aagtaaactg atcattgtgg ctggtctctc atcactgtct ttcttaactg cttataaaga 1500
tttttgattg 1510

<210> SEQ ID NO 12
<211> LENGTH: 2169
<212> TYPE: DNA
<213> ORGANISM: Apium graveolens

<400> SEQUENCE: 12
aactcatatc tttgtccctg tctacataca tatgatatat agatatgttt atgaccaagt 60
tgtctttatg actttttttgc aatgacctca ggatttcttt aattatgtct actaccagac 120
atatatgcat atgaatgtca agagtgaatt gaagaattgt tggtggattt gggtatttgt 180
tatgatatgt ctcttttgtt tttgactgat ctgcggtgat tctgcaattc ttcttctcag 240
tttgtattgt caattggtgt tctttttaag gtggaatttg aataaccagt aggttgaaaa 300
ttctaccaat acattatgtg ctggactgat catttcattc aggacttgcg gatgcaattg 360
ttgaatcctt gttatttcta atcaattttt ctccatagcc ctcatgccta agtgaaaaaa 420
aaaactcaat ttgttatgtg aaattcaaaa tgtccctttt gtttcaatcc tgaagtggga 480
atgcagttgc caagctgcgc atgattgaat ctttttagaa tccccatatg ctgatataga 540
aactgaatga ttagttgatt aataatattt tcttattatt tggtattgtg atcgttcgtt 600
ggttctttat ttataacttg aacttgaaca tgaactatta cttaacttca tttctttcct 660
tgtagaccga acattcaaca ttgagtacga agcccttatg taacatcggc cagagtcggc 720
tgaacactgt tgctattgaa ggtataaaca gcgaccttta tggacaacat ctggttcttt 780
ggacaaagat gagaaaagaa tggagtttca agggaggatc aacatctatt gctgttccta 840
ctattcaaag atctgttctt tacagaaaaa gccttgaagt gcaggcttca tgtaagcccc 900
ctatatttga ttcctctaag cacctcaatt tgtttctaaa gctgagtagt taccgcaagt 960
tcttagagtt aatatcatta attttgttct atgcgacaat tagtcgtcag catctatgat 1020
cccttacaaa taaatttatc tagatggcca atgatataaa tctatgtaac agtgtgaaat 1080

-continued gatgaactgg aaacaaagct ttgatctgat gtaattttgg cgcaaggaat gatcttagtt 1140
gtttgataaa ggcagttaat gtgaccgaca tgtagatatt tttattctaa gcaactggtg 1200
gaagttagtt aggaacctag taagggctaa ttgtgctaaa ttacttgctg ttgcttaact 1260
tgatgtgtac aaattgttgc taaaattgaa atttgcaagt ctgtagcatt ttgactggct 1320
gtcttctcac tgtgaccttg cagggtttac gaattctcat attgcaagta gtgtttttac 1380
attggcaact gcagctgttc ttccatttta caccctcatg gttctggctc caaaagctaa 1440
cctggtaaaa atatttgttg gaacatggtg actgctttga ctggatctaa tgttctactt 1500
catatacata accagatttc aacctcttaa ataattacgc cgagtgacta atagttttct 1560
ttttatacta aatttagact aaaaagtgta ttcaaagtac acttccatat gttgttcttg 1620
gaattctgta tgcatatcta ctctacctct cttggacacc tgatacattt cggttgatgt 1680
ttgcaagtca atattggttg cctgaggtgc gtttcacaca atcaaaaaac aaaagcttag 1740
gctttcaaca cctagttttt attctgaaac aatttggaag ttgtttttga gatgaaactt 1800
atgattgtgg tccatctttt gctcaacctt taaactgtgc agttatcggg tatagctaag 1860
atgttctcca gtgagctgac attagcttcg gcgtggatcc atttgttggc tgttgatctc 1920
tttgcagcaa ggtctgtaag tgtgtgcata tgtgtgattc tttttgcagt gtattaatat 1980
aaatttctca cagtagccgt tctgttctgc aggcaaatat ttatagacgg actgcagaac 2040
tacgttgaaa caaggcattc cgtttccttc tgtctactgt tttgtcctat aggaatttta 2100
tctcatgaaa ttaccaaagc tctaaccaca ggtggaagaa atactaaacg ccagattcgt 2160
tgatgcaaa 2169

<210> SEQ ID NO 13
<211> LENGTH: 2025
<212> TYPE: DNA
<213> ORGANISM: Apium graveolens

<400> SEQUENCE: 13
ggtaagtgtc ctgtgktcat atagtttcta ttctaattgc gttttagttt gtagctattt 60
ttctttcttc gtttgtctac ttgattaaat cttgtgaagg tgaattcaag tcatatttaa 120
aaaaattgaa tactaagtag aattattaag tactttagta tttacctttc tatctatgtt 180
catattgctc tcttggatcc tagttggata ttatgtttct atttgtgttc atcaagaaag 240
tgtttgcatg atatatattt ttgtacaggg tggcaaaaac ccaaactttt atgcgaaaat 300
ttcgaaaaac tgtatacaga tcatcacagt cagcagtact acaaatcagt agtttcaaag 360
ttacaaatta actggaggaa taatacaagt catttaaaca gttggatcat caataatagt 420
ggagtgtgat gattttaatc tttttattac agttctggtt ttagcctatt gatgatatgt 480
tggtgtcagt ttgtcgattg aagttttaag ggtcaagtct actggaattt gtatgatatc 540
gactactttg taaattgaaa ctctggggtt caaaaaagaa ttttgaaatt tgaactctaa 600
aatgatttta atctgaatca gtttacccca gttgatttgc tttattggac atatatattt 660
actcaaggtg tttggacttt gatctatcca atcctatata gtacaaaaat atgctgaatt 720
ttacctttaa agcgattgct taaatagcga tccttatgta tccctcagat ttttttgtct 780
atagttaagt tcttgtttca caggtgaccc tggaataagg atgctaataa ccttcatgtt 840
tctgctttaa aactgtagaa tgacgaccta agactgacta acagattatt agaagcctgt 900
tttagaaagg accagttaac aacatgtgct cttaaaagtt tcaaaactga cccttttagt 960
cgacatccac caagcataaa gacgaagagt agaactgaat ggagtttcaa aggcggatca 1020
agggcaatcc ccggaccaac cattcacaaa tttgctcgta atagaaaaag ctgtggagtg 1080
tatgcttcat gtaagttcat tttccagaaa taatttgata gtaaatttta atttgctatg 1140
catatcctaa gttgttatac ttggtatctt ttctctttga atttgttctt atcctttcat 1200
atacaattgt caagtgttca tgatctaact gctcttttat gttgcttgca gggttcacga 1260
atcctcaaat tgcaagtggt gctttcaccc tgggaactgc agctgttctt ccatactaca 1320
ctcttatggt tgtagcgcca aaatctgagc tggtatgctt ctatcaccaa atgcggtgac 1380
agcttttatt gacatgcaaa tagtaattag gcccaatctg aaactaaagt tttttatttt 1440
ctgaaaattg agaaaaacga ctgatatgca tgtttacttg ctccaacaat cagaccaaga 1500
agtctatcga aagtggcata ccgtatgtta cgcttggtct tttgtatggt tacctacttt 1560
acctctcatg gacccctgat acaatgaggc tgatgtttgc gagccaatac tggcttcctg 1620
aggtatgttt gagtagcttg tgggaaaaaa atgtggtttt tccatttgta gaaacgcttt 1680
gttgttaaat gaatttaatg aaccaaatta tgttgttaca gttatctgga atagctaaga 1740
tgttctcgag tgagatgaca ctagcttctg catggattca tctgttagct gtagatctgt 1800
ttgctgcaag gtttgtttct ctccctcatc catgtgtagc tttgtggtgg gagacttgcc 1860
aagttctaac gtttgacatt ttctcatcct atcaggcagg tttatcatga tggactggag 1920
aacaaggtcg agacacggca ttcaatttcc ctttgcttac tcttttgtcc tataggaatt 1980
atatctcatg tagtcaccaa agcactaacc aaaagttcaa agtaa 2025

<210> SEQ ID NO 14
<211> LENGTH: 2000
<212> TYPE: DNA
<213> ORGANISM: Spinacia oleracea

<400> SEQUENCE: 14
gaatggggca tgaaaacgaa gtgatgacaa aaagagacag tggcgcactg tcatccctcc 60
catcttttct tccttcaatg gggaacaaag ttatcttcct tctttagtag tgatgatgat 120
gtcaaatcaa tttacatcta aacctaatca tcaacataaa ttcagtaatt aagcattgtt 180
cattcattat actttctggg tcttttggaa tttctgggtg ttttttgagc tcttctggta 240
tggctttatc ttcatgcttt gcctatcatc cccagatctc ttccaaggta cccactcttt 300
ttttctcttc aattcttttt tccaataaca atttgtccaa attttgtgag tatcaaattg 360
tttctggttt atattgagct caaaattttg atttgattgc ctttatatta taaacgtgtg 420
catagttctg ctggatttca tctgggtatt gttcaaatta attgatttta gtatatcttt 480
gtcgttgttt tcttcattca tgtgtatttg tctgctggtt aaaaaaaaca gaacaaacac 540
ccataagtct gtaatttacc agcttatacg aatctggaaa tgttaaaaaa tgcatgtttt 600
gatgttctgc aatctgcagt caatcaagtt catcatgatg acactggtta atggattctg 660
cgcgaatgat ttgatcttgt ccatttttat gaattaaggt tgtttgctgt agattgattg 720
cagcgttcta gtagataaaa accatcatca ggtgggttta agtccgagtt tagttctatc 780
tgttcaaggt gtgagaaatg gaatatttag ccagaaagtg cctaagctca gagcggagat 840
aatgcacggt tgttgtttcc ttggaggtct tagaattgat attagaccga cagtaaacga 900
atccaatttt tcgcgtagga attctggagt atgttattct tgtaagcctt ctcgtcttta 960
gcctgaaaat cttaggtttg aaggttcttc cttttaagtt ataacccatt acatcatact 1020
ttgtactgct tatgttattt cagggttgtc gaatactcaa gttgctagca gtgcatttac 1080

-continued attaggaaca gctgctgtcc tcccatttta cactctcatg atcgttgctc cgaaagctga 1140
acttgtaatc ttctcagaac ttactcagca ataataatga tacatcaagt ttgttgatgt 1200
aacagtcgtc gttatttctt gtatgtatga atgaatgtaa actggattac tgcagactaa 1260
aaagactatg aaaagtagca taccatatgt tgtgctaggg cttctgtacg catatctttt 1320
gtacctttct tggacgcctg aaaccatacg cttgatgttt gcgagtaaat actggttacc 1380
tgaggttagt ttgtttagca tcaactgaca tattcaatta tgaaatatga aactaatttc 1440
atattcagta atctgcattt ttatggatga tatgcagctt caaggtatag cgaaaatgtt 1500
ttccagtgag atgactttag catctgcatg gattcatctg ctggtagtgg acctctttgc 1560
tgctaggtca cttcctactc aagtcaagaa ttatggtatt ctgttagaat gagacactga 1620
attcagaaga aaaaaaaaac tcacaaaatc ctatatattt tctgaacagg aatgtttatc 1680
aagatggtct ggagaaggaa gtcgagaccc ggcattcagt ctcaatgtgc ttgctattct 1740
gtcctgtagg aattctaagt catctcatca ccacggcgct gaccagacct tctgacaaaa 1800
ctcgacatag cgatactatt atctaatttt tctgaactag agttttaatc tgttttttgt 1860
gaactgatgt tttggttgga tgtgccaagg aagttgctgt caaatttaaa tgaaacaatg 1920
catatagaca ataattagcc ataagagaca cttagagaaa aacattagca ctgaatagtt 1980
ttcttgtcat gaattgatag 2000

<210> SEQ ID NO 15
<211> LENGTH: 1934
<212> TYPE: DNA
<213> ORGANISM: Valerianella locusta

<400> SEQUENCE: 15
cttttgccac cctcaattct cactcaaggt aatcatttaa tgctttcttt acttttgttt 60
gtgtagtttt atggtttttt gatgttcttg attcataccc atttctcaat tttgcctaat 120
tgtgaaatct ttgaggagtt ttgattggat atgggtagtt ttgttgtttt cttacaaaga 180
aaatgtgaat ttttggcact ttattgttct gggtttgtgc tagatctgag aatacttctt 240
gttaattgtt cgaatttatg cgagaatttg agtaatttgg agctagtttg ctttcggttt 300
gactaattta gtgtttgatt tggaaaattt ggacatttta agctttaaag gtaactttct 360
aaaccagttt atagagtcgg tcaataaatt cattatcggt gatgtgtcag catcctattg 420
gataattcac actccgtatg atcagcaaaa agtgtcactg ttgattgttt gatgcattgg 480
gtaattgtac attagatcag agtacaaccc tttattgcat acaattagtt tcagcttttg 540
acattgaact tgtatataga agagagtttt actgtcatca atctagttag ctgtatataa 600
tccctaacat tttagagctt aatttgtaga tggattgctc aatatcgact gtaaaatctt 660
cgtatattac aagaaaccaa aaacaactga caaattttac tctcgggagt acgaacggtc 720 aacctttttgg tcaacatttt gcgtggaaag aagctaagct atcttgtggg tcgagtttct 780
caggaaggtc aaaagcaatc gtttcatcga accctcgaaa acttattcac ttcagaaaat 840
actgtcgaat ttacgcttca tgtatatcct ttcccacaga actttgaata tcaaactttt 900
gtatgaagtt tgttaaatcg tatcttttgc agggtggtcg aatcctacta caattgcgaa 960
caatgtattc accttgggaa ccgttgccgt tcttcccttc tacacactaa tgcttgtggc 1020
tccgaaagcc gaactggtaa aacctagtcg aattactctc aagtttagta cagtaattta 1080
ttttttcttg ctttgactaa aagattgtaa tctgaatgca gacacaaaaa tcgatggaaa 1140
gcagcatacc gtatatcgtg cttggagtat tatacgcatg cttattgtat ctgtcgtggt 1200

```
cgcctgatac attacgcctc atgtttgcga gcaaatactg gcttccagag gttcgtcatt   1260

tgaataaaat gctaatttgg tgtttatatg ttaacaaggg caaaacagtc atattttaaa   1320

gtaattagat tcagattagt tataacccgt ggtagattaa cagttctttt aaattcagat   1380

agcagacttt cgtaaagttt tgttgagatt ccaaattcca aaccatcata cactatcttg   1440

cacttaaatt gacctttcg gtgtttcagc tgcccggtat agctaagatg ttctcgaatg   1500

aaattacatt ggcttctgct tggcttcact tattagctat cgatctttac gctgccaggt   1560

cacctcctat ctctctttct acacacacat acacataata tataccgagc ctttggtatt   1620

accaacttag cgtaaaattg ggtgcaaaaa aagggtatct atatgtatat atgtgtctct   1680

aatttcttta tgatacacac acgcttcttt tttgaacctc gaaaggctta tttgaaatac   1740

gtattatgta ttcacattta aacacatttt ttgcactttt tggcacctga atatcacagc   1800

actttatatt ttctgacatt ggtaatctct gttaacaggc aggtttacaa agatggaatc   1860

gagaacaaca tcgagacgag gcattcagtt tcgatatgtc ttttattttg tccaattgga   1920

atcattgttc atta                                                      1934
```

<210> SEQ ID NO 16
<211> LENGTH: 1900
<212> TYPE: DNA
<213> ORGANISM: Raphanus sativus

<400> SEQUENCE: 16

```
ccctttttta gtcagtggaa gactctttta agatttcaag tcaaaaaaaa aaaaaaaaaa     60

agactctttt aagatttgtt ttatttaaca taaaaaatgc atttgagttc ggtgtagaag    120

ctaaatgaag agccaatttc cctcaaagag ttcgtaaagt ttgaatcgga gatggctttt    180

tctcagcctc tgtcttcttc gtctctcatg gtatttcgct tttagttaaa aaaaaaaatt    240

attctccagt atatgtacat cagtaactaa tgtatgctta tgtacagttg tttggattag    300

attctgtgtc gagcttactt actagttagt actcacatag ttcagattcc ttatccttaa    360

gagtcaaagt tcactttccc tgtctctgtc tgaaaatttc agattccgtg acttaatgtc    420

gttatcaagt tttttttttt gtttgatttt ttttaatcag attagattct tttttttgg    480

tggtacagat gatgaatcgg agctttctag ctaagagctc ggtgacagca agtctttctc    540

tcaacaagtc tagagtgtgc gttgattctt taaaaattca attccagaat cattggagct    600

tcgtcggagg atcacgactc gcttttctcc ctagtctttc gacgaattca tcctcctttg    660

ttcacaagaa acgctcctgc gtacgagctt catgtaatgt ctcttcttaa ccggaagatt    720

ttaagctttg aactttgtcg agatttaata tattatgttg atgttcaggg ttagctactt    780

ctcagatcgc aagcagtgta tttgcggtcg gaacaaccgc ggttcttcct ttttacactc    840

tgatggttgt agcacctaaa gctgaaattg tgagtccttt tctgtgttta caacttcttg    900

tacagaacta tgagaggttc atctgaaatt gaatattata tgtgtctctc tttttgtgca    960

gaccaagaag tgtatggaga gtagcatacc gtatgtcgtc ttaggcctat tatacgcgta   1020

tttgttatac ctttcttgga cacctgatac gctcaaatac atgttttcca gtaaatactt   1080

gttgccagag gtttgttttc aatacaaact ctataacaat gttttttata tagctgctaa   1140

atgttttctt ctctcttttt tttttccttg gtcatttgca gttgtccgga atagcgaaaa   1200

tgttctcaag tgaaatgact cttgcttctg cttggatcca tcttcttgtt atcgatcttt   1260

ttgctgctag gtatgttgca attttcaggt tacttttggt tttaatcaaa agttgcacat   1320
```

gtttcttata acagatgttt tgtttgtttc ttctatgaag acaagttttt aacgatggct 1380
tggagaataa gatcgagact aggcactcgg tttcactttg ccttctcttc tgtccggttg 1440
gaatcgtttc tcatgtggtt accaaagctt taaccaacag ttctacatcc aataccaata 1500
accagtgcaa gtaaactgat catcttggtt ggtctctcac cattgtcttt cttaactgct 1560
tataaatgtt tttggtttga gatagttcat tttgctttag cttcggttaa gtcagcagaa 1620
cgagtttgtt gtggatttag ttattgaaaa aaccaaataa gaccaaacaa cttgagacag 1680
tgtttctttt actatttggt agacataatt ttggattccc tgatcagtca cagagattcc 1740
ccgtgatctc tagctatttt agagagtatc caactcctgg aaactcaaaa aaacacacgg 1800
tcacctaatt tagaatactc tctaacaaca tttgcctgcg atctctagct atttatacta 1860
tagccattat aaagaactat gttttaaatt gtactagctt 1900

<210> SEQ ID NO 17
<211> LENGTH: 1712
<212> TYPE: DNA
<213> ORGANISM: Capsicum baccatum

<400> SEQUENCE: 17
atgaactgct ggacaccagc tttggtgtca aaagtcccgc tgaatacctg gagaaaccag 60
actgcctccc ttgctcttag agaaatgaag tctgaccttc taagtcaaca tattggtgga 120
tttgaaatca agcatagctg tggagggagt tcactggcag gatccagagt cactattcaa 180
ctaaatcacc aaagaactct ttctcaacga aaaagcttta gggtgtctgc ttgctgtaat 240
tactttctta aaatctccat ttctttgtca taatttatct ctggatttga atgttcacga 300
taaagtagtt ttaaatatgt gctttaagtt attgctgcag ttgggtttag tagtctcatc 360
aatcgccttc tttttttat ttggagaata aaattgctta aaaagcgcat attttgtcat 420
tagttttaat gaattataaa gcactgaagt tccaatgata ctgagtgtaa aataaattag 480
agttttaaca gcaatctccc ttcatgcagc tattaatctt ccttgatcct tttgtacagt 540
ttttcttatt ttggcagact caatcttcct tgatcctttt gtacagtttt tcttattttg 600
gcagactcaa tcttccttga tccttttgta cagtttttct tattttggca gacttttatg 660
ccaactacta acattagcta agtgtatcac tggcaagctc ttagttaagt ttcttattca 720
tttatagggt tgccaagttc agaagttgca tctactgctt tcacagtggg aacagcggta 780
gttcttccat tttataccat catggttgtg gctcctaaag ctaaacttgt aagatttcta 840
aagtgctttt actctgaact cctttagcga tttcatttcc agtgtactgg agatcaaact 900
tggcagtgaa tttattaatt cagaaggcgt tcttaaatta cacactaacc agcttcaaac 960
aaagtagaac agttggtaca caatctcagt ccttatgtat atgttttcca ttcagtgctt 1020
tagtttgata gtatttaatt ataacatgct gattttggca aaagatgtaa gtcattgctt 1080
tatttcaaag agcaagttgt aactgaacaa aatttcaaat gcagaccaga aaagcgatga 1140
aaagtagcat accctacatt gtgcttggac ttttgtacgc atatctatta tacctctctt 1200
ggacaccaga tacgatccgg ttgatgtttg caagtcaata ctggcttcca gaggtctgtg 1260
ctcaactaca taataatttg tacaagttgt atggtcggga tcttaacact tgcttccatt 1320
cagctgcctg gtatagctaa gatgttctcc aatgaggtga cgttagcttc tgcatggatt 1380
catctgttgg ctatcgatct ttttgctgca aggtcaatct ctaggcatct atctttgttg 1440
ggctatggcc ctttgatttc tttttgggac atcatgtgga gggtttcact tttagacatc 1500
taactagagt atttcacttg aaacaggcag gtttatcacg acggattgca gaatgatatt 1560
gaaacacgcc attctgtgtc gctgtgcttg ctgttttgcc ctgttgggat tcttactcac 1620
ttcatcacca aagctctaac tagtagccca gaaaagagac agcgtaggat tcattaacca 1680
atgttttagg ccagcatgtg actatcagca aa 1712

<210> SEQ ID NO 18
<211> LENGTH: 1257
<212> TYPE: DNA
<213> ORGANISM: Chenopodium quinoa

<400> SEQUENCE: 18
atggcttttt cttcctgctt tgcctttcat ccccagatct cttcttccaa gattgattgc 60
cgagttttag tacataaaat ccatcataag gcaggattaa gtccaagttt agctctttct 120
catcagggtg taagcactga aatttatagc cagcaagtgt ctaagctaag acctgatgta 180
aagcatgatt ggtgtttcct tggagggctt agaattgatg ttagaccgaa agtaaacaaa 240
tttgtgtttt cgcggaagaa ttctggagta tgctattctt gtaagatttc tcttcttaat 300
cctgaaaatg atggtttgct caaagcctgt aacatgtgat tatcagtttt tatccttttc 360
gagtttataa tctcaggttc gacctttaac ccaatgcagc atactttgct tgttatctca 420
gggttgccgg atcctcaaat tgctaccagt gcatttacca tagggacagc agctgtcctc 480
ccgttttaca ctcttatggt tgttgctccg aaagctgaac ttgtaacttc tctgaactaa 540
ctgaactatg tatgaaattt tttcttggtg taacagtcat cgttaaatag tctaaatgaa 600
tgttacacca aggaaagtgt ttattgtgtg ctcttctatt atgtgtatga cagtatgatt 660
actgaatata ctgcagacaa aaaagaccat gaaaagtagc ataccatatg ttgtgtttgg 720
ccttctgtac gcttatcttc tgtacctttc atggacacct gaaactataa gcttgatgtt 780
tgccagtaaa tactggttac ccgaggttag tttgtttggc attaacaaat taacgacaga 840
ttcaaataca aaactaattt atattcacaa ttttgcattt tatggatgat atgtagcttc 900
agggtatagc gaaaatgttt tccagtgaga tgacattagc atcagcatgg attcatctgt 960
tggtagtgga cctctatgct gctaggtctc ttcttccctc tcctctgctt actctagtag 1020
tctagattat ggtgttctat tataatcagg cgttgattaa aatctaacac actcctattt 1080
tgtgaacagg caagtttatc atgatggtct acagaacgaa atcgaaaccc ggcattcagt 1140
ctcaatgtgc ttgcttttct gtccaattgg aatcctaagc cacttgatca catcgtcact 1200
gaccaaacct gctgagaaaa ctagacatac agatactatt atctaatttt ttctgaa 1257

<210> SEQ ID NO 19
<211> LENGTH: 723
<212> TYPE: DNA
<213> ORGANISM: Fagopyrum esculentum

<400> SEQUENCE: 19
atggcgttat ctacttgctt ctcacatgcc cggatcttct tacagaatga catgggcagc 60
aaggttcaga ggactcagct taacttcagg ttggaaacaa gacacaccgt ttctcgtcaa 120
tctttgaaca ttcaacactt ttgccaaaac cccctcagtg aacagagcct tggtctaggc 180
tgcatgaccg ctgctagaac aaagattaac acgacaagtc tgtcaaaaaa aagacctgga 240
atttgttcat gctggatggt agggtctcag attgctagca acgctttcac cttaggaacg 300
gcagctgtac tccccttcta cacactcatg gtctttgctc ccaaagctga aatgactaag 360
aaagcaatgg acagcagcat accgtatgtc atgcttggac tcgtatatgc atacttacta 420

-continued

```
taccttttcgt ggacaccaga caccataaag ctaatgtttg caagtaaata ctggctaccc    480

gagttacccg gtatagcaaa aatgttctca aacgagatga cgttatcgtc tgcttggatt    540

cacctgctga tagtcgacct ctttgctgcc aggcgtatat atcatgacgg attggagaat    600

aagattgaaa ctcgtcattc agtgtctatg tgcttgctcg tctgccctat tgggatcttg    660

atgcatacaa ttaccaaagc actgaccaga acacgagttg aaagcagcaa acacaatgta    720

tga                                                                   723
```

<210> SEQ ID NO 20
<211> LENGTH: 1978
<212> TYPE: DNA
<213> ORGANISM: Lens esculenta

<400> SEQUENCE: 20

```
gctgaatctg ttattcacta tccttgtttt gcttcaacca tgtctttctc ttcttgctat     60

tcccatttac ctttagcatt taataaggta cactttttct gttttcatgt tttttcaatt    120

ctttgcacat gttgttttgt aatcttatct gcatttttct tgtctttttg gtggattttt    180

ttttgtaccc ttttatttta atttgatttt tttcaaatgg ggtttctgtt tgaggtttaa    240

agttttgaac tttggttaaa aatatctgaa attgaaagtt ttttgctttc tgtcattgat    300

ttgaatcacc aatgcattac taatcaaatg gccatttgag ttttttcttt tgttgttaat    360

ttttgtatgt aatagatctg atgatgctag gtgcatgttg gcatgttgat gataaactat    420

gtagaacaac actttaggtt gacggtgtgt ctgatattgg atgtgagtcg gcggataccg    480

atagaatact gacacacgta gttacattga atcattctat tttctcaaat tatgatggtg    540

ttgacgtgtc actatcgtat ctggtgttca tgttagtgtc ggtgcttcgt aaaaaacaaa    600

tacgggtttg ttcaaatagt ccttgaatat tgagctgtat gattcacctg cacaaactat    660

gatatttcat atctgagctc aatgtagttc atttattcta attgattgat catcactggg    720

ggcaggatat aaaactctgt aggacagttg gacaagagaa gctgaatttt cctttcacta    780

taaggagtaa tagtgttgag ctgtgcaccc gacgcatttc gagcagtaga gccggcttaa    840

gtggagattg gagtttcata ggaggatcca aaattgtagt aaaacctaaa gctacaacat    900

cgtttcgcaa tccaaaacga agtcaaatac atgcttcatg taataatctc ttttcatgct    960

acttaatggt agggataatg gtgacaatat ttgttctgca tgttcattgt tctagctcta   1020

tgtttcaggg ttcataggat ctcaacttgc tagcactgtg tttacatggg gaacaatcgc   1080

ggtgctcccg tattacacac ttatggtttt cgccccgaaa tccgagctag tacgtttgat   1140

tagtgattgc aattcacttc attaaaataa catattgata ttcttgtttt tcatttcatt   1200

tatttggtta tgattctgat atcctgattc atttttctga aatgcaaaat tacagaccaa   1260

aaaggctatg cagagtaatt taccgtatgt aatcctcggc gttctatacg cttacttact   1320

gtgcctttct tggacacctg aaacggttcg attgattttt gcaagtaaat acttactacc   1380

tgaggtgagt agtcattcat tcatcgatga agttcagttt tctttctcta atgagttctt   1440

ttatctaact cgtaactgtt tatattcgct actccatcat gcagcttagc agcataggaa   1500

aaatgttctc tagtgagttg actttagcct ctgcttggat tcaccttttg gttgttgatc   1560

tttttgctgc aaggtccggc attttatctt ccttttttgcg ataagatttg atatttggac   1620

acaaaaatca gcaacaattt ggataaacat cgttcaaata tatggttaat cgcattcagt   1680

gaatggtcaa tgaatacaac tctaaattaa tcatgtattt gagtcgcatt aactctaaat   1740

tgttgtcgaa ttttgtgtca aaataacaac tatttctcat tctttagcta tttttctaat   1800
```

agtatatttg gttcaaaatc caggcatatt ttccgcgaag gaatggagaa tcagattgaa 1860
actcggcatt cggtttcctt ttgcttgttc ttttgcccta tagggattct tactcatgtc 1920
atcactaaag caatgaccaa aactacaaga aaacagggtc atggtttata gatggcac 1978

<210> SEQ ID NO 21
<211> LENGTH: 3149
<212> TYPE: DNA
<213> ORGANISM: Medicago sativa

<400> SEQUENCE: 21
atcatgtctt tctcttcttg ctattctcat tcaccattac catttaataa ggtacamccc 60
tttcattgtt ttgttttgta atcttatctg catttttttt gtcttttttg gtaccttttt 120
ttgattttac acaaatgggg tttctgtttg aaatgtaaag ttttgaactt tgaataaatg 180
tatctgaaat tgaaaattgt tttctgtgat agatcaraat caccaatgcr ttaywaatgt 240
gaaawgggkc tttgagtttt tttttttttt ttgttatttt taagtttgta atagatttga 300
tgttaggtgc atgttggtat taaatatgta gaattgacac ttcacattga tgtcagtgtc 360
atgtttgtgt aagtgcttca taggcaataa aagggagttt atattgccgc gtaagtataa 420
ctcagatggt aaaatgttgc agtgacattt gatatgttaa aatgcatgtt ggtatattgt 480
cgcgtgagta cacctcatat gatagaatgt tgcagagaaa tttgatatgt tgtggcgtcg 540
gttcaacccc tcattttcaa cttcttagca cttggttggt gtgagttttg ccgctaggtt 600
gtttaaaaca aaacaaatag gagtttgtat ttcaaaaagt tggcactctt gtgtcatcaa 660
accaactttg gagcaccgac acttaaaatt gaagatttgt ccagtgttta gcatgtgtcg 720
atgtccaaca ccggcatatg cggttacatt gaattatttc attttttgag tcaatgtagt 780
ttatttattc gtatgtatgg ataatctagt gtgtatttct gagctcaaga agttttattc 840
tatttcatat tgatttataa tcatttgggg caggatataa aactctgtag gacagttggg 900
caactgaagc tgaattttcc tttctctatc aggagtgatg gtgttaccaa acacatttcg 960
agaagtagat tcagtttaag tggagattgg agtttcatag gagggtccag aattgttgta 1020
aaaccaaaag ctacaagatc ggttcgccat ccaaaaagaa gtcaaataca tgcttcatgt 1080
aatccttttt taatgctact ttttcatgta atctagaatt ggtgcaattt gtttcttaca 1140
tataatttac cattcaatag aattggctgt gaaggaattt ragcataatg gatatattta 1200
ggttcttttg caaaaattgt tggatctgta aggatctgat acacaagatg catctctata 1260
tttatcttat cttttttggc ggcattatca taaagtaggt tactattagg gcatgtttgg 1320
attgacttat ttgagcttat ctattgatat agagcctagt aagactgttt gagacttgag 1380
agaggttatg aaaacactta tacatgacat gtgcataagc tgtttttagt ttatttcctt 1440
aaatgcttta agatagttta ttgaaacagc ttatagatta tatgaaaaca gtccaacttt 1500
attttattgt ttgttataaa aatagcttag acagaagcac ttatatgata agcgtcagct 1560
aagctgttta tccaaacagg gtcttgtctt ttctgagctc tattcttttt aagtttttgg 1620
agacaagtta tggatgttaa cattgctcct tttgcatgta ttcccttttc tacaattatt 1680
catgtggccc ctgatctcag ctattcgagt ttcctaattt tctgttattc ttttgtatat 1740
tgtaactttc aaagccttga acaaacacat ttaggtcgac accattgaat cgaatararatt 1800 gttataatat acttgaaaaa acttgattat gatctatgct taaattgctt gttctgtata 1860
aatggyggtg attcattgtt ttacctcaat gttgcagggt tcataggatc tcaacttcct 1920
agcactgtat ttacatgggg aacaattgca gtgctcccgt tttacaccct tatggttcta 1980
gccccaaaat ccgatctggt acgtttcttt ctgcatttga gaaaaattat gattagtaat 2040
ctcattttca caattcatat tcagttttta ggtacattaa caaaaaagca ttctgatatt 2100
ccttttcatt tcatttattt ggttatgata ctgatatcct gattaatttt tctgaaatta 2160
aaaaatatag accaaaaagt ctatggaaag tagtttacca tatgtagtgc tcggcattct 2220
atatgcttat ttgctgtgcc tttcttggac acctgaaaca gttcgattga ttttcgcgag 2280
taaatactta ctacctgagg tgtgtattca ttcatcaacg aagttatgtt ttctttcttt 2340
aaagagttct attattcaaa ctcataaccg tttatatttg catactcctt gcagctttct 2400
agcataggaa aaatgttctc tagtgagttg actttagcct ctgcttggat tcaccttttg 2460
gttgttgatc tttttgctgc aaggtcctgt tgtatctttt gtgatttcta cttcacccaa 2520
ttttcctcgt tattgctggt ttttcattca tgaatgatat tttgatacaa atttgcgaac 2580
aaaaaatcga gaacaatttg gataattaat gccgttaagg tayctggttg atcgwattaa 2640
kkggttggtt aatgaatata aktatatgtc acaactcatt aatcatccgg ttaatgcaat 2700
taaccctgaa tttggacgtc ataaaccaat ggtttttaga tgttcaaata tacatggtat 2760
ccattaatca tcccaattat attcatgatc ttcaggtttt cgaatgcaca tgatattcta 2820
ttaaccataa tctgttaatc tgtgttaaac tatacacatg atatcgtggt taatatcgtg 2880
attaatgaca ttcaaaaccg tggtgaattt tgttgtcgaa tttgtgttaa aataacacag 2940
ctctttctca ttctttagtt atttctctga cagtattttt ggttcaaaat ccaggcatat 3000
atttcatgat ggactgaaga atcagattga aactcggcat tcagtttcct tttgcttgtt 3060
cttttgccca attgggattc ttactcatgt catcaccaaa gcaatgacca aaactacaag 3120
aaaagatggt catggtttat agatggcac 3149

<210> SEQ ID NO 22
<211> LENGTH: 393
<212> TYPE: DNA
<213> ORGANISM: Pisum sativum

<400> SEQUENCE: 22
atggttttcg ccccgaaatc cgaactaacc aaaaagtcta tggaaagtta tttaccgtat 60
gtaatcctcg gcgttctata cgcctacttg ttgttccttt cttggacacc tgaaacggtt 120
cgattgattt tcgcgagtaa atacttacta cctgagctta gtagcatagg gaaaatgttc 180
tctagtgagt tgactttagc ctctgcttgg attcatcttt tggttgttga tctttttgct 240
gcaaggcaca ttttccgcga tggaatggag aatcagattg aaactcgaca ttcggtttcc 300
ttttgcttgt tcttctgccc tattgggatt cttactcatg tcatcaccaa agcaatgact 360
aaaactacaa gaacagagag tcatggttta tag 393

<210> SEQ ID NO 23
<211> LENGTH: 2958
<212> TYPE: DNA
<213> ORGANISM: Vigna radiata

<400> SEQUENCE: 23
tgaatcactt attagctctt ttgcttttcc ttcaatcatg tctttctctt cttgcctttc 60
ccattcccca ttgacactca aggtacactt tctcttagct ttcctattgc tgccattgat 120
ttctaatttt acatgcaatt tttcttccac ctttttgctc attcgctacc ttttatttat 180
cacttatttt ctttcctggc ttcagctcat ttcccccatg cccactagat tggagtttga 240

-continued

```
ttccctacgt ttgaactcta aagttttaaa ctttgaatgg ttattggacc gaaagtggcc    300
attttgcgta gatttcaacc acctaagcat taccaacgaa ttgggcattt gtgaatttat    360
ttttttgctt tgcatggttg tttgcttgtt ttgctttgca tggatctatt ctaggcgctt    420
gttggtgtag tagagttaaa aaggagtttg tatttctgaa ctggcttttc cgtgtcttca    480
aaagctctaa attcattcag ttctgtgggt ttgttcaaag agtccttgcg tgttgaagtt    540
tcattcaaat aataatctgc acaacctggt tatttccact ctagaaaagg tttaatataa    600
tttattcgta tatatggata gcataaggtg tactttctgg gcttaagaca aactgtgctt    660
ataattgaga ttctgtttgt ttcattttgg cagcctataa aaccttgtgg ttctgttggg    720
atgaggcaaa attttgcttt ctctttcaga agtaattggc ctgagctttg taacagacac    780
attgtaggga gtagaaggtt gcagggaaat ttaccaaggg tcaacttaag tggagattgg    840
agtttyatag gaggatccaa aattgttatg aaaccaaatg ctacaagatt gcttcattat    900
ccaaaaaggg gtcaaatgca agcttcatgt aaccctctta tactacagct tctcattttc    960
aaactcattt tgaaaataac gtgtgtcttg tgctggacca aatttattta agaaccaatt   1020
gaagtctctg gtatttttga tgtggtgata cttttctgtg tctctgagca acttacaggt   1080
gaaattggag gttttataat taggcctctt tcctctaaat ttttctcatt ttgaccaccc   1140
tggaaaattt cactgcattc tgatttatat aaatatcatt agcgcaagct gtttcttcat   1200
tcatatattt tgattcttat taaaaaactg ttggatttgt cttgccacta aactaatttg   1260
tttatctcga aatagagcac aaattaagga tttgattcac agaatgaatt tacatggtta   1320
gcttaaatta cccctcgtgt cagtatatct ataacttaaa ttactgtatg atatacacgc   1380
acattgaaac taccgagagc tataaatatc cgtgcattgt ctgcatgact tcaccaagtg   1440
ttgttcttag ttcaagctta accaagttac tccgctttat tttttgaaat ttttagggac   1500
cagttattga ttttaagttg tccctttga tttagtcttc cccattttca tgtggctgcc   1560
gattccggct atctgtgctg ttgtggttcc tactttttca ttattctcta gcataatgtg   1620
actttgaatt tgatagcctt gaggaaagtc attttgtttg gacagaaaac tctttaatgt   1680
cgaatctgaa cagctttttc taacatggtg cttaaaattt aaatcttgct actagttctg   1740
ctcttgaagc agatgttcaa tttcttggaa aggtatgcta ggaatcaggt ttcactgaag   1800
ctattcagct gtggtctaaa tttcgtacga ccattacatt cattatggtt gggtttaaag   1860
tctgccttta cctttcgata tttttctatt ttactgttaa agcaatcgat cacaatgagt   1920
aattctaaat agcaaagatg tgcttattgt tatcttaact acttagacat tttggtaatc   1980
tgtttctctt tgtataaagt tgactgaatg ttcctttatt ctgtataact gatggtgact   2040
atatttttcg cctgatactc acttttcttc ctttcatttt caggcttcat aggatctcaa   2100
cttgctagca ctgcatttac ggctggaact gtagctgttc tcccatttta cacacttatg   2160
gttctagctc caaattctga tctagtatgt ttctaactgc agtggagaaa atttacgacc   2220
aacgagcacg attcattgca acaactttgc tttattacat gtctgtttag ttaccatgca   2280
aaaatcattc acatatataa ttattttcta tagtagtaaa taatccttgt gtggaatttg   2340
gatattcttc tttctcgtaa gcttctattg ggtctctgat tttgtacttc acgtctttcc   2400
tgattcatgt taagtgcaaa aatgcagacc aagaagtcta tggagagtag tctgccatat   2460
gtagtgcttg ggattcttta tgcatatttg ttgtaccttt cttggacacc tgagacagtt   2520
cgattgattt ttgcaagtaa atacttgcta ccagaggtgt gtgtgaatgc attcagcaat   2580
```

-continued gaagtttttc ttcccaaaag agttgtatgc aactgataaa tctgaatact tgatgcagct 2640
gcctggtata gcaagaatgt tctccagtga gttgactttg gcctctgcat ggattcacct 2700
gttggttgtt gatctttttg ctgcaaggtc gtggatttta tctttctctt ggtttctcat 2760
tctttactta tttatctaat cctatttctg gttatgaatt caggcatgtt tttcaagatg 2820
gactgaagaa tcagattgaa actcggcatt ctgtttcttt ttgcttgttc ttttgcccca 2880
ttgggattct tactcatatc atcaccaaag ccatcaccaa agctgccaca aaagagggtc 2940
atggtttata gatggcac 2958

<210> SEQ ID NO 24
<211> LENGTH: 744
<212> TYPE: DNA
<213> ORGANISM: Vigna radiata

<400> SEQUENCE: 24
atggctttct cttccttctt tttccattct ccgacactat tgaagattga tcacttgggg 60
cagactaaaa gaccttgtgg taaagttgaa aaggggcaaa agtttccttt ctctgtcagg 120
agtaatggtg ctgagactga actttgtaac cagagtcaac ttagtcagag aagtagagtc 180
agagattgga gtttcatgag aggatcaaga gttgctatga aaccaaaaat cttgagattg 240
gctccttctc gaaaagtccc tcgtctatat gcttcatggt tgtcaggatc agaacttgct 300
agcactgcct ttacattagg aacaaccgca gtgcttccat tttacacact aatggttcta 360
gctccaaatt ctcaactaac gaagaagtct atggaaagta gtgtaccata tattgggctt 420
ggagttctat atgcatattt attgcacctt tcttggaccc ctgagacagt tggacttatt 480
tttgcaagca aatatttgct accagagctg actagtatag ggaaaatgtt ctccagtgag 540
atgactttag cctcagcatg gattcacctt ttggttattg atctctatgc tgcaagacat 600
gtttttctgg atggacttga gaatcagatt gagacaagac attcagtttc tctgtgcttg 660
ttcttttgcc ctattggtgt tcttactcat gtcatcacca aagcaacgac taaaagtagc 720
agagaaaaca agagtggatt atag 744

<210> SEQ ID NO 25
<211> LENGTH: 3249
<212> TYPE: DNA
<213> ORGANISM: Trigonella foenum-graecum

<400> SEQUENCE: 25
tgtctttctc ttcwtgctat tcwcaytcrc cattgccatt taataataag gtacaacact 60
ttctctgctt tcttttcctg ttttttcaat tttctgtttt gtaatcttat ctgcattttt 120
cttgtctttt ttatggatat tttgtacttt tttttttttt taattttcca caaatggggt 180
ttctgtttga tgtgtaaagt tttgaacttt gaataaatat agctgaaatt gaagattctt 240
ttttgtcata gatttgaatc accaatgcat tactaatgaa atgggccttt gagcttttat 300
tttttagttt gtaatagatc tgatgctagg tgcatgttga tgttggtata ttggtaatga 360
actatgtaga agctacactt cagattgata atgtgtctgg tgtttgacac gtgtttgcgg 420
atacaacacg acattaacac atgtggttgc atttgatcac tttcattttc ttaaattgtt 480
acaggtgtct acgacttagt gtcgtgtcgt gtatgtgtta gtgtttcaaa aagttgacac 540
tcctgtatma acaaaccaat atgtgtaaaa aaaactatgt agcaccgaca cttcatattg 600
aagatatgta tggtgtttga gatgcatcag tgtccagcac cgacacaata ctgacacatg 660
tggttacatt taattayttc attttctcaa attatgatca atgtcaatct gtcagtgtcg 720

```
tgtctggtgt ccgtatctgg cttcattggc aacaamtatg tatttgttca tgtagtcatt    780
gcatattgag ktgtaagaat cgtcagcrcg acctgtatat ttcctgttga agatcaaaca    840
atttagttca tttactctta ygaatggata acctagggtg tatttctggg ttcaagaaat    900
tttattctat tattgattga tcatcacttg gggcaggata taaaactctg taggacagtt    960
gggcaagtga agttgaattt tcctttcgct ataaggagta atggtgttga gctgtgtact   1020
cggcgcattt cgagatgtag attcgactta agtggagatt ggagtttcat aggagggtcc   1080
agaattgttg taaaacctaa agctgcaaga tcggttcgct atacaaaaag aagtcaaata   1140
catgcttcat gtaatctttt ttcatctaat ctaaaattg tacaagctgt tccttagttc   1200
atataattta ccattcakta gaattggctg tgasggcgtt tgaacataaw aaagttaaat   1260
tgytttcwta taacctataa gttttttcs tawsttatat tckagagctt acraaaataa   1320
rctgaaaaca acttatggac atgtcgtaac ctgtttccag aaactatact aaacagtctc   1380
ataasttctt atgccaataa ataagctcaa ataastcaat ccaaacagga atgcatttaa   1440
tttttargtt accattttg gtggcgttat cataaagtag attactgtaa gtacttttgt   1500
cttatcatct ttatatgaac aacgaaactg gaggcagtgg ttaatatctg ttcattgatc   1560
atggtgtaca atgctatata tgataartta taaccttgca atgtgttgct gaaggcaata   1620
tggttcacaa ttcatgcttt agttgagtta gggtctgttt ggattckctt atttgagttt   1680
accttctaac ataagcattt gtgagactgt ttgagagagt ttatggaaac aacttatata   1740
cgacatgtgc ataacttgtt ttaagttaat ttttataaat tctccaagat agcttatgaa   1800
aacaacttac agattatatg aaaacagctc gactttattt tatttttgt tatagaaata   1860
acatatgcat aagcacttat atgataaaca aggttttctt gtttaggtgg ataccattga   1920
cttgaattgc ttgttmtaat atacytgaaa attgaytayg atctatgctt aaattgcttg   1980
ttctgcatat tcaytgtggt tcatgggatc tcaacttgct agcactgtat ttacatgggg   2040
aacgattgca gtgctcccgt tttacaccct tatggttcta gccccgaaat ccgagctggt   2100
acgtttcttt tttgtatttg tgaaaaatta tgattagtaa tctcatttca caattcatat   2160
tcagttatga tattcttttt catttcattt atttggttat gattctgata tgctgattcg   2220
gttttctgaa atgcaaaaat acagaccaaa aagtctatgg aaagtaattt accatatgta   2280
gtgctcggcg ttctatacgc ttatttgttg tgcctttctt ggacccctga aacagttcga   2340
ttgattttcg cgagtaaata cttactacct gaggtgtgta ttcatttatt aatgaagtta   2400
aattttcttt ctctaaagag ttcaattatc aataattgtg ttatatttgc atactctatg   2460
cagcttacta gcatagggaa aatgttctct agtgagttga ctttagcctc tgcttggatt   2520
cacctttgg ttgttgatct ttttgctgca aggtcctgat tttatctctt tgtttttgtt   2580
gctcagtaat gagattttga cacaaatttg acaaaaaaaa gtagaaaaca atttggatag   2640
ttaatgccgt tcgaatatgc ggttaattac atagtgaatg gttaatgaat attacaaaat   2700
acaaaatgtc acaagtcatt aaccctgatt ttgaacgccg ttaatcataa actttaggtg   2760
ttcaaacata cgtgatattc attaaccatt ccaattatgt tcacgatctt caggttttca   2820
aatatacata atattctatt aatcacaatt tttgttcaaa tatacaaatg taattgtggt   2880
taatgacatt caaaatagtg gttaattgtg atctattgat gggtaatgag ttatgacact   2940
ttgttataat cagtaaccat ctactaaatg taattaacct tatatttgaa ctacattaac   3000
atttaaattg ttgtcaaatt ttatggtcta attttgtgtc aaaataacac ggctctttct   3060
```

```
catgcttaaa ttatttttct gatagtattt gtggttctaa atccaggcat attttccgcg   3120

atggaatgga gaatcaaatt gaaacacgac attcggtttc cttttgcttg ttcttttgcc   3180

ctgttgggat tgtaactcat gtcatcacca aagcaatgac cataaaaaca agaaaagagg   3240

gtcatggtt                                                           3249


<210> SEQ ID NO 26
<211> LENGTH: 1845
<212> TYPE: DNA
<213> ORGANISM: Cichorium intybus

<400> SEQUENCE: 26

atggctttct cttcttgtct ttgccaccat caattggcac tcaaggtatt ggttaatttc     60

ccttttact ctctctatgt gtgtttgcat atgctcaaac gacttcactt tcacgaattc    120

atggtttatt tggcattttg cgatttgggt acgagtcatt tcgcgttatt ggtactaaat    180

ctggttgatt ttgccgattt aactaccagt gtcatccaat ttgtgcattt tcacatgttt    240

ttagctacct cacttttaca tattcctgtt tgtttgcgaa tttactatct gggtgtgatt    300

cagtttgctg tgttcgtgtt aatttggttg ttttggctca tttgattctg tttattacat    360

ccatttctgt attgtgtgac tgcagattga atcattcact ttacatatac atattatgct    420

gtctgtaaat ctattcgttt gtatcttctc cccaattgaa ttggttcact tttccgattt    480

tgatttcggt tagcagttta gggttcatag atgtttatgt tcaaattaga accatcaaaa    540

gggttacatt agtgagaaat cttgaagatg ttaaatcttt gttgcagatc aacctcttaa    600

cgagtccatc aaaacccaca ttcgctctta aagccatgaa caccgaattt tacggaatac    660

atatcggaag caagctagga aatcaatgga gttttatgaa aggatcacaa gccataatca    720

gaccgaaccc tggaagcttc aatctgcatc aaaaaagctc aaaattgcaa gcatcatgta    780

atcctttcgt accctttgtt tatcatgata caatttatcg attaaacatc caaaactttg    840

ttaatcttat cgtttttag ttcgattgga tattttttca tgtagggttt gcgagtatgc    900

atttagcgag cgatgctttt acattaggaa ccgctgctgt tcttccattc tacaccctta    960

tggtcgcagc tccaaaatcc gaattggtaa ggtttataat gttgtcataa agcaaagaaa   1020

attaaaaaaa aaacaaaaaa aaaaaaaaaa ttcattcaaa tacctatatc aatatagttg   1080

gaatttaagt gatgtttctt tttgactcat ttaaagtgtt gaatggataa attgtttttt   1140

ttttcttttt tgggtaaagt gtcgaacatg gtatatatta attgtttaat atattaagtt   1200

cattaagtaa aaaagaagct aattgtttac aaatttggtt gacattaatg cagacgaaaa   1260

agtgtatgag aagtagcata ccgtatgtgg tactcggggt tttatactcg tatcttcttt   1320

acctctcgtg gacgcccgac acagtccgat taatgtttgc aagcaaatac tggctgcccg   1380

aagtatgatt ttacacccct atagtttgct agatagccga cttttaaccc tagtgatggt   1440

tttatttgca gcttccgggt gttgctaaga tgttttctaa tgagatgaca ttagcctccg   1500

cttggatcca tttgttagcc gtcgacctct atgctgcaag gtaggagggc atttacgtct   1560

tttacacaaa caacatatcg aaagctagtc catgtcccac cttcttccgt aggatgaaaa   1620

attgcaattt ttttcccctg tacctgtacc tgtacctgta cctgatgaat tgtggttttg   1680

attggtggaa acagacaggt gtatcatgat ggattggaga aggagatcga gacacgacat   1740

tcggtttctc tttgtttgtt gttttgtccg attgggatac ttgttcatgc catcaccaag   1800

gctttgatta gtacatatag agaatcaaaa acagagattc attga                   1845
```

-continued

<210> SEQ ID NO 27
<211> LENGTH: 687
<212> TYPE: DNA
<213> ORGANISM: Allium cepa

<400> SEQUENCE: 27
atgcctctcc tttgctcctg cgattccagg atctataaac aggcaactcc attgtcaaat 60
caactgaata aatggcgagg tcttagttca catgcccaac aattcattcc taatggaagc 120
aaagatatag ttcaatggag ttttaaagga gggtcaaaga tagttattca accaaaaata 180
tcaaagatca gttaccacaa aagaggctcc gacatatctg cttattggat tcctacatcg 240
caaatagctt cgaatgcctt cacaatggga accgttgccg ttcttccatt ttatacgttg 300
atggttgttg ctcccaactc aaagcttaca aaaaggacaa tggaaagcag cataccgtat 360
gttgttcttg gtatgctata catgtatctt ctatatctat cgtggacacc tgagacgttg 420
gggtatatat ttgcaactaa atattggctg cccgagttat ccggcatatc aaaaatgttc 480
tcaaatgaaa cttgcacgtc ttctgcctgg attcatctac tgactgtaga tctttttgcc 540
gcaagacaag tattccaaga tggtataaag aacaagatag aaacccgaca ttctgtttca 600
ttgtgccttc tctgttgtcc aattggtatc gccactcacg caattacaaa agctctgaag 660
agggtgtcag atagtcgatc acactga 687

<210> SEQ ID NO 28
<211> LENGTH: 750
<212> TYPE: DNA
<213> ORGANISM: Allium cepa

<400> SEQUENCE: 28
atgtctctcc attacagctt ttgcaacacc cgcatctctc atcaggttgt tcattcatgg 60
aatgctccag atagatatgc agtttatgca tttttatcag ctagaaataa acatgatgaa 120
catattgggc gacaggtagc acatacaaaa agcagaaaca gggttaaatg gagcttcaga 180
ggaggatcag agctgtttat tcaaccaaaa gccacaagga ctgaccgtca aaaacatcga 240
tctgctctgt taacatcgtg cttaacaagt tcacaaattg ctgcaaaagc ttttacatgg 300
ggaaccattg cagttcttcc attctacaca ctaatggtag tagctcccaa tgctaaactt 360
actaaaagag ccatagaaag caacacacca tacatcattc ttggagcaat atacagctac 420
cttctctacc tgtcctggag tccttccaca ttgcgaacaa tgttcgctag taaatactgg 480
ttgcctcagt tatctggcat ctgcagcatg ttctcgaagg aaatgaccgt tgcttcagct 540
tggattcact tgctagctgt ggatctcttc gctgccagac aagtatactg tgatggcata 600
ttgaacaaca tagaaacaag gcattctatt tcattgtgcc ttctcttctg cccaatcggg 660
attgcgattc atgccattac caaggcactt accaaatatt ttttgaacta taatttttcg 720
gaagagatga aactggggct aaggagttag 750

<210> SEQ ID NO 29
<211> LENGTH: 747
<212> TYPE: DNA
<213> ORGANISM: Hordeum vulgare

<400> SEQUENCE: 29
atggccgccc ctcttccctc cccccttccc cgagcccggc agctccacca cctcgtcgac 60
tcccggcaag aaatggcggc ctcccccacc gccctcgccc tcgccctctc ccccaccacg 120
cgggtggttg tcaggcggac gccggcgccg cgcgtggccg ccgtctcccc cggccagctc 180

```
cgcgcgagct cctggggcgc gccgctccct ctccggccgg agctcgccgc ggcccctcct    240

cgacccggcg ccgcccgccg cagggcgcct ctgctccggc ctcgagcatg gctgtcgacg    300

tcccagatcg ccagctccgc cttcaccctg ggcaccgtcg ccgtgctccc cttctacacg    360

ctcatgatcg ccgcccccaa cgccaacatc actaagcgca cagtggagag caccgccccc    420

tacgtggccc tcggcatcct ctacgcctac ttgctctacc tctcctggac ccccgacacc    480

atccgcgcca tgttcgccag caagtactgg ctcccggagt tgcctggcat tgtgaggatg    540

tttgcgagcg agatgaccgt cgcctccgcc tggatccacc tccttgccgt cgacctcttc    600

gccgcaagac aggtgtacca tgatggcatc aagaacaaca tcgagaccag gcattcggtt    660

tccctgtgcc tgctcttctg ccccatcggg atcgccgctc acgcgctcac taaggtactg    720

gcggggtcga cagggcgatc gcactga                                         747


<210> SEQ ID NO 30
<211> LENGTH: 283
<212> TYPE: PRT
<213> ORGANISM: Daucus carota

<400> SEQUENCE: 30

Met Asn Lys Phe Val Leu Glu Asn Gln Asn Ala Leu Leu Val Ser Ile
1               5                   10                  15

Leu Lys Leu Gly Gln Tyr Leu Pro Ser Trp Thr Trp Glu Leu Leu Lys
            20                  25                  30

Tyr Leu Ser Leu Tyr Cys Leu Pro Asn Ala Tyr Asp Glu Asn Leu Glu
        35                  40                  45

Thr Glu Cys Leu Thr Glu His Ser Ser Leu Thr Arg Lys Gly Phe Tyr
    50                  55                  60

Asn Ile Ser Lys Ile Gln Leu Asn Pro Val Ala Ile Glu Gly Thr Asn
65                  70                  75                  80

Ser Asp Leu Tyr Gly Gln His Val Val Leu Trp Thr Lys Met Arg Lys
                85                  90                  95

Glu Trp Ser Phe Lys Arg Gly Ser Ile Ser Ile Ala Gly Pro Thr Met
            100                 105                 110

Glu Arg Phe Val Leu His Arg Lys Ser Ser Gly Val Gln Ala Ser Trp
        115                 120                 125

Phe Thr Asn Ser Gln Ile Ala Ser Ser Val Phe Thr Leu Ala Thr Ala
    130                 135                 140

Ala Val Leu Pro Phe Tyr Thr Leu Met Val Leu Ala Pro Lys Ala Thr
145                 150                 155                 160

Leu Thr Lys Lys Cys Ile Gln Ser Ala Val Pro Tyr Val Gly Leu Gly
                165                 170                 175

Leu Leu Tyr Ala Tyr Leu Leu Tyr Leu Ser Trp Thr Pro Asp Thr Phe
            180                 185                 190

Arg Leu Met Phe Ala Ser Gln Tyr Trp Leu Pro Glu Leu Ser Gly Ile
        195                 200                 205

Ala Lys Met Phe Ser Ser Glu Leu Thr Leu Ala Ser Ala Trp Ile His
    210                 215                 220

Leu Leu Ala Val Asp Leu Phe Ala Ala Arg Gln Ile Phe Gln Asp Gly
225                 230                 235                 240

Leu Gln Asn Ser Val Glu Thr Arg His Ser Val Ser Phe Cys Leu Leu
                245                 250                 255

Phe Cys Pro Ile Gly Ile Leu Ser His Glu Ile Thr Lys Ala Leu Thr
            260                 265                 270
```

```
Thr Gly Gly Arg Thr Ala Lys Arg Glu Ile His
        275                 280


<210> SEQ ID NO 31
<211> LENGTH: 261
<212> TYPE: PRT
<213> ORGANISM: Daucus carota

<400> SEQUENCE: 31

Met Ala Ser Leu Ser Cys Leu Cys Ser Ser Pro Leu Phe Leu Lys Asn
1               5                   10                  15

Asp Glu Ser Arg Leu Ala Asn Lys Ser Leu Leu Ala Tyr Thr Arg Lys
            20                  25                  30

Asp Arg Ile Thr Thr Tyr Cys Leu Asn Ser Val Glu Thr Asp Pro Phe
        35                  40                  45

Ser Arg His Pro His Ser Ile Lys Thr Lys Arg Trp Ser Phe Lys Gly
    50                  55                  60

Gly Ser Arg Val Ile Thr Gly Pro Asn Ile Gln Arg Phe Ala Cys Tyr
65                  70                  75                  80

Arg Lys Ser Cys Gly Val Tyr Ala Leu Trp Leu Thr Asn Pro Gln Ile
                85                  90                  95

Ala Ser Ser Ala Phe Thr Leu Gly Thr Ala Ala Val Leu Pro Tyr Tyr
            100                 105                 110

Thr Leu Met Val Val Ala Pro Lys Ser Glu Leu Thr Lys Lys Ser Ile
        115                 120                 125

Glu Ser Gly Ile Pro Tyr Val Ala Leu Gly Leu Leu Tyr Gly Tyr Leu
    130                 135                 140

Leu Tyr Leu Ser Trp Thr Pro Asp Thr Met Lys Met Met Phe Ala Ser
145                 150                 155                 160

Glu Tyr Trp Leu Pro Glu Leu Ser Gly Ile Ala Lys Met Phe Ser Ser
                165                 170                 175

Glu Met Thr Leu Ala Ser Ala Trp Ile His Leu Leu Ala Val Asp Leu
            180                 185                 190

Phe Ala Ala Arg Gln Val Tyr Gln Asp Gly Leu Glu Asn Lys Ile Glu
        195                 200                 205

Thr Arg His Ser Ile Ser Leu Cys Leu Leu Phe Cys Pro Ile Gly Ile
    210                 215                 220

Ile Ser His Val Val Thr Lys Ala Leu Thr Lys Ser Thr Glu Phe Pro
225                 230                 235                 240

Gly Phe Ala Phe His Asn Phe Ser Arg Leu Phe His Asp Ile Leu Leu
                245                 250                 255

Thr Ile Ala Asn Phe
            260


<210> SEQ ID NO 32
<211> LENGTH: 234
<212> TYPE: PRT
<213> ORGANISM: Cichorium endivia

<400> SEQUENCE: 32

Met Ala Phe Ser Ser Cys Leu Cys His His Gln Leu Ala Leu Lys Ile
1               5                   10                  15

Asn Leu Leu Thr Ser Pro Ser Lys Pro Thr Phe Val Leu Lys Ala Met
            20                  25                  30

Asn Thr Glu Phe Tyr Gly Ile His Ile Gly Ser Lys Ile Glu Asn Gln
        35                  40                  45
```

-continued

```
Trp Ser Phe Met Lys Gly Ser Arg Ala Ile Ile Arg Pro Asn Pro Gly
    50                  55                  60

Ser Phe Asn Leu His Gln Lys Ser Ser Lys Leu Gln Ala Ser Trp Phe
65                  70                  75                  80

Ala Ser Met His Leu Ala Ser Asp Ala Phe Thr Leu Gly Thr Ala Ala
                85                  90                  95

Val Leu Pro Phe Tyr Thr Leu Met Val Ala Ala Pro Lys Ser Glu Leu
            100                 105                 110

Thr Lys Lys Cys Met Arg Ser Ser Ile Pro Tyr Val Val Leu Gly Val
        115                 120                 125

Leu Tyr Ser Tyr Leu Leu Tyr Leu Ser Trp Thr Pro Asp Thr Ile Arg
    130                 135                 140

Leu Met Phe Ala Ser Lys Tyr Trp Leu Pro Glu Leu Pro Gly Val Ala
145                 150                 155                 160

Lys Met Phe Ser Asn Glu Met Thr Leu Ala Ser Ala Trp Ile His Leu
                165                 170                 175

Leu Ala Val Asp Leu Tyr Ala Ala Arg Gln Val Tyr His Asp Gly Leu
            180                 185                 190

Glu Lys Glu Ile Glu Thr Arg His Ser Val Ser Leu Cys Leu Leu Phe
        195                 200                 205

Cys Pro Ile Gly Ile Leu Val His Ala Ile Thr Lys Ala Leu Ile Ser
    210                 215                 220

Thr Tyr Arg Glu Ser Lys Thr Glu Ile His
225                 230


<210> SEQ ID NO 33
<211> LENGTH: 226
<212> TYPE: PRT
<213> ORGANISM: Solanum melongena

<400> SEQUENCE: 33

Met Asn Cys Trp Ala Pro Ala Ser Val Ser Leu Ser Thr Arg Arg Asn
1               5                   10                  15

His Thr Ala Phe Leu Ala Leu Arg Glu Ile Ile Ser Gln Arg Ile Gly
            20                  25                  30

Gly Phe Gly Thr Lys Leu Ser Ser Gly Gly Ser Ser Leu Gly Gly Ser
        35                  40                  45

Arg Val Ile Ile Gln Leu Asn Leu Gln Arg Thr Leu Ser Gln Arg Lys
    50                  55                  60

Ser Ser Arg Val His Ala Cys Trp Leu Pro Ser Ser Glu Ile Ala Ser
65                  70                  75                  80

Thr Ala Phe Thr Val Gly Thr Ala Ala Val Leu Pro Phe Tyr Thr Val
                85                  90                  95

Met Val Val Ala Pro Lys Ala Glu Leu Thr Arg Lys Ala Met Lys Ser
            100                 105                 110

Ser Ile Pro Tyr Ile Val Leu Gly Leu Leu Tyr Ala Tyr Leu Leu Tyr
        115                 120                 125

Leu Ser Trp Thr Pro Asp Thr Ile Arg Leu Met Phe Ala Ser Lys Tyr
    130                 135                 140

Trp Leu Pro Glu Leu Ser Gly Ile Ala Lys Met Phe Ser Asn Glu Val
145                 150                 155                 160

Thr Leu Ala Ser Ala Trp Ile His Leu Leu Ala Ile Asp Leu Phe Ala
                165                 170                 175

Ala Arg Gln Val Tyr His Asp Gly Leu Gln Asn Asp Ile Glu Thr Arg
            180                 185                 190
```

His Ser Val Thr Leu Cys Leu Leu Phe Cys Pro Val Gly Ile Leu Thr
195 200 205

His Cys Ile Thr Lys Ala Leu Thr Ser Ser Pro Glu Lys Lys Gln His
210 215 220

Arg Thr
225

<210> SEQ ID NO 34
<211> LENGTH: 249
<212> TYPE: PRT
<213> ORGANISM: Solanum melongena

<400> SEQUENCE: 34

Met Ala Leu Ser Ser Thr Cys Phe Cys His Ser Gln Phe Ser Leu Lys
1 5 10 15

Met Glu Ser Trp Thr Pro Ala Leu Ser Ser Asn Ile Arg Cys Tyr Ile
20 25 30

Arg Arg Asn Gln Phe Pro Ser Ser Met Leu Lys Thr Ile Asn Ser Asp
35 40 45

Leu Ser Ser Gln Gln Val Gln Glu Arg Gly Thr Lys His Ser Asn Gly
50 55 60

Ser Ser Phe Leu Gly Gly Ser Arg Val Met Arg Gln Pro Asn Leu Gln
65 70 75 80

Asn Leu Pro Gln Arg Arg Ser Cys Arg Val Ser Ala Met Trp Leu Pro
85 90 95

Ser Ser Gln Val Ala Ser Ser Val Phe Thr Leu Gly Thr Ala Ala Val
100 105 110

Leu Pro Phe Tyr Thr Leu Met Val Ala Ala Pro Lys Ala Glu Leu Thr
115 120 125

Arg Lys Leu Met Gly Ser Ala Ile Pro Tyr Val Ala Leu Gly Leu Leu
130 135 140

Tyr Thr Tyr Leu Leu Tyr Leu Ser Trp Thr Pro Asp Thr Ile Arg Leu
145 150 155 160

Met Phe Ala Ser Lys Tyr Trp Leu Pro Glu Leu Ser Ser Ile Ala Lys
165 170 175

Met Phe Ser Ser Glu Met Thr Leu Ala Ser Ala Trp Ile His Leu Leu
180 185 190

Ala Val Asp Leu Phe Ala Ala Arg Gln Val Tyr His Asp Gly Leu Gln
195 200 205

Asn Gly Ile Glu Thr Arg His Ser Val Ser Leu Cys Leu Leu Phe Cys
210 215 220

Pro Ile Gly Ile Val Ile His Leu Leu Thr Lys Ala Val Leu Ser Asn
225 230 235 240

Ala Glu Asn Ile Val Pro Arg Thr His
245

<210> SEQ ID NO 35
<211> LENGTH: 246
<212> TYPE: PRT
<213> ORGANISM: Solanum lycopersicum

<400> SEQUENCE: 35

Met Tyr Phe Ser Ser Ser Ser His Val Ser Leu Lys Met Asn Cys Trp
1 5 10 15

Ala Pro Ala Leu Ala Ser Lys Val Pro Leu Asn Thr Arg Arg Asn Gln
20 25 30

```
Thr Ala Ser Pro Ala Leu Arg Gln Met Lys Ser Asp Leu Leu Ser Gln
        35                  40                  45

Arg Ile Gly Gly Phe Gly Thr Asn Leu Ser Ser Gly Gly Ser Ser Leu
    50                  55                  60

Gly Gly Ser Arg Ile Ile Thr Gln Leu Asn Leu Gln Arg Thr Leu Ser
65                  70                  75                  80

Arg Arg Lys Ser Pro Met Val Ser Ala Cys Trp Val Pro Ser Ser Glu
                85                  90                  95

Val Ala Ser Thr Ala Phe Thr Val Gly Thr Ala Ala Val Leu Pro Phe
            100                 105                 110

Tyr Thr Val Met Val Val Ala Pro Lys Ala Glu Leu Thr Arg Lys Ala
        115                 120                 125

Met Lys Ser Ser Ile Pro Tyr Ile Val Leu Gly Leu Leu Tyr Ala Tyr
    130                 135                 140

Leu Leu Tyr Leu Ser Trp Thr Pro Asp Thr Ile Arg Leu Met Phe Ala
145                 150                 155                 160

Ser Lys Tyr Trp Leu Pro Glu Leu Ser Gly Ile Ala Lys Met Phe Ser
                165                 170                 175

Asn Glu Val Thr Leu Ala Ser Ala Trp Ile His Leu Leu Ala Ile Asp
            180                 185                 190

Leu Phe Ala Ala Arg Gln Val Tyr His Asp Gly Leu Gln Asn Asp Ile
        195                 200                 205

Glu Thr Arg His Ser Val Ser Leu Cys Leu Leu Phe Cys Pro Val Gly
    210                 215                 220

Ile Leu Thr His Cys Ile Thr Lys Ala Leu Thr Ser Ser Pro Glu Lys
225                 230                 235                 240

Lys Gln His Arg Thr His
                245


<210> SEQ ID NO 36
<211> LENGTH: 250
<212> TYPE: PRT
<213> ORGANISM: Solanum lycopersicum

<400> SEQUENCE: 36

Met Ala Leu Ser Ser Thr Cys Phe Ser His Ser Gln Phe Ser Leu Lys
1               5                   10                  15

Met Asp Cys Trp Thr Pro Ala Leu Ser Ser Asn Ile Leu Cys Tyr Ile
            20                  25                  30

Arg Arg Lys Gln Pro Pro Ser Ser Thr Leu Lys Thr Ile Asn Ser Asn
        35                  40                  45

Leu Leu Ser Gln Gln Val His Lys Arg Arg Thr Lys His Gly Asn Gly
    50                  55                  60

Trp Ser Phe Leu Gly Gly Ser Arg Val Lys Cys Gln Pro Asn Leu Gln
65                  70                  75                  80

Asn Leu Pro Gln Arg Arg Ser Tyr Arg Val Ser Ala Met Trp Leu Pro
                85                  90                  95

Ser Ser Gln Val Ala Ser Ser Val Phe Thr Leu Gly Thr Ala Gly Val
            100                 105                 110

Leu Pro Phe Tyr Thr Val Met Ile Ala Ala Pro Lys Ala Glu Leu Thr
        115                 120                 125

Arg Lys Leu Met Asp Ser Ala Ile Pro Tyr Ile Val Leu Gly Leu Leu
    130                 135                 140

Tyr Ala Tyr Leu Leu Tyr Leu Ser Trp Thr Pro Asp Thr Ile Arg Leu
```

```
145                 150                 155                 160

Met Phe Ala Ser Lys Tyr Trp Leu Pro Glu Leu Ser Gly Ile Ala Lys
                165                 170                 175

Met Phe Ser Ser Glu Met Thr Leu Ala Ser Ala Trp Ile His Leu Leu
            180                 185                 190

Ala Val Asp Leu Phe Ala Ala Arg Gln Val Tyr His Asp Gly Leu Gln
        195                 200                 205

Asn Gly Ile Glu Thr Arg His Ser Val Ser Leu Cys Leu Leu Phe Cys
    210                 215                 220

Pro Ile Gly Ile Val Ile His Leu Leu Thr Lys Ala Val Leu Leu Ser
225                 230                 235                 240

Ser Ala Glu Lys Thr Val Phe Arg Thr Asn
                245                 250


<210> SEQ ID NO 37
<211> LENGTH: 234
<212> TYPE: PRT
<213> ORGANISM: Capsicum annuum

<400> SEQUENCE: 37

Met Asn Cys Trp Thr Pro Ala Phe Val Ser Lys Val Pro Leu Asn Thr
1               5                   10                  15

Trp Arg Asn Gln Thr Ala Ser Leu Ala Leu Arg Glu Met Lys Ser Asp
            20                  25                  30

Leu Leu Ser Gln His Ile Gly Gly Phe Glu Thr Lys His Ser Ser Gly
        35                  40                  45

Gly Ser Ser Leu Ala Gly Ser Arg Val Thr Ile Gln Leu Asn His Gln
    50                  55                  60

Arg Thr Leu Ser Gln Arg Lys Ser Phe Arg Ala Ser Ala Cys Trp Leu
65                  70                  75                  80

Pro Ser Ser Glu Val Ala Ser Thr Ala Phe Thr Val Gly Thr Ala Val
                85                  90                  95

Val Leu Pro Phe Tyr Thr Ile Met Val Val Ala Pro Lys Ala Lys Leu
            100                 105                 110

Thr Lys Lys Ala Met Lys Ser Ser Ile Pro Tyr Ile Val Leu Gly Leu
        115                 120                 125

Leu Tyr Ala Tyr Leu Leu Tyr Leu Ser Trp Thr Pro Asp Thr Ile Arg
    130                 135                 140

Leu Met Phe Ala Ser Gln Tyr Trp Leu Pro Glu Leu Pro Gly Ile Ala
145                 150                 155                 160

Lys Met Phe Ser Asn Glu Val Thr Leu Ala Ser Ala Trp Ile His Leu
                165                 170                 175

Leu Ala Ile Asp Leu Phe Ala Ala Arg Gln Val Tyr His Asp Gly Leu
            180                 185                 190

Gln Asn Asp Ile Glu Thr Arg His Ser Val Ser Leu Cys Leu Leu Phe
        195                 200                 205

Cys Pro Val Gly Ile Leu Thr His Phe Ile Thr Lys Ala Leu Thr Ser
    210                 215                 220

Ser Pro Glu Lys Arg Gln Arg Arg Ile His
225                 230


<210> SEQ ID NO 38
<211> LENGTH: 232
<212> TYPE: PRT
<213> ORGANISM: Brassica oleracea
```

<400> SEQUENCE: 38

```
Met Ala Phe Ser Gln Pro Leu Ser Ser Ser Ser Leu Ser Met Thr Asn
1               5                   10                  15

Arg Ser Phe Val Ala Lys Ser Ser Val Thr Ala Ser Leu Ser Leu Asn
            20                  25                  30

Lys Ser Leu Lys Ile Arg Phe His Asn Arg Trp Ser Phe Asp Gly Gly
        35                  40                  45

Ser Arg Ile Val Leu Phe Pro Ser Val Ser Ser Asp Ser Ser Ser Leu
    50                  55                  60

Val His Lys Lys Arg Ser Cys Val Arg Ala Ser Trp Met Ala Thr Ser
65                  70                  75                  80

Gln Ile Ala Ser Ser Val Phe Ala Val Gly Thr Thr Ala Val Leu Pro
                85                  90                  95

Phe Tyr Thr Leu Met Val Val Ala Pro Lys Ala Glu Ile Thr Lys Lys
            100                 105                 110

Cys Met Glu Ser Ser Ile Pro Tyr Val Val Leu Gly Val Leu Tyr Ala
        115                 120                 125

Tyr Leu Leu Tyr Leu Ser Trp Thr Pro Glu Thr Leu Lys Tyr Met Phe
    130                 135                 140

Ser Ser Lys Tyr Leu Leu Pro Glu Leu Ser Gly Ile Ala Lys Met Phe
145                 150                 155                 160

Ser Ser Glu Met Thr Leu Ala Ser Ala Trp Ile His Leu Leu Val Ile
                165                 170                 175

Asp Leu Phe Ala Ala Arg Gln Val Phe Asn Asp Gly Leu Glu Asn Lys
            180                 185                 190

Ile Glu Thr Arg His Ser Val Ser Leu Cys Leu Leu Phe Cys Pro Val
        195                 200                 205

Gly Ile Val Ser His Val Val Thr Lys Ala Leu Thr Asn Ser Ser Thr
    210                 215                 220

Ser Asn Thr Asn Asn Gln Cys Lys
225                 230
```

<210> SEQ ID NO 39
<211> LENGTH: 247
<212> TYPE: PRT
<213> ORGANISM: Apium graveolens

<400> SEQUENCE: 39

```
Met Pro Leu Ser Ser Cys Leu Tyr Cys Tyr Gln Ile Ser Ser Leu Lys
1               5                   10                  15

Thr Glu His Ser Thr Leu Ser Thr Lys Pro Leu Cys Asn Ile Gly Gln
            20                  25                  30

Ser Arg Leu Asn Thr Val Ala Ile Glu Gly Ile Asn Ser Asp Leu Tyr
        35                  40                  45

Gly Gln His Leu Val Leu Trp Thr Lys Met Arg Lys Glu Trp Ser Phe
    50                  55                  60

Lys Gly Gly Ser Thr Ser Ile Ala Val Pro Thr Ile Gln Arg Ser Val
65                  70                  75                  80

Leu Tyr Arg Lys Ser Leu Glu Val Gln Ala Ser Trp Phe Thr Asn Ser
                85                  90                  95

His Ile Ala Ser Ser Val Phe Thr Leu Ala Thr Ala Ala Val Leu Pro
            100                 105                 110

Phe Tyr Thr Leu Met Val Leu Ala Pro Lys Ala Asn Leu Thr Lys Lys
        115                 120                 125
```

```
Cys Ile Gln Ser Thr Leu Pro Tyr Val Val Leu Gly Ile Leu Tyr Ala
    130                 135                 140

Tyr Leu Leu Tyr Leu Ser Trp Thr Pro Asp Thr Phe Arg Leu Met Phe
145                 150                 155                 160

Ala Ser Gln Tyr Trp Leu Pro Glu Leu Ser Gly Ile Ala Lys Met Phe
                165                 170                 175

Ser Ser Glu Leu Thr Leu Ala Ser Ala Trp Ile His Leu Leu Ala Val
            180                 185                 190

Asp Leu Phe Ala Ala Arg Gln Ile Phe Ile Asp Gly Leu Gln Asn Tyr
        195                 200                 205

Val Glu Thr Arg His Ser Val Ser Phe Cys Leu Leu Phe Cys Pro Ile
    210                 215                 220

Gly Ile Leu Ser His Glu Ile Thr Lys Ala Leu Thr Thr Gly Gly Arg
225                 230                 235                 240

Asn Thr Lys Arg Gln Ile Arg
                245


<210> SEQ ID NO 40
<211> LENGTH: 241
<212> TYPE: PRT
<213> ORGANISM: Apium graveolens

<400> SEQUENCE: 40

Met Ala Ser Phe Ser Cys Leu Cys Ser Ser Ser Leu Phe Val Lys Asn
1               5                   10                  15

Asp Asp Leu Arg Leu Thr Asn Arg Leu Leu Glu Ala Cys Phe Arg Lys
            20                  25                  30

Asp Gln Leu Thr Thr Cys Ala Leu Lys Ser Phe Lys Thr Asp Pro Phe
        35                  40                  45

Ser Arg His Pro Pro Ser Ile Lys Thr Lys Ser Arg Thr Glu Trp Ser
    50                  55                  60

Phe Lys Gly Gly Ser Arg Ala Ile Pro Gly Pro Thr Ile His Lys Phe
65                  70                  75                  80

Ala Arg Asn Arg Lys Ser Cys Gly Val Tyr Ala Ser Trp Phe Thr Asn
                85                  90                  95

Pro Gln Ile Ala Ser Gly Ala Phe Thr Leu Gly Thr Ala Ala Val Leu
            100                 105                 110

Pro Tyr Tyr Thr Leu Met Val Val Ala Pro Lys Ser Glu Leu Thr Lys
        115                 120                 125

Lys Ser Ile Glu Ser Gly Ile Pro Tyr Val Thr Leu Gly Leu Leu Tyr
    130                 135                 140

Gly Tyr Leu Leu Tyr Leu Ser Trp Thr Pro Asp Thr Met Arg Leu Met
145                 150                 155                 160

Phe Ala Ser Gln Tyr Trp Leu Pro Glu Leu Ser Gly Ile Ala Lys Met
                165                 170                 175

Phe Ser Ser Glu Met Thr Leu Ala Ser Ala Trp Ile His Leu Leu Ala
            180                 185                 190

Val Asp Leu Phe Ala Ala Arg Gln Val Tyr His Asp Gly Leu Glu Asn
        195                 200                 205

Lys Val Glu Thr Arg His Ser Ile Ser Leu Cys Leu Leu Phe Cys Pro
    210                 215                 220

Ile Gly Ile Ile Ser His Val Val Thr Lys Ala Leu Thr Lys Ser Ser
225                 230                 235                 240

Lys
```

-continued

<210> SEQ ID NO 41
<211> LENGTH: 250
<212> TYPE: PRT
<213> ORGANISM: Spinacia oleracea

<400> SEQUENCE: 41

```
Met Ala Leu Ser Ser Cys Phe Ala Tyr His Pro Gln Ile Ser Ser Lys
1               5                   10                  15

Ile Asp Cys Ser Val Leu Val Asp Lys Asn His His Gln Val Gly Leu
            20                  25                  30

Ser Pro Ser Leu Val Leu Ser Val Gln Gly Val Arg Asn Gly Ile Phe
        35                  40                  45

Ser Gln Lys Val Pro Lys Leu Arg Ala Glu Ile Met His Gly Cys Cys
    50                  55                  60

Phe Leu Gly Gly Leu Arg Ile Asp Ile Arg Pro Thr Val Asn Glu Ser
65                  70                  75                  80

Asn Phe Ser Arg Arg Asn Ser Gly Val Cys Tyr Ser Trp Leu Ser Asn
                85                  90                  95

Thr Gln Val Ala Ser Ser Ala Phe Thr Leu Gly Thr Ala Ala Val Leu
            100                 105                 110

Pro Phe Tyr Thr Leu Met Ile Val Ala Pro Lys Ala Glu Leu Thr Lys
        115                 120                 125

Lys Thr Met Lys Ser Ser Ile Pro Tyr Val Val Leu Gly Leu Leu Tyr
    130                 135                 140

Ala Tyr Leu Leu Tyr Leu Ser Trp Thr Pro Glu Thr Ile Arg Leu Met
145                 150                 155                 160

Phe Ala Ser Lys Tyr Trp Leu Pro Glu Leu Gln Gly Ile Ala Lys Met
                165                 170                 175

Phe Ser Ser Glu Met Thr Leu Ala Ser Ala Trp Ile His Leu Leu Val
            180                 185                 190

Val Asp Leu Phe Ala Ala Arg Asn Val Tyr Gln Asp Gly Leu Glu Lys
        195                 200                 205

Glu Val Glu Thr Arg His Ser Val Ser Met Cys Leu Leu Phe Cys Pro
    210                 215                 220

Val Gly Ile Leu Ser His Leu Ile Thr Thr Ala Leu Thr Arg Pro Ser
225                 230                 235                 240

Asp Lys Thr Arg His Ser Asp Thr Ile Ile
                245                 250
```

<210> SEQ ID NO 42
<211> LENGTH: 239
<212> TYPE: PRT
<213> ORGANISM: Valerianella locusta

<400> SEQUENCE: 42

```
Met Ala Phe Ser Ser Cys Phe Cys His Pro Gln Phe Ser Leu Lys Met
1               5                   10                  15

Asp Cys Ser Ile Ser Thr Val Lys Ser Ser Tyr Ile Thr Arg Asn Gln
            20                  25                  30

Lys Gln Leu Thr Asn Phe Thr Leu Gly Ser Thr Asn Gly Gln Pro Phe
        35                  40                  45

Gly Gln His Phe Ala Trp Lys Glu Ala Lys Leu Ser Cys Gly Ser Ser
    50                  55                  60

Phe Ser Gly Arg Ser Lys Ala Ile Val Ser Ser Asn Pro Arg Lys Leu
65                  70                  75                  80
```

-continued

```
Ile His Phe Arg Lys Tyr Cys Arg Ile Tyr Ala Ser Trp Trp Ser Asn
                85                  90                  95

Pro Thr Thr Ile Ala Asn Asn Val Phe Thr Leu Gly Thr Val Ala Val
            100                 105                 110

Leu Pro Phe Tyr Thr Leu Met Leu Val Ala Pro Lys Ala Glu Leu Thr
        115                 120                 125

Gln Lys Ser Met Glu Ser Ser Ile Pro Tyr Ile Val Leu Gly Val Leu
    130                 135                 140

Tyr Ala Cys Leu Leu Tyr Leu Ser Trp Ser Pro Asp Thr Leu Arg Leu
145                 150                 155                 160

Met Phe Ala Ser Lys Tyr Trp Leu Pro Glu Leu Pro Gly Ile Ala Lys
                165                 170                 175

Met Phe Ser Asn Glu Ile Thr Leu Ala Ser Ala Trp Leu His Leu Leu
            180                 185                 190

Ala Ile Asp Leu Tyr Ala Ala Arg Gln Val Tyr Lys Asp Gly Ile Glu
        195                 200                 205

Asn Asn Ile Glu Thr Arg His Ser Val Ser Ile Cys Leu Leu Phe Cys
    210                 215                 220

Pro Ile Gly Ile Ile Val His Tyr Ile Thr Lys Ala Leu Thr Ile
225                 230                 235


<210> SEQ ID NO 43
<211> LENGTH: 225
<212> TYPE: PRT
<213> ORGANISM: Raphanus sativus

<400> SEQUENCE: 43

Met Met Asn Arg Ser Ile Ile Ala Asn Ser Ser Val Arg Ala Ser Leu
1               5                   10                  15

Cys Leu Asn Lys Ser Arg Val Cys Val Asp Ser Leu Lys Ile Gln Phe
            20                  25                  30

Gln Asn Arg Trp Ser Phe Ile Gly Gly Ser Arg Leu Ala Phe Leu Pro
        35                  40                  45

Ser Leu Ser Ser Asn Pro Ser Ser Phe Val His Lys Lys Pro Ser Cys
    50                  55                  60

Val Arg Ala Ser Trp Leu Ala Thr Ser Gln Ile Ala Ser Ser Val Phe
65                  70                  75                  80

Ala Val Gly Thr Thr Ala Val Leu Pro Phe Tyr Thr Leu Met Val Val
                85                  90                  95

Ala Pro Lys Ala Glu Ile Thr Lys Lys Cys Met Glu Ser Ser Ile Pro
            100                 105                 110

Tyr Val Val Leu Gly Leu Leu Tyr Ala Tyr Leu Leu Tyr Leu Ser Trp
        115                 120                 125

Thr Pro Asp Thr Leu Lys Tyr Met Phe Ser Ser Lys Tyr Leu Leu Pro
    130                 135                 140

Glu Leu Ser Gly Ile Ala Lys Met Phe Ser Ser Glu Met Thr Leu Ala
145                 150                 155                 160

Ser Ala Trp Ile His Leu Leu Val Ile Asp Leu Phe Ala Ala Arg Gln
                165                 170                 175

Val Phe Asn Asp Gly Leu Glu Asn Lys Ile Glu Thr Arg His Ser Val
            180                 185                 190

Ser Leu Cys Leu Leu Phe Cys Pro Val Gly Ile Val Ser His Val Val
        195                 200                 205

Thr Lys Ala Leu Thr Asn Ser Ser Thr Ser Asn Thr Asn Asn Gln Cys
    210                 215                 220
```

```
Lys
225


<210> SEQ ID NO 44
<211> LENGTH: 234
<212> TYPE: PRT
<213> ORGANISM: Capsicum baccatum

<400> SEQUENCE: 44

Met Asn Cys Trp Thr Pro Ala Leu Val Ser Lys Val Pro Leu Asn Thr
1               5                   10                  15

Trp Arg Asn Gln Thr Ala Ser Leu Ala Leu Arg Glu Met Lys Ser Asp
            20                  25                  30

Leu Leu Ser Gln His Ile Gly Gly Phe Glu Ile Lys His Ser Cys Gly
        35                  40                  45

Gly Ser Ser Leu Ala Gly Ser Arg Val Thr Ile Gln Leu Asn His Gln
    50                  55                  60

Arg Thr Leu Ser Gln Arg Lys Ser Phe Arg Val Ser Ala Cys Trp Leu
65                  70                  75                  80

Pro Ser Ser Glu Val Ala Ser Thr Ala Phe Thr Val Gly Thr Ala Val
                85                  90                  95

Val Leu Pro Phe Tyr Thr Ile Met Val Val Ala Pro Lys Ala Lys Leu
            100                 105                 110

Thr Arg Lys Ala Met Lys Ser Ser Ile Pro Tyr Ile Val Leu Gly Leu
        115                 120                 125

Leu Tyr Ala Tyr Leu Leu Tyr Leu Ser Trp Thr Pro Asp Thr Ile Arg
    130                 135                 140

Leu Met Phe Ala Ser Gln Tyr Trp Leu Pro Glu Leu Pro Gly Ile Ala
145                 150                 155                 160

Lys Met Phe Ser Asn Glu Val Thr Leu Ala Ser Ala Trp Ile His Leu
                165                 170                 175

Leu Ala Ile Asp Leu Phe Ala Ala Arg Gln Val Tyr His Asp Gly Leu
            180                 185                 190

Gln Asn Asp Ile Glu Thr Arg His Ser Val Ser Leu Cys Leu Leu Phe
        195                 200                 205

Cys Pro Val Gly Ile Leu Thr His Phe Ile Thr Lys Ala Leu Thr Ser
    210                 215                 220

Ser Pro Glu Lys Arg Gln Arg Arg Ile His
225                 230


<210> SEQ ID NO 45
<211> LENGTH: 266
<212> TYPE: PRT
<213> ORGANISM: Chenopodium quinoa

<400> SEQUENCE: 45

Met Ala Phe Ser Ser Cys Phe Ala Phe His Pro Gln Ile Ser Ser Ser
1               5                   10                  15

Lys Ile Asp Cys Arg Val Leu Val His Lys Ile His His Lys Ala Gly
            20                  25                  30

Leu Ser Pro Ser Leu Ala Leu Ser His Gln Gly Val Ser Thr Glu Ile
        35                  40                  45

Tyr Ser Gln Gln Val Ser Lys Leu Arg Pro Asp Val Lys His Asp Trp
    50                  55                  60

Cys Phe Leu Gly Gly Leu Arg Ile Asp Val Arg Pro Lys Val Asn Lys
65                  70                  75                  80
```

```
Phe Val Phe Ser Arg Lys Asn Ser Gly Val Cys Tyr Ser Cys Ser Thr
                85                  90                  95

Phe Asn Pro Met Gln His Thr Leu Leu Val Ile Ser Gly Leu Pro Asp
            100                 105                 110

Pro Gln Ile Ala Thr Ser Ala Phe Thr Ile Gly Thr Ala Ala Val Leu
        115                 120                 125

Pro Phe Tyr Thr Leu Met Val Val Ala Pro Lys Ala Glu Leu Thr Lys
    130                 135                 140

Lys Thr Met Lys Ser Ser Ile Pro Tyr Val Val Phe Gly Leu Leu Tyr
145                 150                 155                 160

Ala Tyr Leu Leu Tyr Leu Ser Trp Thr Pro Glu Thr Ile Ser Leu Met
                165                 170                 175

Phe Ala Ser Lys Tyr Trp Leu Pro Glu Leu Gln Gly Ile Ala Lys Met
            180                 185                 190

Phe Ser Ser Glu Met Thr Leu Ala Ser Ala Trp Ile His Leu Leu Val
        195                 200                 205

Val Asp Leu Tyr Ala Ala Arg Gln Val Tyr His Asp Gly Leu Gln Asn
    210                 215                 220

Glu Ile Glu Thr Arg His Ser Val Ser Met Cys Leu Leu Phe Cys Pro
225                 230                 235                 240

Ile Gly Ile Leu Ser His Leu Ile Thr Ser Ser Leu Thr Lys Pro Ala
                245                 250                 255

Glu Lys Thr Arg His Thr Asp Thr Ile Ile
            260                 265
```

<210> SEQ ID NO 46
<211> LENGTH: 240
<212> TYPE: PRT
<213> ORGANISM: Fagopyrum esculentum

<400> SEQUENCE: 46

```
Met Ala Leu Ser Thr Cys Phe Ser His Ala Arg Ile Phe Leu Gln Asn
1               5                   10                  15

Asp Met Gly Ser Lys Val Gln Arg Thr Gln Leu Asn Phe Arg Leu Glu
            20                  25                  30

Thr Arg His Thr Val Ser Arg Gln Ser Leu Asn Ile Gln His Phe Cys
        35                  40                  45

Gln Asn Pro Leu Ser Glu Gln Ser Leu Gly Leu Gly Cys Met Thr Ala
    50                  55                  60

Ala Arg Thr Lys Ile Asn Thr Thr Ser Leu Ser Lys Lys Arg Pro Gly
65                  70                  75                  80

Ile Cys Ser Cys Trp Met Val Gly Ser Gln Ile Ala Ser Asn Ala Phe
                85                  90                  95

Thr Leu Gly Thr Ala Ala Val Leu Pro Phe Tyr Thr Leu Met Val Phe
            100                 105                 110

Ala Pro Lys Ala Glu Met Thr Lys Lys Ala Met Asp Ser Ser Ile Pro
        115                 120                 125

Tyr Val Met Leu Gly Leu Val Tyr Ala Tyr Leu Leu Tyr Leu Ser Trp
    130                 135                 140

Thr Pro Asp Thr Ile Lys Leu Met Phe Ala Ser Lys Tyr Trp Leu Pro
145                 150                 155                 160

Glu Leu Pro Gly Ile Ala Lys Met Phe Ser Asn Glu Met Thr Leu Ser
                165                 170                 175

Ser Ala Trp Ile His Leu Leu Ile Val Asp Leu Phe Ala Ala Arg Arg
```

180 185 190

Ile Tyr His Asp Gly Leu Glu Asn Lys Ile Glu Thr Arg His Ser Val
195 200 205

Ser Met Cys Leu Leu Val Cys Pro Ile Gly Ile Leu Met His Thr Ile
210 215 220

Thr Lys Ala Leu Thr Arg Thr Arg Val Glu Ser Ser Lys His Asn Val
225 230 235 240

<210> SEQ ID NO 47
<211> LENGTH: 242
<212> TYPE: PRT
<213> ORGANISM: Lens esculenta

<400> SEQUENCE: 47

Met Ser Phe Ser Ser Cys Tyr Ser His Leu Pro Leu Ala Phe Asn Lys
1 5 10 15

Asp Ile Lys Leu Cys Arg Thr Val Gly Gln Glu Lys Leu Asn Phe Pro
20 25 30

Phe Thr Ile Arg Ser Asn Ser Val Glu Leu Cys Thr Arg Arg Ile Ser
35 40 45

Ser Ser Arg Ala Gly Leu Ser Gly Asp Trp Ser Phe Ile Gly Gly Ser
50 55 60

Lys Ile Val Val Lys Pro Lys Ala Thr Thr Ser Phe Arg Asn Pro Lys
65 70 75 80

Arg Ser Gln Ile His Ala Ser Trp Phe Ile Gly Ser Gln Leu Ala Ser
85 90 95

Thr Val Phe Thr Trp Gly Thr Ile Ala Val Leu Pro Tyr Tyr Thr Leu
100 105 110

Met Val Phe Ala Pro Lys Ser Glu Leu Thr Lys Lys Ala Met Gln Ser
115 120 125

Asn Leu Pro Tyr Val Ile Leu Gly Val Leu Tyr Ala Tyr Leu Leu Cys
130 135 140

Leu Ser Trp Thr Pro Glu Thr Val Arg Leu Ile Phe Ala Ser Lys Tyr
145 150 155 160

Leu Leu Pro Glu Leu Ser Ser Ile Gly Lys Met Phe Ser Ser Glu Leu
165 170 175

Thr Leu Ala Ser Ala Trp Ile His Leu Leu Val Val Asp Leu Phe Ala
180 185 190

Ala Arg His Ile Phe Arg Glu Gly Met Glu Asn Gln Ile Glu Thr Arg
195 200 205

His Ser Val Ser Phe Cys Leu Phe Phe Cys Pro Ile Gly Ile Leu Thr
210 215 220

His Val Ile Thr Lys Ala Met Thr Lys Thr Thr Arg Lys Gln Gly His
225 230 235 240

Gly Leu

<210> SEQ ID NO 48
<211> LENGTH: 239
<212> TYPE: PRT
<213> ORGANISM: Medicago sativa

<400> SEQUENCE: 48

Met Ser Phe Ser Ser Cys Tyr Ser His Ser Pro Leu Pro Phe Asn Lys
1 5 10 15

Asp Ile Lys Leu Cys Arg Thr Val Gly Gln Leu Lys Leu Asn Phe Pro
20 25 30

```
Phe Ser Ile Arg Ser Asp Gly Val Thr Lys His Ile Ser Arg Ser Arg
        35                  40                  45

Phe Ser Leu Ser Gly Asp Trp Ser Phe Ile Gly Gly Ser Arg Ile Val
    50                  55                  60

Val Lys Pro Lys Ala Thr Arg Ser Val Arg His Pro Lys Arg Ser Gln
65                  70                  75                  80

Ile His Ala Ser Trp Phe Ile Gly Ser Gln Leu Pro Ser Thr Val Phe
                85                  90                  95

Thr Trp Gly Thr Ile Ala Val Leu Pro Phe Tyr Thr Leu Met Val Leu
            100                 105                 110

Ala Pro Lys Ser Asp Leu Thr Lys Lys Ser Met Glu Ser Ser Leu Pro
        115                 120                 125

Tyr Val Val Leu Gly Ile Leu Tyr Ala Tyr Leu Leu Cys Leu Ser Trp
    130                 135                 140

Thr Pro Glu Thr Val Arg Leu Ile Phe Ala Ser Lys Tyr Leu Leu Pro
145                 150                 155                 160

Glu Leu Ser Ser Ile Gly Lys Met Phe Ser Ser Glu Leu Thr Leu Ala
                165                 170                 175

Ser Ala Trp Ile His Leu Leu Val Val Asp Leu Phe Ala Ala Arg His
            180                 185                 190

Ile Phe His Asp Gly Leu Lys Asn Gln Ile Glu Thr Arg His Ser Val
        195                 200                 205

Ser Phe Cys Leu Phe Phe Cys Pro Ile Gly Ile Leu Thr His Val Ile
    210                 215                 220

Thr Lys Ala Met Thr Lys Thr Thr Arg Lys Asp Gly His Gly Leu
225                 230                 235
```

<210> SEQ ID NO 49
<211> LENGTH: 130
<212> TYPE: PRT
<213> ORGANISM: Pisum sativum

<400> SEQUENCE: 49

```
Met Val Phe Ala Pro Lys Ser Glu Leu Thr Lys Lys Ser Met Glu Ser
1               5                   10                  15

Tyr Leu Pro Tyr Val Ile Leu Gly Val Leu Tyr Ala Tyr Leu Leu Phe
            20                  25                  30

Leu Ser Trp Thr Pro Glu Thr Val Arg Leu Ile Phe Ala Ser Lys Tyr
        35                  40                  45

Leu Leu Pro Glu Leu Ser Ser Ile Gly Lys Met Phe Ser Ser Glu Leu
    50                  55                  60

Thr Leu Ala Ser Ala Trp Ile His Leu Leu Val Val Asp Leu Phe Ala
65                  70                  75                  80

Ala Arg His Ile Phe Arg Asp Gly Met Glu Asn Gln Ile Glu Thr Arg
                85                  90                  95

His Ser Val Ser Phe Cys Leu Phe Phe Cys Pro Ile Gly Ile Leu Thr
            100                 105                 110

His Val Ile Thr Lys Ala Met Thr Lys Thr Thr Arg Thr Glu Ser His
        115                 120                 125

Gly Leu
    130
```

<210> SEQ ID NO 50
<211> LENGTH: 248
<212> TYPE: PRT

<213> ORGANISM: Vigna radiata

<400> SEQUENCE: 50

```
Met Ser Phe Ser Ser Cys Leu Ser His Ser Pro Leu Thr Leu Lys Pro
1               5                   10                  15

Ile Lys Pro Cys Gly Ser Val Gly Met Arg Gln Asn Phe Ala Phe Ser
            20                  25                  30

Phe Arg Ser Asn Trp Pro Glu Leu Cys Asn Arg His Ile Val Gly Ser
        35                  40                  45

Arg Arg Leu Gln Gly Asn Leu Pro Arg Val Asn Leu Ser Gly Asp Trp
    50                  55                  60

Ser Phe Ile Gly Gly Ser Lys Ile Val Met Lys Pro Asn Ala Thr Arg
65                  70                  75                  80

Leu Leu His Tyr Pro Lys Arg Gly Gln Met Gln Ala Ser Cys Phe Ile
                85                  90                  95

Gly Ser Gln Leu Ala Ser Thr Ala Phe Thr Ala Gly Thr Val Ala Val
            100                 105                 110

Leu Pro Phe Tyr Thr Leu Met Val Leu Ala Pro Asn Ser Asp Leu Thr
        115                 120                 125

Lys Lys Ser Met Glu Ser Ser Leu Pro Tyr Val Val Leu Gly Ile Leu
    130                 135                 140

Tyr Ala Tyr Leu Leu Tyr Leu Ser Trp Thr Pro Glu Thr Val Arg Leu
145                 150                 155                 160

Ile Phe Ala Ser Lys Tyr Leu Leu Pro Glu Leu Pro Gly Ile Ala Arg
                165                 170                 175

Met Phe Ser Ser Glu Leu Thr Leu Ala Ser Ala Trp Ile His Leu Leu
            180                 185                 190

Val Val Asp Leu Phe Ala Ala Arg His Val Phe Gln Asp Gly Leu Lys
        195                 200                 205

Asn Gln Ile Glu Thr Arg His Ser Val Ser Phe Cys Leu Phe Phe Cys
    210                 215                 220

Pro Ile Gly Ile Leu Thr His Ile Ile Thr Lys Ala Ile Thr Lys Ala
225                 230                 235                 240

Ala Thr Lys Glu Gly His Gly Val
                245
```

<210> SEQ ID NO 51
<211> LENGTH: 247
<212> TYPE: PRT
<213> ORGANISM: Vigna radiata

<400> SEQUENCE: 51

```
Met Ala Phe Ser Ser Phe Phe Phe His Ser Pro Thr Leu Leu Lys Ile
1               5                   10                  15

Asp His Leu Gly Gln Thr Lys Arg Pro Cys Gly Lys Val Glu Lys Gly
            20                  25                  30

Gln Lys Phe Pro Phe Ser Val Arg Ser Asn Gly Ala Glu Thr Glu Leu
        35                  40                  45

Cys Asn Gln Ser Gln Leu Ser Gln Arg Ser Arg Val Arg Asp Trp Ser
    50                  55                  60

Phe Met Arg Gly Ser Arg Val Ala Met Lys Pro Lys Ile Leu Arg Leu
65                  70                  75                  80

Ala Pro Ser Arg Lys Val Pro Arg Leu Tyr Ala Ser Trp Leu Ser Gly
                85                  90                  95

Ser Glu Leu Ala Ser Thr Ala Phe Thr Leu Gly Thr Thr Ala Val Leu
```

100 105 110

Pro Phe Tyr Thr Leu Met Val Leu Ala Pro Asn Ser Gln Leu Thr Lys
115 120 125

Lys Ser Met Glu Ser Ser Val Pro Tyr Ile Gly Leu Gly Val Leu Tyr
130 135 140

Ala Tyr Leu Leu His Leu Ser Trp Thr Pro Glu Thr Val Gly Leu Ile
145 150 155 160

Phe Ala Ser Lys Tyr Leu Leu Pro Glu Leu Thr Ser Ile Gly Lys Met
165 170 175

Phe Ser Ser Glu Met Thr Leu Ala Ser Ala Trp Ile His Leu Leu Val
180 185 190

Ile Asp Leu Tyr Ala Ala Arg His Val Phe Leu Asp Gly Leu Glu Asn
195 200 205

Gln Ile Glu Thr Arg His Ser Val Ser Leu Cys Leu Phe Phe Cys Pro
210 215 220

Ile Gly Val Leu Thr His Val Ile Thr Lys Ala Thr Thr Lys Ser Ser
225 230 235 240

Arg Glu Asn Lys Ser Gly Leu
245

<210> SEQ ID NO 52
<211> LENGTH: 243
<212> TYPE: PRT
<213> ORGANISM: Trigonella foenum-graecum

<400> SEQUENCE: 52

Met Ser Phe Ser Ser Cys Tyr Ser His Ser Pro Leu Pro Phe Asn Asn
1 5 10 15

Lys Asp Ile Lys Leu Cys Arg Thr Val Gly Gln Val Lys Leu Asn Phe
20 25 30

Pro Phe Ala Ile Arg Ser Asn Gly Val Glu Leu Cys Thr Arg Arg Ile
35 40 45

Ser Arg Cys Arg Phe Asp Leu Ser Gly Asp Trp Ser Phe Ile Gly Gly
50 55 60

Ser Arg Ile Val Val Lys Pro Lys Ala Ala Arg Ser Val Arg Tyr Thr
65 70 75 80

Lys Arg Ser Gln Ile His Ala Ser Trp Phe Met Gly Ser Gln Leu Ala
85 90 95

Ser Thr Val Phe Thr Trp Gly Thr Ile Ala Val Leu Pro Phe Tyr Thr
100 105 110

Leu Met Val Leu Ala Pro Lys Ser Glu Leu Thr Lys Lys Ser Met Glu
115 120 125

Ser Asn Leu Pro Tyr Val Val Leu Gly Val Leu Tyr Ala Tyr Leu Leu
130 135 140

Cys Leu Ser Trp Thr Pro Glu Thr Val Arg Leu Ile Phe Ala Ser Lys
145 150 155 160

Tyr Leu Leu Pro Glu Leu Thr Ser Ile Gly Lys Met Phe Ser Ser Glu
165 170 175

Leu Thr Leu Ala Ser Ala Trp Ile His Leu Leu Val Val Asp Leu Phe
180 185 190

Ala Ala Arg His Ile Phe Arg Asp Gly Met Glu Asn Gln Ile Glu Thr
195 200 205

Arg His Ser Val Ser Phe Cys Leu Phe Phe Cys Pro Val Gly Ile Val
210 215 220

```
Thr His Val Ile Thr Lys Ala Met Thr Ile Lys Thr Arg Lys Glu Gly
225                 230                 235                 240

His Gly Leu


<210> SEQ ID NO 53
<211> LENGTH: 234
<212> TYPE: PRT
<213> ORGANISM: Cichorium intybus

<400> SEQUENCE: 53

Met Ala Phe Ser Ser Cys Leu Cys His His Gln Leu Ala Leu Lys Ile
1               5                   10                  15

Asn Leu Leu Thr Ser Pro Ser Lys Pro Thr Phe Ala Leu Lys Ala Met
            20                  25                  30

Asn Thr Glu Phe Tyr Gly Ile His Ile Gly Ser Lys Leu Gly Asn Gln
        35                  40                  45

Trp Ser Phe Met Lys Gly Ser Gln Ala Ile Ile Arg Pro Asn Pro Gly
    50                  55                  60

Ser Phe Asn Leu His Gln Lys Ser Ser Lys Leu Gln Ala Ser Trp Phe
65                  70                  75                  80

Ala Ser Met His Leu Ala Ser Asp Ala Phe Thr Leu Gly Thr Ala Ala
                85                  90                  95

Val Leu Pro Phe Tyr Thr Leu Met Val Ala Ala Pro Lys Ser Glu Leu
            100                 105                 110

Thr Lys Lys Cys Met Arg Ser Ser Ile Pro Tyr Val Val Leu Gly Val
        115                 120                 125

Leu Tyr Ser Tyr Leu Leu Tyr Leu Ser Trp Thr Pro Asp Thr Val Arg
    130                 135                 140

Leu Met Phe Ala Ser Lys Tyr Trp Leu Pro Glu Leu Pro Gly Val Ala
145                 150                 155                 160

Lys Met Phe Ser Asn Glu Met Thr Leu Ala Ser Ala Trp Ile His Leu
                165                 170                 175

Leu Ala Val Asp Leu Tyr Ala Ala Arg Gln Val Tyr His Asp Gly Leu
            180                 185                 190

Glu Lys Glu Ile Glu Thr Arg His Ser Val Ser Leu Cys Leu Leu Phe
        195                 200                 205

Cys Pro Ile Gly Ile Leu Val His Ala Ile Thr Lys Ala Leu Ile Ser
    210                 215                 220

Thr Tyr Arg Glu Ser Lys Thr Glu Ile His
225                 230


<210> SEQ ID NO 54
<211> LENGTH: 228
<212> TYPE: PRT
<213> ORGANISM: Allium cepa

<400> SEQUENCE: 54

Met Pro Leu Leu Cys Ser Cys Asp Ser Arg Ile Tyr Lys Gln Ala Thr
1               5                   10                  15

Pro Leu Ser Asn Gln Leu Asn Lys Trp Arg Gly Leu Ser Ser His Ala
            20                  25                  30

Gln Gln Phe Ile Pro Asn Gly Ser Lys Asp Ile Val Gln Trp Ser Phe
        35                  40                  45

Lys Gly Gly Ser Lys Ile Val Ile Gln Pro Lys Ile Ser Lys Ile Ser
    50                  55                  60

Tyr His Lys Arg Gly Ser Asp Ile Ser Ala Tyr Trp Ile Pro Thr Ser
```

```
65                  70                  75                  80

Gln Ile Ala Ser Asn Ala Phe Thr Met Gly Thr Val Ala Val Leu Pro
                85                  90                  95

Phe Tyr Thr Leu Met Val Val Ala Pro Asn Ser Lys Leu Thr Lys Arg
            100                 105                 110

Thr Met Glu Ser Ser Ile Pro Tyr Val Val Leu Gly Met Leu Tyr Met
        115                 120                 125

Tyr Leu Leu Tyr Leu Ser Trp Thr Pro Glu Thr Leu Gly Tyr Ile Phe
    130                 135                 140

Ala Thr Lys Tyr Trp Leu Pro Glu Leu Ser Gly Ile Ser Lys Met Phe
145                 150                 155                 160

Ser Asn Glu Thr Cys Thr Ser Ser Ala Trp Ile His Leu Leu Thr Val
                165                 170                 175

Asp Leu Phe Ala Ala Arg Gln Val Phe Gln Asp Gly Ile Lys Asn Lys
            180                 185                 190

Ile Glu Thr Arg His Ser Val Ser Leu Cys Leu Leu Cys Cys Pro Ile
        195                 200                 205

Gly Ile Ala Thr His Ala Ile Thr Lys Ala Leu Lys Arg Val Ser Asp
    210                 215                 220

Ser Arg Ser His
225


<210> SEQ ID NO 55
<211> LENGTH: 249
<212> TYPE: PRT
<213> ORGANISM: Allium cepa

<400> SEQUENCE: 55

Met Ser Leu His Tyr Ser Phe Cys Asn Thr Arg Ile Ser His Gln Val
1               5                   10                  15

Val His Ser Trp Asn Ala Pro Asp Arg Tyr Ala Val Tyr Ala Phe Leu
            20                  25                  30

Ser Ala Arg Asn Lys His Asp Glu His Ile Gly Arg Gln Val Ala His
        35                  40                  45

Thr Lys Ser Arg Asn Arg Val Lys Trp Ser Phe Arg Gly Gly Ser Glu
    50                  55                  60

Leu Phe Ile Gln Pro Lys Ala Thr Arg Thr Asp Arg Gln Lys His Arg
65                  70                  75                  80

Ser Ala Leu Leu Thr Ser Cys Leu Thr Ser Ser Gln Ile Ala Ala Lys
                85                  90                  95

Ala Phe Thr Trp Gly Thr Ile Ala Val Leu Pro Phe Tyr Thr Leu Met
            100                 105                 110

Val Val Ala Pro Asn Ala Lys Leu Thr Lys Arg Ala Ile Glu Ser Asn
        115                 120                 125

Thr Pro Tyr Ile Ile Leu Gly Ala Ile Tyr Ser Tyr Leu Leu Tyr Leu
    130                 135                 140

Ser Trp Ser Pro Ser Thr Leu Arg Thr Met Phe Ala Ser Lys Tyr Trp
145                 150                 155                 160

Leu Pro Gln Leu Ser Gly Ile Cys Ser Met Phe Ser Lys Glu Met Thr
                165                 170                 175

Val Ala Ser Ala Trp Ile His Leu Leu Ala Val Asp Leu Phe Ala Ala
            180                 185                 190

Arg Gln Val Tyr Cys Asp Gly Ile Leu Asn Asn Ile Glu Thr Arg His
        195                 200                 205
```

```
Ser Ile Ser Leu Cys Leu Leu Phe Cys Pro Ile Gly Ile Ala Ile His
    210                 215                 220

Ala Ile Thr Lys Ala Leu Thr Lys Tyr Phe Leu Asn Tyr Asn Phe Ser
225                 230                 235                 240

Glu Glu Met Lys Leu Gly Leu Arg Ser
                245


<210> SEQ ID NO 56
<211> LENGTH: 248
<212> TYPE: PRT
<213> ORGANISM: Hordeum vulgare

<400> SEQUENCE: 56

Met Ala Ala Pro Leu Pro Ser Pro Leu Pro Arg Ala Arg Gln Leu His
1               5                   10                  15

His Leu Val Asp Ser Arg Gln Glu Met Ala Ala Ser Pro Thr Ala Leu
            20                  25                  30

Ala Leu Ala Leu Ser Pro Thr Thr Arg Val Val Val Arg Arg Thr Pro
        35                  40                  45

Ala Pro Arg Val Ala Ala Val Ser Pro Gly Gln Leu Arg Ala Ser Ser
    50                  55                  60

Trp Gly Ala Pro Leu Pro Leu Arg Pro Glu Leu Ala Ala Ala Pro Pro
65                  70                  75                  80

Arg Pro Gly Ala Ala Arg Arg Arg Ala Pro Leu Leu Arg Pro Arg Ala
                85                  90                  95

Trp Leu Ser Thr Ser Gln Ile Ala Ser Ser Ala Phe Thr Leu Gly Thr
            100                 105                 110

Val Ala Val Leu Pro Phe Tyr Thr Leu Met Ile Ala Ala Pro Asn Ala
        115                 120                 125

Asn Ile Thr Lys Arg Thr Val Glu Ser Thr Ala Pro Tyr Val Ala Leu
    130                 135                 140

Gly Ile Leu Tyr Ala Tyr Leu Leu Tyr Leu Ser Trp Thr Pro Asp Thr
145                 150                 155                 160

Ile Arg Ala Met Phe Ala Ser Lys Tyr Trp Leu Pro Glu Leu Pro Gly
                165                 170                 175

Ile Val Arg Met Phe Ala Ser Glu Met Thr Val Ala Ser Ala Trp Ile
            180                 185                 190

His Leu Leu Ala Val Asp Leu Phe Ala Ala Arg Gln Val Tyr His Asp
        195                 200                 205

Gly Ile Lys Asn Asn Ile Glu Thr Arg His Ser Val Ser Leu Cys Leu
    210                 215                 220

Leu Phe Cys Pro Ile Gly Ile Ala Ala His Ala Leu Thr Lys Val Leu
225                 230                 235                 240

Ala Gly Ser Thr Gly Arg Ser His
                245


<210> SEQ ID NO 57
<211> LENGTH: 248
<212> TYPE: PRT
<213> ORGANISM: Citrus sinensis

<400> SEQUENCE: 57

Met Val Val Ala Gly Ile Phe Ile Phe Ala His Ser Met Ala Ile Ser
1               5                   10                  15

Ser Cys Leu Cys His Pro Leu Val Leu Pro Leu Lys Asp Lys Pro Ile
            20                  25                  30
```

-continued

```
Gly Thr Trp Gly Asn Val Gly Val Asp Gln Arg Leu Thr Ser Ala Pro
        35                  40                  45

Arg Ser Met Asn Ala Glu Thr Phe Gly Arg Gln Ile Thr Gly Val Gly
    50                  55                  60

Thr Asp Leu Gln Ser Glu Trp Ser Phe Leu Gly Gly Ser Arg Val Ile
65                  70                  75                  80

Ile Arg Pro Gln Val Thr Lys Phe Ile Arg His Gln Lys Gly Phe His
                85                  90                  95

Ile His Ala Ser Trp Leu Ser Gly Pro Gln Leu Val Ser Thr Val Phe
            100                 105                 110

Thr Leu Gly Thr Ala Gly Val Leu Pro Phe Tyr Thr Leu Met Val Phe
        115                 120                 125

Ala Pro Lys Ala Glu Leu Thr Lys Lys Ser Met Glu Ser Ser Ile Pro
    130                 135                 140

Tyr Val Val Leu Gly Val Leu Tyr Ala Tyr Leu Leu Tyr Leu Ser Trp
145                 150                 155                 160

Thr Pro Asp Thr Leu Arg Leu Met Phe Ala Ser Lys Tyr Trp Leu Pro
                165                 170                 175

Glu Leu Pro Gly Ile Ala Lys Met Phe Ser Ser Glu Ile Thr Leu Ala
            180                 185                 190

Ser Ala Trp Ile His Leu Leu Ala Val Asp Leu Phe Ala Ala Ser His
        195                 200                 205

Val Phe Gln Asp Gly Leu Gln Asn Gln Ile Glu Thr Arg His Ser Val
    210                 215                 220

Ser Leu Cys Leu Leu Phe Cys Pro Ile Gly Ile Leu Thr His Val Ile
225                 230                 235                 240

Thr Lys Ala Leu Thr Lys Ser Ser
                245


<210> SEQ ID NO 58
<211> LENGTH: 235
<212> TYPE: PRT
<213> ORGANISM: Cicer arietinum

<400> SEQUENCE: 58

Met Ala Phe Ser Ser Cys Phe Cys Tyr Ser Ser Leu Leu Gly Leu Lys
1               5                   10                  15

Gly Gln Lys Ile Ser Phe Pro Ile Lys Ser Asn Cys Asp Glu His Tyr
            20                  25                  30

Leu Cys Asn Lys Leu Ile Leu Lys Ser Lys Val Asn Leu Ile Arg Asp
        35                  40                  45

Trp Ser Phe Ile Gly Gly Gly Ser Arg Arg Ile Val Val Lys Gln Lys
    50                  55                  60

Val Met Arg Met Ala Ser Tyr Arg Lys Ala Gly Pro Val Tyr Ala Ser
65                  70                  75                  80

Leu Leu Ser Gly Ser Gln Leu Ala Ser Ser Ala Phe Thr Val Gly Thr
                85                  90                  95

Thr Ala Val Leu Pro Phe Tyr Thr Leu Met Val Leu Ala Pro Asn Ser
            100                 105                 110

Glu Leu Thr Lys Lys Ser Met Gln Ser Asn Val Pro Tyr Ala Val Leu
        115                 120                 125

Gly Ile Leu Tyr Ala Tyr Leu Leu Tyr Leu Ser Trp Thr Pro Glu Thr
    130                 135                 140

Val Glu Leu Ile Phe Ala Ser Lys Tyr Leu Leu Pro Glu Leu Asn Ser
145                 150                 155                 160
```

```
Ile Gly Lys Met Phe Ser Ser Glu Met Thr Leu Ala Ser Ala Trp Ile
                165                 170                 175

His Leu Leu Val Val Asp Leu Phe Ala Ala Arg Gln Val Phe Leu Asp
            180                 185                 190

Gly Gln Glu Asn Gln Ile Glu Thr Arg His Ser Val Ser Leu Cys Leu
        195                 200                 205

Phe Phe Cys Pro Val Gly Ile Leu Ser His Val Ile Thr Lys Ala Met
    210                 215                 220

Thr Lys Asn Thr Lys Glu Asn Lys His Asp Leu
225                 230                 235


<210> SEQ ID NO 59
<211> LENGTH: 241
<212> TYPE: PRT
<213> ORGANISM: Glycine max

<400> SEQUENCE: 59

Met Ser Phe Ser Ser Cys Phe Ser His Ser Pro Leu Thr Phe Lys Ala
1               5                   10                  15

Met Lys Pro Cys Gly Ser Val Gly Lys Gly Gln Asn Phe Ala Phe Pro
            20                  25                  30

Ile Arg Ser Asn Gly Ala Glu Leu Cys Lys Gly Arg Ile Val Arg Ser
        35                  40                  45

Arg Val Asn Leu Ser Gly Asp Trp Asn Phe Met Gly Gly Ser Arg Ile
    50                  55                  60

Ile Val Lys Pro Thr Ala Thr Arg Leu Leu Leu His Tyr Pro Lys Arg
65                  70                  75                  80

Gly Gln Met Lys Val Ser Cys Phe Ile Gly Ser Gln Leu Ala Ser Thr
                85                  90                  95

Ala Phe Thr Ala Gly Thr Ile Ala Val Leu Pro Phe Tyr Thr Leu Met
            100                 105                 110

Val Leu Ala Pro Lys Ser Glu Leu Thr Lys Lys Ser Met Glu Ser Ser
        115                 120                 125

Ile Pro Tyr Val Val Leu Ser Ile Leu Tyr Ala Tyr Leu Leu Tyr Leu
    130                 135                 140

Ser Trp Thr Pro Glu Thr Val Arg Leu Ile Phe Ala Ser Lys Tyr Leu
145                 150                 155                 160

Leu Pro Glu Leu Pro Gly Ile Ala Lys Met Phe Ser Ser Glu Met Thr
                165                 170                 175

Leu Ala Ser Ala Trp Ile His Leu Leu Val Ile Asp Leu Phe Ala Ala
            180                 185                 190

Arg His Val Phe Gln Asp Gly Leu Lys Asn Gln Ile Glu Thr Arg His
        195                 200                 205

Ser Val Ser Phe Cys Leu Phe Phe Cys Pro Ile Gly Ile Leu Thr His
    210                 215                 220

Val Ile Thr Lys Ala Met Thr Lys Pro Ala Thr Lys Glu Gly His Gly
225                 230                 235                 240

Leu


<210> SEQ ID NO 60
<211> LENGTH: 241
<212> TYPE: PRT
<213> ORGANISM: Glycine max

<400> SEQUENCE: 60
```

-continued

Met Tyr Phe Ser Ser Cys Phe Ser His Ser Pro Leu Thr Leu Lys Ala
1 5 10 15

Met Lys Pro Cys Gly Ser Val Gly Lys Gly Lys Asn Phe Ala Phe Pro
20 25 30

Ile Arg Ser Asn Gly Ala Glu Leu Cys Asp Gly His Ile Val Arg Ser
35 40 45

Arg Val Asn Leu Ser Gly Asp Trp Ser Phe Ile Gly Gly Ser Arg Ile
50 55 60

Ile Val Lys Pro Lys Ala Thr Arg Leu Leu Leu His Tyr Pro Lys Arg
65 70 75 80

Gly Gln Met Gln Ala Ser Cys Phe Ile Gly Ser Gln Leu Ala Ser Thr
85 90 95

Val Phe Thr Val Gly Thr Ile Ala Val Leu Pro Phe Tyr Thr Leu Met
100 105 110

Val Leu Ala Pro Lys Ser Glu Leu Thr Lys Lys Ser Met Glu Ser Ser
115 120 125

Ile Pro Tyr Val Val Leu Ser Ile Leu Tyr Ala Tyr Leu Leu Tyr Leu
130 135 140

Ser Trp Thr Pro Glu Thr Val Arg Leu Ile Phe Ala Ser Lys Tyr Leu
145 150 155 160

Leu Pro Glu Leu Ala Gly Ile Ala Lys Met Phe Ser Ser Glu Met Thr
165 170 175

Leu Ala Ser Ala Trp Ile His Leu Leu Val Val Asp Leu Phe Ala Ala
180 185 190

Arg His Ile Phe Gln Asp Gly Leu Lys Asn Gln Ile Glu Thr Arg His
195 200 205

Ser Val Ser Phe Cys Leu Phe Phe Cys Pro Ile Gly Ile Leu Thr His
210 215 220

Val Ile Thr Lys Ser Met Thr Lys Pro Ala Arg Lys Glu Gly His Gly
225 230 235 240

Leu

<210> SEQ ID NO 61
<211> LENGTH: 250
<212> TYPE: PRT
<213> ORGANISM: Glycine max

<400> SEQUENCE: 61

Met Ala Phe Ser Ser Phe Phe Ser His Ser Pro Leu Ala Leu Lys Ile
1 5 10 15

Asp Arg Leu Gly Gln Thr Ile Lys Pro Cys Gly Thr Val Glu Lys Gly
20 25 30

Gln Lys Phe Ser Phe Pro Ile Arg Ser Asn Gly Gly Glu Leu Glu Leu
35 40 45

Cys Tyr Gln Ser Gln Leu Asn Gln Arg Ser Arg Val Asn Leu Ile Arg
50 55 60

Asp Trp Ser Phe Ile Gly Gly Ser Arg Ile Val Val Lys Pro Asn Phe
65 70 75 80

Val Arg Leu Val Pro Phe Arg Lys Ala Ser Arg Val Tyr Ala Ser Trp
85 90 95

Leu Ser Gly Ser Gln Leu Ala Ser Ser Ala Phe Thr Leu Gly Thr Thr
100 105 110

Ala Val Leu Pro Phe Tyr Thr Leu Met Val Leu Ala Pro Asn Ser Glu
115 120 125

Leu Thr Arg Lys Ser Met Glu Ser Ser Val Pro Tyr Val Val Leu Gly
130 135 140

Ile Leu Tyr Ala Tyr Leu Leu Tyr His Ser Trp Thr Pro Glu Thr Val
145 150 155 160

Gly Leu Ile Phe Ala Ser Lys Tyr Leu Leu Pro Glu Leu Thr Ser Ile
165 170 175

Gly Lys Met Phe Ser Ser Glu Met Thr Leu Ala Ser Ala Trp Ile His
180 185 190

Leu Leu Val Met Asp Leu Phe Ala Ala Arg His Val Phe Leu Asp Gly
195 200 205

Leu Glu Asn Gln Ile Glu Thr Arg His Ser Val Ser Leu Cys Leu Phe
210 215 220

Phe Cys Pro Ile Gly Val Leu Ser His Ala Ile Thr Lys Glu Met Thr
225 230 235 240

Lys Ser Ala Arg Lys Asn Lys His Ser Leu
245 250

<210> SEQ ID NO 62
<211> LENGTH: 248
<212> TYPE: PRT
<213> ORGANISM: Phaseolus vulgaris

<400> SEQUENCE: 62

Met Ser Phe Ser Ser Cys Leu Ser His Ser Pro Leu Thr Leu Lys Ala
1 5 10 15

Ile Lys Pro Cys Gly Ser Val Gly Lys Gly Gln Asn Phe Gly Phe Ser
20 25 30

Phe Arg Ser Asn Glu Ala Glu Leu Cys Asn Ser His Ile Ala Gly Ser
35 40 45

Gly Arg Leu Gln Gly Asn Leu Pro Arg Val Asn Leu Ser Gly Asp Trp
50 55 60

Ser Phe Ile Gly Gly Ser Lys Ile Val Val Lys Pro Asn Ala Thr Gly
65 70 75 80

Leu Leu Pro Tyr Pro Lys Arg Gly Arg Met Gln Ala Ser Cys Phe Ile
85 90 95

Gly Ser Gln Leu Ala Ser Thr Ala Phe Thr Ala Gly Thr Val Ala Val
100 105 110

Leu Pro Phe Tyr Thr Leu Met Val Leu Ala Pro Asn Ser Val Leu Thr
115 120 125

Lys Lys Ser Met Asp Ser Ser Leu Pro Tyr Val Val Leu Gly Ile Leu
130 135 140

Tyr Ala Tyr Leu Leu Tyr Leu Ser Trp Thr Pro Glu Thr Val Arg Leu
145 150 155 160

Ile Phe Ala Ser Lys Tyr Leu Leu Pro Glu Leu Pro Gly Ile Ala Arg
165 170 175

Met Phe Ser Ser Glu Met Thr Leu Ala Ser Ala Trp Ile His Leu Leu
180 185 190

Val Val Asp Leu Phe Ala Ala Arg His Val Phe Gln Asp Gly Leu Lys
195 200 205

Asn Gln Ile Glu Thr Arg His Ser Val Ser Phe Cys Leu Phe Phe Cys
210 215 220

Pro Ile Gly Ile Leu Thr His Val Ile Thr Lys Ala Met Thr Lys Pro
225 230 235 240

Ala Thr Lys Glu Gly His Gly Val
245

<210> SEQ ID NO 63
<211> LENGTH: 246
<212> TYPE: PRT
<213> ORGANISM: Vitis vinifera

<400> SEQUENCE: 63

```
Met Val Phe Ser Ser Cys Phe Cys Gln Ser Gln Ile Ser Phe Lys Ile
1               5                   10                  15

Asp Arg Ser Ala Val Ala Ile Arg Pro Gln Cys His Thr Arg Lys Asp
            20                  25                  30

Gln Arg Ser Thr Phe Ala Leu Lys Gly Met Ser Thr Glu Leu Phe Gly
        35                  40                  45

Gln Gln Val Ala Arg Ala Gly Ala Met Arg Ser Ser Glu Trp Ser Phe
    50                  55                  60

Met Arg Gly Ser Arg Ile Ile Ile Arg Pro Lys Val Ala Arg Phe Val
65                  70                  75                  80

Phe Tyr Arg Lys Gly Ser Gly Val Tyr Ala Ser Trp Leu Ala Asn Pro
                85                  90                  95

Gln Ile Ala Ser Ser Val Phe Thr Leu Gly Thr Ala Ala Val Leu Pro
            100                 105                 110

Phe Tyr Thr Leu Met Val Leu Ala Pro Thr Ala Glu Leu Thr Lys Lys
        115                 120                 125

Ser Met Glu Ser Thr Ile Pro Tyr Val Val Leu Gly Leu Leu Tyr Ala
    130                 135                 140

Tyr Leu Leu Tyr Leu Ser Trp Thr Pro Asp Thr Ile Arg Leu Met Phe
145                 150                 155                 160

Ala Ser Lys Tyr Trp Leu Pro Glu Leu Pro Gly Met Ala Lys Met Phe
                165                 170                 175

Ser Asn Glu Met Thr Leu Ala Ser Ala Trp Ile His Leu Leu Ala Ile
            180                 185                 190

Asp Leu Phe Ala Ala Arg Gln Val Phe Gln Asp Gly Leu Glu Asn Lys
        195                 200                 205

Ile Glu Thr Arg His Ser Val Ser Leu Cys Leu Leu Phe Cys Pro Ile
    210                 215                 220

Gly Ile Val Thr His Val Ile Thr Lys Ala Leu Thr Lys Ser Ala Gly
225                 230                 235                 240

Asp Thr Lys His Ser Met
                245
```

<210> SEQ ID NO 64
<211> LENGTH: 230
<212> TYPE: PRT
<213> ORGANISM: Oryza sativa

<400> SEQUENCE: 64

```
Met Ala Ala Leu Leu Leu Leu Ser Ser Ala Ala Arg Val Gly Val Ala
1               5                   10                  15

Ala Pro Leu Ala Leu Arg Gln Gln Arg Pro Val Val Leu Pro Gly Gly
            20                  25                  30

Gln Leu Arg Thr Gly Ser Gly Ala Gly Ala Ala Ser Ala Trp Ala Ala
        35                  40                  45

Arg Pro Leu Arg Pro Glu Leu Ala Ala Val Ser Arg Pro Ala Val Pro
    50                  55                  60

Ala Arg Gly Arg Ala Pro Leu Phe Arg Pro Arg Ala Trp Met Ala Ser
65                  70                  75                  80
```

```
Ser Gln Ile Ala Ser Ser Ala Phe Thr Trp Gly Thr Ile Ala Val Leu
                85                  90                  95

Pro Phe Tyr Thr Leu Met Val Val Ala Pro Asn Ala Asp Val Thr Lys
            100                 105                 110

Arg Ala Val Asp Ser Ser Ala Pro Tyr Val Ala Leu Gly Ile Leu Tyr
        115                 120                 125

Ala Tyr Leu Leu Tyr Leu Ser Trp Thr Pro Asp Thr Leu Arg Ala Met
    130                 135                 140

Phe Ala Ser Lys Tyr Trp Leu Pro Glu Leu Thr Gly Ile Val Arg Met
145                 150                 155                 160

Phe Ala Ser Glu Met Thr Val Ala Ser Ala Trp Ile His Leu Leu Ala
                165                 170                 175

Val Asp Leu Phe Ala Ala Arg Gln Val Tyr His Asp Gly Ile Lys Asn
            180                 185                 190

Asn Ile Glu Thr Arg His Ser Val Ser Leu Cys Leu Leu Phe Cys Pro
        195                 200                 205

Ile Gly Ile Ala Thr His Val Leu Thr Lys Ala Tyr Val Leu Leu Thr
    210                 215                 220

Asn Lys Cys Ala Phe Gln
225                 230


<210> SEQ ID NO 65
<211> LENGTH: 229
<212> TYPE: PRT
<213> ORGANISM: Triticum aestivum

<400> SEQUENCE: 65

Met Ala Ala Ser Ser Pro Ser Ala Leu Ala Leu Ser Thr Thr Thr Arg
1               5                   10                  15

Val Ala Gly Ser Ser Val Leu Leu Ala Val Arg Arg Thr Pro Ala Thr
            20                  25                  30

Arg Val Ala Ala Val Pro Cys Ala Gln Leu Arg Ala Cys Ser Trp Gly
        35                  40                  45

Ala Pro Leu His Leu Arg Pro Glu Leu Ala Ala Ala Pro Ala Pro Cys
    50                  55                  60

Ala Ala Arg Cys Arg Ala Pro Leu Leu Arg Pro Arg Ala Trp Leu Ser
65                  70                  75                  80

Thr Ser Gln Ile Ala Ser Ser Ala Phe Thr Leu Gly Thr Val Ala Val
                85                  90                  95

Leu Pro Phe Tyr Thr Leu Met Ile Ala Ala Pro Asn Ala Asn Ile Thr
            100                 105                 110

Lys Arg Ala Val Glu Ser Thr Ala Pro Tyr Val Ala Leu Gly Leu Leu
        115                 120                 125

Tyr Ala Tyr Leu Leu Tyr Leu Ser Trp Thr Pro Asp Thr Ile Arg Ala
    130                 135                 140

Met Phe Ala Ser Lys Tyr Trp Leu Pro Glu Leu Pro Gly Ile Val Arg
145                 150                 155                 160

Met Phe Ala Ser Glu Met Thr Val Ala Ser Ala Trp Ile His Leu Leu
                165                 170                 175

Ala Val Asp Leu Phe Ala Ala Arg Gln Val Tyr Gln Asp Gly Ile Lys
            180                 185                 190

Asn Asn Ile Glu Thr Arg His Ser Val Ser Leu Cys Leu Leu Phe Cys
        195                 200                 205

Pro Ile Gly Ile Ala Ala His Ala Leu Thr Lys Val Leu Ala Gly Ser
```

```
    210                 215                 220

Thr Gly Arg Ser His
225


<210> SEQ ID NO 66
<211> LENGTH: 232
<212> TYPE: PRT
<213> ORGANISM: Zea mays

<400> SEQUENCE: 66

Met Ala Pro Cys Ala Ser Pro Ser Ala Leu Ala Leu Ser Ala Ser Thr
1               5                   10                  15

Arg Val Ser Ile Leu Arg Leu Pro Leu Ala Leu Arg Gln Arg Ala Glu
            20                  25                  30

Ala Arg Val Pro Gly Ala Gln Phe Arg Pro Ser Thr Ala Cys Ser Trp
        35                  40                  45

Ala Arg Pro Leu Leu Pro Glu Leu Ala Gly Ala Val Pro Arg Ala Gly
    50                  55                  60

Ala Arg Gly Thr Gly Arg Arg Thr Gln Pro Leu Phe Arg Pro Arg Ala
65                  70                  75                  80

Leu Thr Thr Thr Ser Gln Ile Ala Ser Cys Ala Phe Thr Leu Gly Thr
                85                  90                  95

Val Ala Val Leu Pro Phe Tyr Thr Leu Met Val Val Ala Pro Asn Ala
            100                 105                 110

Asp Ile Thr Lys Arg Thr Val Glu Ser Gly Ala Pro Tyr Val Ala Leu
        115                 120                 125

Gly Leu Leu Tyr Ala Tyr Leu Leu Tyr Leu Ser Trp Thr Pro Asp Thr
    130                 135                 140

Leu Arg Ala Met Phe Ala Ser Lys Tyr Trp Leu Pro Glu Leu Ala Gly
145                 150                 155                 160

Ile Val Arg Met Phe Ala Ser Glu Met Thr Val Ala Ser Ala Trp Ile
                165                 170                 175

His Leu Leu Ala Val Asp Leu Phe Ala Ala Arg Gln Val Tyr His Asp
            180                 185                 190

Gly Leu Arg Asn Asn Val Glu Thr Arg His Ser Val Ser Leu Cys Leu
        195                 200                 205

Leu Phe Cys Pro Val Gly Ile Leu Ala His Val Leu Thr Lys Val Leu
    210                 215                 220

Ala Gly Ala Val Ala Arg Ser His
225                 230


<210> SEQ ID NO 67
<211> LENGTH: 246
<212> TYPE: PRT
<213> ORGANISM: Ricinus communis

<400> SEQUENCE: 67

Met Ala Phe Ser Ser Cys Phe Cys Pro Ser His Ile His Leu Lys Thr
1               5                   10                  15

Gly Tyr Pro Arg Arg Val Ile Arg Pro Gly Arg Pro Val Glu Lys Asp
            20                  25                  30

Gly Gln Lys Phe Phe Ser Leu Arg Ser Asn Ser Thr Glu Leu Ser Gly
        35                  40                  45

Arg Gln Val Ala Lys Leu Gly Ala Asp Leu Leu Ser Asp Trp Ser Phe
    50                  55                  60

Ile Gly Gly Ser Arg Ile Ala Ile Arg Pro Lys Leu Ala Arg Ala Ile
```

-continued 65 70 75 80

Val Tyr Arg Lys His Ser Gly Val His Ala Ser Trp Leu Ser Ser Tyr
85 90 95

Gln Leu Ala Ser Thr Ala Phe Thr Leu Gly Thr Ala Ala Val Leu Pro
100 105 110

Phe Tyr Thr Leu Met Val Val Ala Pro Lys Ala Glu Leu Thr Arg Lys
115 120 125

Ser Met Glu Ser Ser Ile Pro Tyr Val Val Leu Gly Val Leu Tyr Ala
130 135 140

Tyr Leu Leu Tyr Leu Ser Trp Thr Pro Asp Thr Val Arg Leu Met Phe
145 150 155 160

Ala Ser Gln Tyr Trp Leu Pro Glu Leu Pro Gly Ile Ala Lys Met Phe
165 170 175

Ser Ser Glu Met Thr Leu Ala Ser Ala Trp Ile His Leu Leu Ala Val
180 185 190

Asp Leu Phe Ala Ala Arg Gln Val Phe His Asp Gly Leu Glu Asn Glu
195 200 205

Ile Glu Thr Arg His Ser Val Ser Leu Cys Leu Leu Phe Cys Pro Ile
210 215 220

Gly Ile Val Ser His Val Leu Thr Lys Ala Leu Thr Arg Ser Ala Ala
225 230 235 240

Ser Thr Arg Arg Gly Thr
245

<210> SEQ ID NO 68
<211> LENGTH: 246
<212> TYPE: PRT
<213> ORGANISM: Populus trichocarpa

<400> SEQUENCE: 68

Met Ala Phe Ser Ser Cys Phe Cys Tyr Pro Gln Phe Ser Leu Lys Asn
1 5 10 15

Asp Cys Ser Gly Leu Thr Ile Arg Ser His His Ile Val Gly Lys Asp
20 25 30

Arg Lys Leu Phe Ser Ser Leu Arg Ser Asn Ser Ile Glu Leu Phe Gly
35 40 45

Gln Arg Val Ala Arg Val Gly Ala Asp Leu His Arg Asp Trp Asn Phe
50 55 60

Leu Gly Gly Ser Arg Ile Ile Val His Pro Lys Leu Thr Asn Phe Leu
65 70 75 80

Val Tyr Arg Lys Ser Ser Gly Val Asn Ala Ser Trp Leu Thr Ser Thr
85 90 95

Gln Ile Ala Ser Ser Val Phe Thr Leu Gly Thr Ala Ala Val Leu Pro
100 105 110

Phe Tyr Thr Leu Met Val Val Ala Pro Lys Ala Glu Val Thr Arg Lys
115 120 125

Ser Met Glu Ser Ser Ile Pro Tyr Ile Val Leu Gly Leu Leu Tyr Ala
130 135 140

Phe Leu Leu Tyr Leu Ser Trp Thr Pro Asp Thr Met Arg Leu Met Phe
145 150 155 160

Ala Ser Gln Tyr Trp Leu Pro Glu Leu Pro Gly Ile Ala Lys Met Phe
165 170 175

Ser Asn Glu Met Thr Leu Ala Ser Ala Trp Ile His Leu Leu Ala Val
180 185 190

```
Asp Leu Phe Ala Ala Arg Gln Val Phe Asn Asp Gly Leu Glu Asn Glu
        195                 200                 205

Val Glu Thr Arg His Ser Val Ser Leu Cys Leu Leu Phe Cys Pro Ile
    210                 215                 220

Gly Ile Ala Thr His Cys Ile Thr Lys Ala Leu Thr Lys Gly Ser Gly
225                 230                 235                 240

Thr Thr Thr His Asp Met
                245


<210> SEQ ID NO 69
<211> LENGTH: 242
<212> TYPE: PRT
<213> ORGANISM: Malus domestica

<400> SEQUENCE: 69

Met Ala Phe Cys Ser Cys Phe Cys His Ser Pro Phe Ser Phe Lys Val
1               5                   10                  15

Asp Tyr Gly Asn Lys Thr Ile Arg His Trp Ser Asn Asp Thr Ser Ala
            20                  25                  30

Gln Ser Phe Thr Phe Thr Leu Arg Gly Tyr Asn Thr Glu Val Leu Gly
        35                  40                  45

His Gln Val Val Thr Val Glu Ser His Met His Lys Asp Trp Ser Phe
    50                  55                  60

Val Gly Gly Ser Thr Val Pro Ile Arg Pro Lys Leu Glu Arg Tyr Ile
65                  70                  75                  80

Pro Arg Arg Lys Cys Ser Gly Val Tyr Met Ser Trp Leu Ala Ser Ser
                85                  90                  95

Gln Ile Ala Ser Arg Val Phe Thr Val Gly Thr Thr Ala Val Leu Pro
            100                 105                 110

Phe Tyr Ala Leu Met Val Leu Ala Pro Lys Ala Gln Leu Thr Lys Val
        115                 120                 125

Phe Thr Glu Ser Ser Ile Pro Asn Val Leu Leu Gly Val Leu Tyr Ala
    130                 135                 140

Tyr Leu Leu Tyr Leu Ser Trp Thr Pro Glu Thr Leu Gln Leu Ile Phe
145                 150                 155                 160

Gly Ser Lys Tyr Trp Leu Pro Glu Leu Thr Gly Ile Ala Lys Met Phe
                165                 170                 175

Thr Asn Glu Ile Thr Leu Ala Ser Ala Trp Ile His Leu Leu Val Val
            180                 185                 190

Asp Leu Phe Ala Ala Arg Gln Val Phe Ser Asp Gly Leu Gln Asn Gln
        195                 200                 205

Ile Glu Thr Arg Gln Ser Val Ser Leu Cys Leu Phe Phe Cys Pro Ile
    210                 215                 220

Gly Ile Leu Thr His Val Ile Thr Lys Ala Leu Thr Lys Thr Gly Gly
225                 230                 235                 240

Ser Leu


<210> SEQ ID NO 70
<211> LENGTH: 3267
<212> TYPE: DNA
<213> ORGANISM: Trigonella foenum-graecum
<220> FEATURE:
<221> NAME/KEY: modified_base
<222> LOCATION: (1998)..(2015)
<223> OTHER INFORMATION: a, c, t, g, unknown or other

<400> SEQUENCE: 70
```

-continued

```
tgtctttctc ttcwtgctat tcwcaytcrc cattgccatt taataataag gtacaacact     60
ttctctgctt tcttttcctg ttttttcaat tttctgtttt gtaatcttat ctgcattttt    120
cttgtctttt ttatggatat tttgtacttt tttttttttt taattttcca caaatggggt    180
ttctgtttga tgtgtaaagt tttgaacttt gaataaatat agctgaaatt gaagattctt    240
ttttgtcata gatttgaatc accaatgcat tactaatgaa atgggccttt gagcttttat    300
tttttagttt gtaatagatc tgatgctagg tgcatgttga tgttggtata ttggtaatga    360
actatgtaga agctacactt cagattgata atgtgtctgg tgtttgacac gtgtttgcgg    420
atacaacacg acattaacac atgtggttgc atttgatcac tttcattttc ttaaattgtt    480
acaggtgtct acgacttagt gtcgtgtcgt gtatgtgtta gtgtttcaaa aagttgacac    540
tcctgtatma acaaaccaat atgtgtaaaa aaaactatgt agcaccgaca cttcatattg    600
aagatatgta tggtgtttga gatgcatcag tgtccagcac cgacacaata ctgacacatg    660
tggttacatt taattayttc attttctcaa attatgatca atgtcaatct gtcagtgtcg    720
tgtctggtgt ccgtatctgg cttcattggc aacaamtatg tatttgttca tgtagtcatt    780
gcatattgag ktgtaagaat cgtcagcrcg acctgtatat ttcctgttga agatcaaaca    840
atttagttca tttactctta ygaatggata acctagggtg tatttctggg ttcaagaaat    900
tttattctat tattgattga tcatcacttg gggcaggata taaaactctg taggacagtt    960
gggcaagtga agttgaattt tcctttcgct ataaggagta atggtgttga gctgtgtact   1020
cggcgcattt cgagatgtag attcgactta agtggagatt ggagtttcat aggagggtcc   1080
agaattgttg taaaacctaa agctgcaaga tcggttcgct atacaaaaag aagtcaaata   1140
catgcttcat gtaatctttt ttcatctaat ctaaaattg tacaagctgt tccttagttc   1200
atataattta ccattcakta gaattggctg tgasggcgtt tgaacataaw aaagttaaat   1260
tgytttcwta taacctataa gttttttttcs tawsttatat tckagagctt acraaaataa   1320
rctgaaaaca acttatggac atgtcgtaac ctgtttccag aaactatact aaacagtctc   1380
ataasttctt atgccaataa ataagctcaa ataastcaat ccaaacagga atgcatttaa   1440
tttttargtt accattttg gtggcgttat cataaagtag attactgtaa gtacttttgt   1500
cttatcatct ttatatgaac aacgaaactg gaggcagtgg ttaatatctg ttcattgatc   1560
atggtgtaca atgctatata tgataartta taaccttgca atgtgttgct gaaggcaata   1620
tggttcacaa ttcatgcttt agttgagtta gggtctgttt ggattckctt atttgagttt   1680
accttctaac ataagcattt gtgagactgt ttgagagagt ttatggaaac aacttatata   1740
cgacatgtgc ataacttgtt ttaagttaat ttttataaat tctccaagat agcttatgaa   1800
aacaacttac agattatatg aaaacagctc gactttattt tatttttttgt tatagaaata   1860
acatatgcat aagcacttat atgataaaca aggttttctt gtttaggtgg ataccattga   1920
cttgaattgc ttgttmtaat atacytgaaa attgaytayg atctatgctt aaattgcttg   1980
ttctgcatat tcaytgtnnn nnnnnnnnnn nnnnnggttc atgggatctc aacttgctag   2040
cactgtattt acatggggaa cgattgcagt gctcccgttt tacaccctta tggttctagc   2100
cccgaaatcc gagctggtac gtttcttttt tgtatttgtg aaaaattatg attagtaatc   2160
tcatttcaca attcatattc agttatgata ttctttttca tttcatttat ttggttatga   2220
ttctgatatg ctgattcggt tttctgaaat gcaaaaatac agaccaaaaa gtctatggaa   2280
agtaatttac catatgtagt gctcggcgtt ctatacgctt atttgttgtg cctttcttgg   2340
acccctgaaa cagttcgatt gattttcgcg agtaaatact tactacctga ggtgtgtatt   2400
```

-continued

```
catttattaa tgaagttaaa ttttctttct ctaaagagtt caattatcaa taattgtgtt   2460
atatttgcat actctatgca gcttactagc atagggaaaa tgttctctag tgagttgact   2520
ttagcctctg cttggattca ccttttggtt gttgatcttt ttgctgcaag gtcctgattt   2580
tatctctttg tttttgttgc tcagtaatga gattttgaca caaatttgac aaaaaaaagt   2640
agaaaacaat ttggatagtt aatgccgttc gaatatgcgg ttaattacat agtgaatggt   2700
taatgaatat tacaaaatac aaaatgtcac aagtcattaa ccctgatttt gaacgccgtt   2760
aatcataaac tttaggtgtt caaacatacg tgatattcat taaccattcc aattatgttc   2820
acgatcttca ggttttcaaa tatacataat attctattaa tcacaatttt tgttcaaata   2880
tacaaatgta attgtggtta atgacattca aaatagtggt taattgtgat ctattgatgg   2940
gtaatgagtt atgacacttt gttataatca gtaaccatct actaaatgta attaacctta   3000
tatttgaact acattaacat ttaaattgtt gtcaaatttt atggtctaat tttgtgtcaa   3060
aataacacgg ctctttctca tgcttaaatt atttttctga tagtatttgt ggttctaaat   3120
ccaggcatat tttccgcgat ggaatggaga atcaaattga aacacgacat tcggtttcct   3180
tttgcttgtt cttttgccct gttgggattg taactcatgt catcaccaaa gcaatgacca   3240
taaaaacaag aaaagagggt catggtt                                        3267
```